(12) United States Patent
Tachibana et al.

(10) Patent No.: US 10,604,618 B2
(45) Date of Patent: Mar. 31, 2020

(54) COMPOUND, METHOD FOR MANUFACTURING THE COMPOUND, AND COMPOSITION FOR FORMING ORGANIC FILM

(71) Applicants: SHIN-ETSU CHEMICAL CO., LTD., Tokyo (JP); INTERNATIONAL BUSINESS MACHINES CORPORATION, Armonk, NY (US)

(72) Inventors: Seiichiro Tachibana, Joetsu (JP); Takeru Watanabe, Joetsu (JP); Keisuke Niida, Joetsu (JP); Hiroko Nagai, Joetsu (JP); Takashi Sawamura, Joetsu (JP); Tsutomu Ogihara, Joetsu (JP); Alexander Edward Hess, San Jose, CA (US); Gregory Breyta, San Jose, CA (US); Daniel Paul Sanders, San Jose, CA (US); Rudy J. Wojtecki, San Jose, CA (US)

(73) Assignees: SHIN-ETSU CHEMICAL CO., LTD., Tokyo (JP); INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/013,672

(22) Filed: Jun. 20, 2018

(65) Prior Publication Data
US 2019/0390000 A1 Dec. 26, 2019

(51) Int. Cl.
*C08F 38/00* (2006.01)
*C08G 61/02* (2006.01)
*C08K 5/00* (2006.01)

(52) U.S. Cl.
CPC .............. *C08G 61/02* (2013.01); *C08F 38/00* (2013.01); *C08F 2500/02* (2013.01);
(Continued)

(58) Field of Classification Search
CPC ................ C08G 61/02; C08G 2261/43; C08G 2261/41; C08G 2261/1642;
(Continued)

(56) References Cited

U.S. PATENT DOCUMENTS 8,765,899 B2  7/2014 Karkkainen
9,018,776 B2  4/2015 Song et al.
(Continued)

FOREIGN PATENT DOCUMENTS

JP  2002-334869 A  11/2002
JP  2005-128509 A  5/2005
(Continued)

OTHER PUBLICATIONS

Melissa Hughs, Miguel Jimenez, Saeed Khan, and Miguel A. Garcia-Garibay, Synthesis, Rotational Dynamics, and Photophysical Characterization of a Crystalline Linearly Conjugated Phenyleneethynylene Molecular Dirotor,3 | J. Org. Chem. 2013, 78, 5293-5302. (Year: 2013).*

(Continued)

*Primary Examiner* — Bijan Ahvazi
(74) *Attorney, Agent, or Firm* — Oliff PLC

(57) ABSTRACT

A compound includes two or more structures shown by the following general formula (1-1) in the molecule,

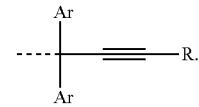

(1-1)

"Ar" represents an aromatic ring or one that contains at least one nitrogen atom and/or sulfur atom optionally having a (Continued)

substituent, and two Ars are optionally bonded with each other to form a ring structure; the broken line represents a bond with Y; Y represents a divalent or trivalent organic group having 6 to 30 carbon atoms that contains an aromatic ring or a heteroaromatic ring optionally having a substituent, the bonds of which are located in a structure of the aromatic ring or the heteroaromatic ring; R represents a hydrogen atom or a monovalent group having 1 to 68 carbon atoms. This compound can be cured even in an inert gas not only in air atmosphere without forming byproducts, and can form an organic under layer film.

13 Claims, 3 Drawing Sheets

(52) U.S. Cl.
CPC ............... *C08G 2261/1642* (2013.01); *C08G 2261/419* (2013.01); *C08G 2261/43* (2013.01); *C08K 5/0016* (2013.01); *C08K 5/0025* (2013.01); *C08L 2203/16* (2013.01)

(58) Field of Classification Search
CPC ............... C08G 2261/419; C08F 38/00; C08F 2500/02; C08K 5/0016; C08K 5/0025; C08L 2203/16
See application file for complete search history.

(56) References Cited

U.S. PATENT DOCUMENTS

| | | |
|---|---|---|
| 9,261,788 B2 | 2/2016 | Tachibana et al. |
| 9,328,246 B2 | 5/2016 | Sullivan et al. |
| 2002/0106909 A1 | 8/2002 | Kato et al. |
| 2005/0255712 A1 | 11/2005 | Kato et al. |
| 2006/0019195 A1 | 1/2006 | Hatakeyama et al. |
| 2006/0204891 A1 | 9/2006 | Hatakeyama |
| 2009/0274978 A1 | 11/2009 | Ohashi et al. |
| 2010/0099044 A1 | 4/2010 | Hatakeyama et al. |
| 2013/0302990 A1 | 11/2013 | Watanabe et al. |
| 2013/0310514 A1 | 11/2013 | Minegishi et al. |
| 2016/0085152 A1 | 3/2016 | Nakafuji et al. |
| 2017/0184968 A1 | 6/2017 | Kori et al. |

FOREIGN PATENT DOCUMENTS

| | | |
|---|---|---|
| JP | 2006-285095 A | 10/2006 |
| JP | 2006-293298 A | 10/2006 |
| JP | 2007-199653 A | 8/2007 |
| JP | 2009-269953 A | 11/2009 |
| JP | 2010-122656 A | 6/2010 |
| JP | 2010-181605 A | 8/2010 |
| JP | 2012-215842 A | 11/2012 |
| JP | 2013-253227 A | 12/2013 |
| JP | 2016-044272 A | 4/2016 |
| JP | 2016-060886 A | 4/2016 |
| JP | 2017-119671 A | 7/2017 |
| KR | 100874655 B1 | 12/2008 |
| WO | 2004/066377 A1 | 8/2004 |
| WO | 2014/208324 A1 | 12/2014 |

OTHER PUBLICATIONS

Apr. 20, 2018 Search Report.
Sep. 27, 2019 Extended European Search Report issued in European Patent Application No. 19178429.7.
Oral, Pavlo O., et al., "Semiempirical UNO-CAS and UNO-CI: Method and Applications in Nonoelectrics", The Journal of Physical Chemistry, vol. 115, No. 41, pp. 11303-11312.
Tommasini, Matteo, et al., "π-Conjugation and End Group Effects in Long Cumulenes: Raman Spectroscopy and OFT Calculations", The Journal of Physical Chemistry, vol. 118, No. 45, pp. 26415-26425.
Jiménez-Urias, Ana, et al., "Synthesis and Characterization of Dumbbell-Like BTD-Based Derivatives to Engineer Organic Building Blocks in Solid-State", Journal of Molecular Structure, vol. 1153, pp. 34-41.

\* cited by examiner (G)

(H)

(I)

(J)

(K)

COMPOUND, METHOD FOR MANUFACTURING THE COMPOUND, AND COMPOSITION FOR FORMING ORGANIC FILM

TECHNICAL FIELD

The present invention relates to a compound, a method for manufacturing the compound and a composition for forming an organic film containing the compound that is usable in an inert gas in a process for producing a semiconductor device.

BACKGROUND ART

Semiconductor devices have been highly integrated and advanced in processing speed by shifting the wavelength of a light source shorter to attain a finer pattern size in lithography technologies using a light exposure (photolithography) as common arts. In order to form such a fine circuit pattern on a semiconductor device substrate (a substrate to be processed), the substrate is usually processed by dry etching using a photoresist film having a formed pattern as an etching mask. Practically, however, there is no dry etching method having a complete etching selectivity between the photoresist film and the substrate to be processed. Accordingly, substrate processing by a multilayer resist process has been commonly used recently. In this method, a middle layer film having a different etching selectivity from a photoresist film (hereinafter, a resist upper layer film) is set between the resist upper layer film and a substrate to be processed, and a pattern is obtained on the resist upper layer film, and subsequently the pattern is transferred to the middle layer film by dry etching using the resist upper layer film pattern as a dry etching mask, and the pattern is further transferred to the substrate to be processed by dry etching using the middle layer film as a dry etching mask.

One of the multilayer resist processes is a three-layer resist process, which can be performed by using a conventional resist composition that is used in a single layer resist process. In this process, an organic under layer film material composed of a composition containing an organic resin is applied onto a substrate to be processed and is baked to form an organic under layer film (hereinafter, an organic film), a resist middle layer film material composed of a silicon-containing resin composition is applied thereto and is baked to form a silicon-containing film (hereinafter, a silicon middle layer film), and a conventional resist upper layer is formed thereon. After patterning the resist upper layer film, the resist upper layer film pattern can be transferred to the silicon middle layer film by dry etching with a fluorine-base gas plasma since organic resist upper layer films have excellent etching selectivity to silicon middle layer films. This method makes it possible to easily transfer a pattern to a silicon middle layer film even in the use of a resist upper layer film without having a sufficient film thickness for directly processing a substrate to be processed or a resist upper layer film without having a sufficient dry etching durability for processing a substrate to be processed since the silicon middle layer film usually has a film thickness equal to or less than that of the resist upper layer film. The pattern can be transferred to the organic under layer film that has sufficient dry etching durability for substrate processing by transferring the pattern to the organic under layer film by dry etching with an oxygen base or hydrogen base gas plasma using the silicon middle layer film having the pattern transferred thereon as a dry etching mask. This organic under layer film pattern having the pattern transferred thereon can be transferred to a substrate by dry etching by using a fluorine base gas or a chlorine base gas.

On the other hand, the attempt to produce smaller pattern sizes in production processes of semiconductor devices is approaching the inherent limit due to the wavelength of a light source for photolithography. Accordingly, higher integration of semiconductor devices have been investigated recently without depending on smaller pattern sizes. In one of these methods, semiconductor devices with complicated structures have been investigated including a multi gate structure and a gate all-around, and a part of them have been put to practical use already. When these structures are formed by a multilayer resist process, it is possible to apply an organic film material that is capable of planarization by gap filling a minute pattern formed on a substrate to be processed such as a hole, a trench, and a fin with the organic film material without a void, or planarization by filling a step or a pattern dense portion and no pattern region with the organic film material. Such an organic film material is used for forming a planar organic under layer film surface on a stepped substrate to decrease fluctuation of a film thickness of a silicon middle layer film or a resist upper layer film formed thereon, thereby making it possible to avoid the deterioration of depth of focus in photolithography or a margin in the subsequent processing step of a substrate to be processed. This makes it possible to produce semiconductor devices in good yield. On the other hand, it is difficult to produce semiconductor devices in a good yield by a single layer resist process since it requires an upper layer resist film to have thicker film thickness for gap filling a stepped or patterned substrate to be processed, thereby causing lower tolerance for pattern forming in exposure such as pattern collapse after exposure and development as well as degradation of a pattern profile due to reflection from a substrate in exposure.

As a method for next-generation semiconductor devices to achieve higher processing speed, investigations have been undertaken on new materials that have high electron mobility using strained silicon and gallium-arsenic etc. or fine materials such as an ultrathin film polysilicon whose thickness is controlled at the angstrom level. When such a new fine material is applied to a substrate to be processed, however, the material can be corroded with oxygen in air atmosphere under conditions in forming a planar film using the organic under layer film material as described above, for example, the film forming conditions of 300° C. or more in air atmosphere. This risks the semiconductor device to fail to attain higher processing speed as it is designed, and fail to attain the yield that can be managed as industrial manufacturing. Accordingly, an organic under layer material that can be formed in an inert gas is demanded in order to avoid lowering of the yield due to corrosion of a substrate with air atmosphere under the higher temperature conditions.

As a material for forming an organic film for a multilayer resist process, condensation resins have been known including a phenolic or naphtholic compound using a carbonyl compound such as ketones and aldehydes or aromatic alcohols as a condensation agent. Illustrative examples thereof include fluorene bisphenol novolak resins described in Patent Literature 1, bisphenol compounds and novolak resins thereof described in Patent Literature 2, novolak resins of adamantanephenol compounds described in Patent Literature 3, and bisnaphthol compounds and novolak resins thereof described in Patent Literature 4. These materials are formed into a film that has solvent resistance to the coating film material used in the subsequent step by crosslinking thereof with a methylol compound as a crosslinking agent or curing function due to crosslinking reaction including oxidation of the aromatic ring at the α-position by an effect of oxygen in air atmosphere, followed by condensation.

Additionally, Patent Literatures 5 to 10 have been known as examples of each material in which a triple bond is used as a group for intermolecular crosslinking of a curable resin. For these materials, however, the actual curing conditions in an inert gas is not exemplified. There is no information on forming the cured film of these materials in an inert gas or fluctuation of film thicknesses due to thermal decomposition under high temperature conditions.

CITATION LIST

Patent Literature

PATENT LITERATURE 1: Japanese Patent Laid-Open Publication (Kokai) No. 2005-128509
PATENT LITERATURE 2: Japanese Patent Laid-Open Publication (Kokai) No. 2006-293298
PATENT LITERATURE 3: Japanese Patent Laid-Open Publication (Kokai) No. 2006-285095
PATENT LITERATURE 4: Japanese Patent Laid-Open Publication (Kokai) No. 2010-122656
PATENT LITERATURE 5: Japanese Patent Laid-Open Publication (Kokai) No. 2010-181605
PATENT LITERATURE 6: International Patent Laid-Open Publication No. WO 2014-208324
PATENT LITERATURE 7: Japanese Patent Laid-Open Publication (Kokai) No. 2012-215842
PATENT LITERATURE 8: Japanese Patent Laid-Open Publication (Kokai) No. 2016-044272
PATENT LITERATURE 9: Japanese Patent Laid-Open Publication (Kokai) No. 2016-060886
PATENT LITERATURE 10: Japanese Patent Laid-Open Publication (Kokai) No. 2017-119671

SUMMARY OF INVENTION

Technical Problem

The present invention was accomplished in view of the above-described problems. It is an object of the present invention to provide a compound that is capable of curing under the film forming conditions that is not only in air but also in an inert gas without forming volatile byproducts to form an organic under layer film that has good dry etching durability during substrate processing, excellent heat resistance and favorable characteristics of gap filling and planarizing a pattern formed on a substrate; a method for manufacturing the compound, and a composition for forming an organic film using the compound.

Solution to Problem

To solve the above problems, the present invention provides a compound comprising two or more structures shown by the following general formula (1-1) in the molecule,

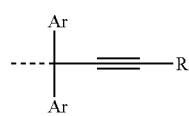

(1-1)

wherein each "Ar" independently represents an aromatic ring optionally having a substituent or an aromatic ring that contains at least one nitrogen atom and/or sulfur atom optionally having a substituent, and two Ars are optionally bonded with each other to form a ring structure; a broken line represents a bond with Y; Y represents a divalent or trivalent organic group having 6 to 30 carbon atoms that contains an aromatic ring optionally having a substituent or a heteroaromatic ring optionally having a substituent, the bonds of which are located in a structure of the aromatic ring or the heteroaromatic ring; R represents a hydrogen atom or a monovalent group having 1 to 68 carbon atoms.

The compound like this is capable of curing under the film forming conditions that is not only in air but also in an inert gas without forming byproducts to form an organic under layer film that has good dry etching durability in substrate processing not only excels in heat resistance and characteristics of gap filling and planarizing a pattern formed on a substrate.

In this case, the above compound is preferably a compound that has units shown by the following general formulae (2-1) and (2-2),

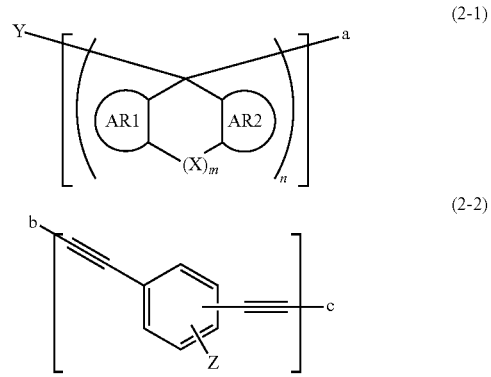

wherein AR1 and AR2 each represent a benzene ring, a pyridine ring, or a naphthalene ring optionally having an alkoxy group, an alkenyloxy group, an alkynyloxy group, or an aryloxy group having 1 to 30 carbon atoms; "m" is 0 or 1; when m=0, the aromatic rings of AR1 and AR2 do not form a bridged structure with each other, when m=1, AR1 and AR2 form a bridged structure in which the aromatic rings of AR1 and AR2 are bonded with each other through X; X represents a single bond or any of groups shown by the following formulae (3);

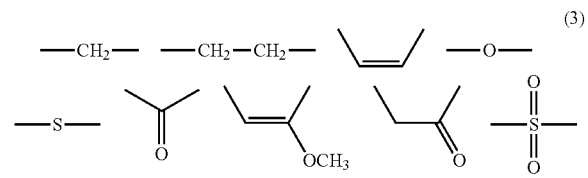

"n" is 2 or 3; Y represents the same meanings as defined above; Z represents a hydrogen atom or a monovalent organic group having 1 to 30 carbon atoms; "a" bonds with "b", and "c" represents a hydrogen atom or a monovalent organic group having 1 to 30 carbon atoms or bonds with "a".

These compounds having units shown by the general formulae (2-1) and (2-2) are preferably since they are more securely cured under the film forming conditions that is in an inert gas, and are particularly excellent in heat resistance as well as characteristics of gap filling and planarizing a pattern formed on a substrate.

The present invention also provides a method for manufacturing the compound having two or more structures shown by the following general formula (1-1) in the molecule, comprising the steps of:

manufacturing a diol and/or triol by a reaction shown by the following formula (4-1),

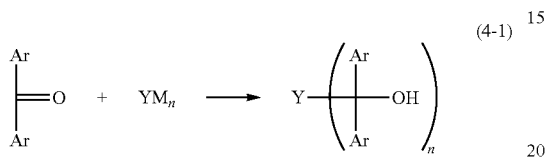
(4-1)

wherein Ar and Y have the same meanings as defined above; "n" is 2 or 3; M represents Li or Mg-Hal, and Hal represents Cl, Br, or I;

manufacturing a dihalogenated compound and/or a trihalogenated compound by a reaction shown by the following formula (4-2),

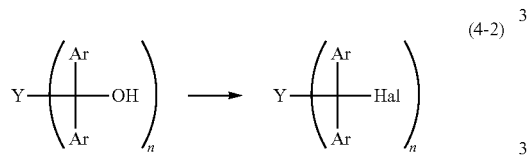
(4-2)

wherein Ar, Y, Hal, and "n" have the same meanings as defined above; and manufacturing a compound by a reaction shown by the following formula (4-3),

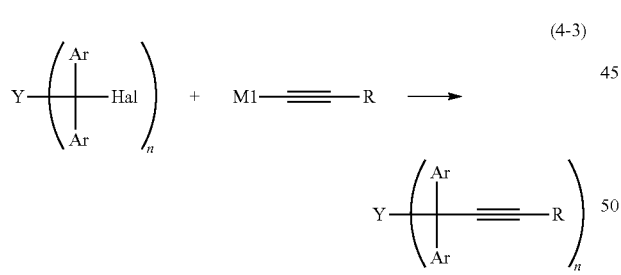
(4-3)

wherein Ar, Y, "n", Hal, and R have the same meanings as defined above; and M1 represents Li or Mg-Hal.

The method for manufacturing the compound like this makes it possible to manufacture the compounds without using transition metal, which causes a defect in dry etching process in producing a semiconductor device, as a catalyst in forming a skeleton of the compound. Accordingly, the dry etching can be performed without generating a defect due to transition metal, thereby making it possible to produce semiconductor devices in a good yield.

The present invention also provides a method for manufacturing the compound having units shown by the general formulae (2-1) and (2-2), comprising the steps of:

manufacturing a diol and/or triol by a reaction shown by the following formula (5-1),

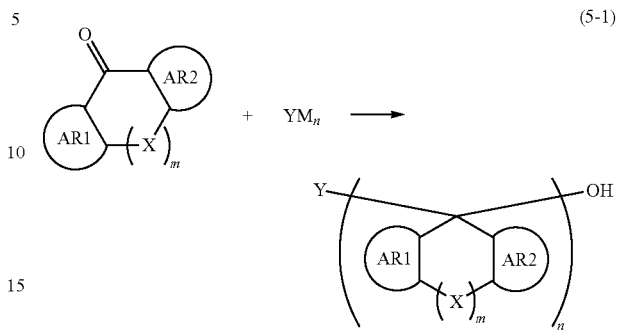
(5-1)

wherein AR1, AR2, X, Y, "m", and "n" have the same meanings as defined above; M represents Li or Mg-Hal, and Hal represents Cl, Br, or I;

manufacturing a dihalogenated compound and/or a trihalogenated compound by a reaction shown by the following formula (5-2),

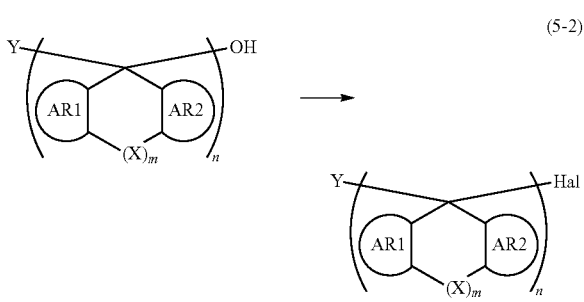
(5-2)

wherein AR1, AR2, X, Y, "m", "n", and Hal have the same meanings as defined above; and manufacturing a polymer by a reaction shown by the following formula (5-3),

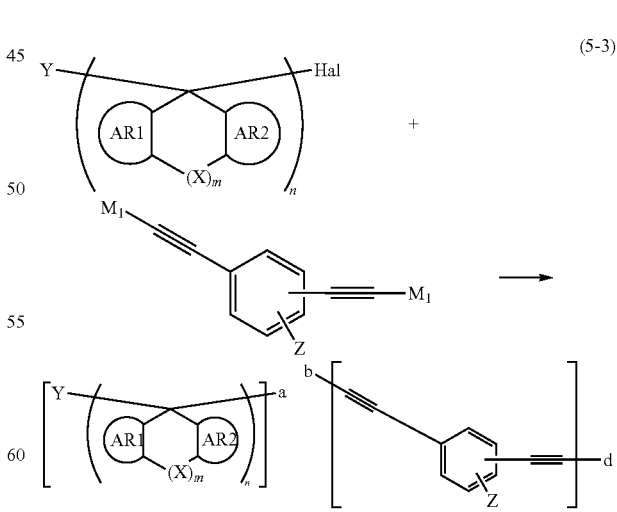
(5-3)

wherein AR1, AR2, X, Y, Z, "n", "m", and Hal have the same meanings as defined above; M1 represents Li or Mg-Hal; "a" bonds with "b", and "d" represents a hydrogen atom or bonds with "a".

The present invention also provides a method for manufacturing the compound having units shown by the general formulae (2-1) and (2-2), comprising the steps of:

manufacturing a diol and/or triol by a reaction shown by the following formula (5-1),

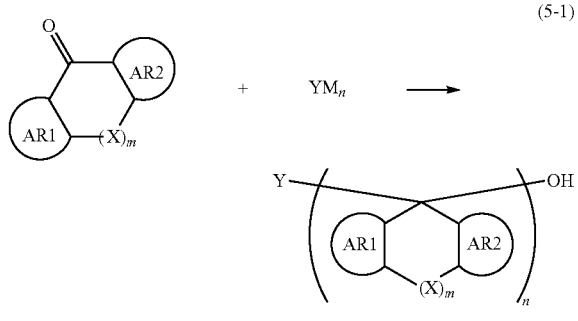

(5-1)

wherein AR1, AR2, X, Y, "m", and "n" have the same meanings as defined above; M represents Li or Mg-Hal, and Hal represents Cl, Br, or I;

manufacturing a dihalogenated compound and/or a trihalogenated compound by a reaction shown by the following formula (5-2),

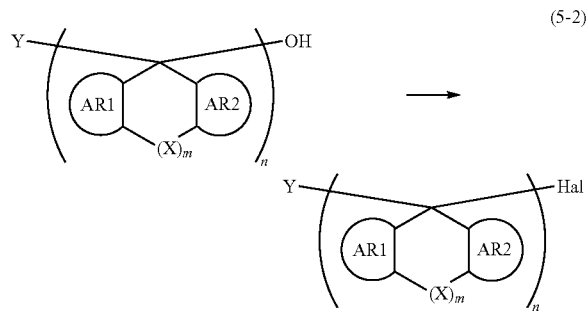

(5-2)

wherein AR1, AR2, X, Y, "m", "n", and Hal have the same meanings as defined above;

manufacturing a polymer by a reaction shown by the following formula (5-4), followed by introducing a substituent to a terminal of the polymer by a reaction shown by the following formula (5-5), wherein AR1, AR2, X, Y, Z, "m", "n", and Hal have the same meanings as defined above; M1 represents Li or Mg-Hal; "a" bonds with "b"; "e" represents M1 or bonds with "a"; and "f" represents a monovalent organic group having 1 to 30 carbon atoms or bonds with "a".

As a method for manufacturing the compound having units shown by the general formulae (2-1) and (2-2), these methods are exemplified.

The present invention also provides a composition for forming an organic film, comprising (A) a compound having two or more structures shown by the following general formula (1-1) in the molecule dissolved in an organic solvent (B),

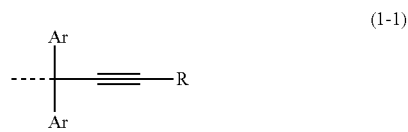

(1-1)

wherein each "Ar" independently represents an aromatic ring optionally having a substituent or an aromatic ring that contains at least one nitrogen atom and/or sulfur atom optionally having a substituent, and two Ars are optionally bonded with each other to form a ring structure; a broken line represents a bond with Y; Y represents a divalent or trivalent organic group having 6 to 30 carbon atoms that contains an aromatic ring optionally having a substituent or a heteroaromatic ring optionally having a substituent, the bonds of which are located in a structure of the aromatic ring or the heteroaromatic ring; R represents a hydrogen atom or a monovalent group having 1 to 68 carbon atoms.

The inventive composition for forming an organic film is capable of forming an organic film that has higher heat resistance, higher dry etching durability, and higher gap filling/planarizing characteristics.

In this case, it is preferable that the above compound (A) be a compound that has units shown by the following general formulae (2-1) and (2-2),

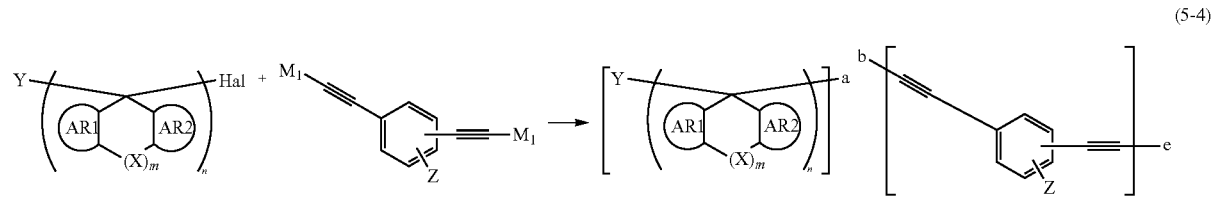

(5-4)

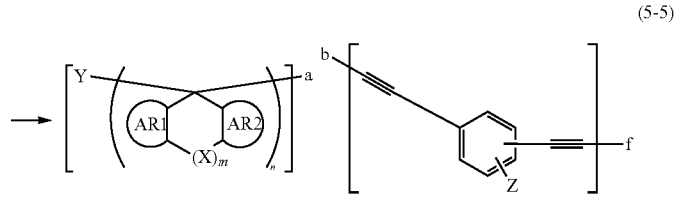

(5-5)

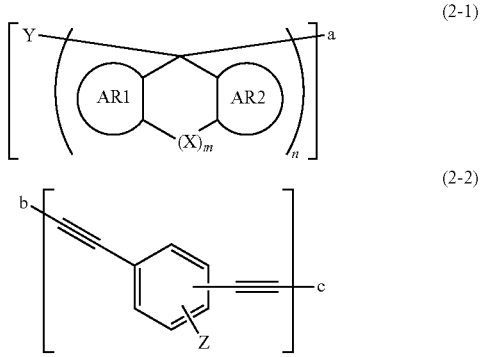

(2-1)

(2-2)

wherein AR1 and AR2 each represent a benzene ring, a pyridine ring, or a naphthalene ring optionally having an alkoxy group, an alkenyloxy group, an alkynyloxy group, or an aryloxy group having 1 to 30 carbon atoms; "m" is 0 or 1; when m=0, the aromatic rings of AR1 and AR2 do not form a bridged structure with each other, when m=1, AR1 and AR2 form a bridged structure in which the aromatic rings of AR1 and AR2 are bonded with each other through X; X represents a single bond or any of groups shown by the following formulae (3);

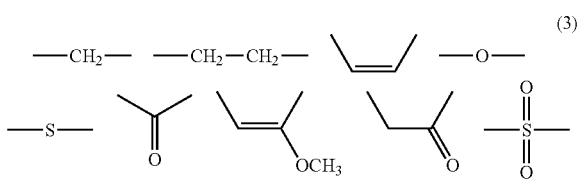

(3)

"n" is 2 or 3; Y represents the same meanings as defined above; Z represents a hydrogen atom or a monovalent organic group having 1 to 30 carbon atoms; "a" bonds with "b", and "c" represents a hydrogen atom or a monovalent organic group having 1 to 30 carbon atoms or bonds with "a".

The composition for forming an organic film containing the compound is more securely cured under the film forming conditions that is in an inert gas, and is capable of forming an organic under layer film that is excellent in heat resistance as well as characteristics of gap filling and planarizing a pattern formed on a substrate.

In this case, the component (A) preferably has a weight-average molecular weight between 500 and 20,000 Da.

With such a molecular weight, the compound is allowed to have more favorable thermal fluidity, and enables the composition containing the compound to form an organic film capable of not only favorably gap filling a fine structure formed on a substrate, but also planarizing the whole substrate.

In this case, the composition for forming an organic film preferably contains at least one of (C) an acid generator, (D) a surfactant, (E) a cross-linking agent, and (F) a plasticizer.

The inventive composition for forming an organic film can contain at least one of the components (C) to (F) in accordance with the object.

Advantageous Effects of Invention

As described above, the inventive compound is a compound that is curable in film forming in an inert gas, which prevents a substrate from corrosion, without forming volatile byproducts, and is useful for forming an organic under layer film that has higher gap filling and planarizing characteristics. The composition for forming an organic film containing this compound is a material capable of forming an organic film that has excellent gap filling/planarizing characteristics combined with various properties such as heat resistance and etching durability. Accordingly, they are very useful as an organic film material in multilayer resist processes such as a two-layer resist process, a three-layer resist process using a silicon middle layer film, and a four-layer resist process using a silicon middle layer film and an organic bottom antireflective coating as well as a planarization material for producing a semiconductor device. The organic film formed from the inventive composition for forming an organic film is excellent in heat resistance, and is favorably used for patterning without causing fluctuation of the film thicknesses due to thermal decomposition even during CVD (Chemical Vapor Deposition) deposition of hard mask on the organic under layer film.

Additionally, the method for manufacturing the compound makes it possible to form a skeleton of the compound (polymer) without using a transition metal catalyst.

DESCRIPTION OF EMBODIMENTS

Figure 1:
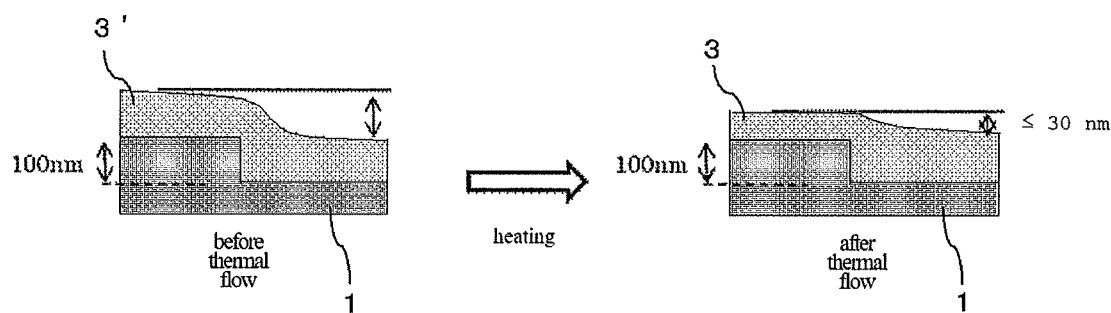
FIG. 1 is an explanatory diagram of the planarizing characteristics in the present invention.

As described above, it has been demanded for an organic under layer film that is curable without forming a volatile byproduct under the film forming conditions in an inert gas, for example, at a temperature of 300° C. or more in order to prevent corrosion of a substrate, and is excellent in characteristics of gap filling and planarizing a pattern formed on a substrate as well as dry etching durability in substrate processing. Additionally, it has been demanded for an organic film that is free from fluctuation of the film thickness due to decomposition even during CVD deposition of a hard mask on the organic under layer film, and it has been desired to develop a compound for forming an organic film to attain these properties.

The forming of an organic under layer film is usually performed such that a compound for forming an organic film is dissolved in an organic solvent to form a composition, which is then applied onto a substrate having semiconductor device structures or wiring formed thereon, followed by baking to form an organic under layer film. The composition forms a coating film in accordance with the shape of a patterned structure on the substrate immediately after application thereof. When the coating film is baked for curing, most of the organic solvent is evaporated, and an organic film is formed on the substrate. The inventors noticed this behavior and have conceived that if the compound for forming an organic film deposited on the substrate has sufficient thermal fluidity, the pattern topography is planarized by thermal flow, thereby making it possible to form a planar film.

In order to provide a material that has high heat resistance and is capable of curing in an inert gas to prevent a substrate from corrosion due to oxygen in air atmosphere, the inventors continued to diligently investigate a structure that realizes such a curing reaction. Thus the present inventors have found that the compound having two or more structures shown by the general formula (1-1), which contains a quarternary carbon having three aromatic substituents and one triple bonding-carbon substituent as intermolecular crosslinking groups, is capable of heat curing during the film forming conditions in either in air or inert atmosphere to show curing properties equal to conventional under layer film materials even in an inert gas without forming volatile byproducts in the curing reaction, and brings higher heat resistance due to the aromatic rings that are introduced effectively. The present inventors have also found that this compound possesses higher gap filling/planarizing characteristics due to the good thermal fluidity to give a composition for forming an organic film with excellent dry etching durability and heat resistance, thus preventing film thickness fluctuation upon exposure to high temperature CVD hard mask formation process; thereby brought the present invention to completion.

Hereinafter, the present invention will be explained in detail, but the present invention is not limited thereto.

<Compound (1)>

The compound of the present invention is a compound having two or more structures shown by the following general formula (1-1) in the molecule (hereinafter, referred to as Compound (1)),

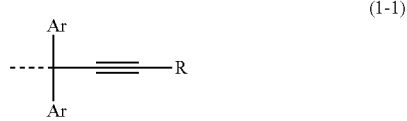

(1-1)

wherein each "Ar" independently represents an aromatic ring that may have a substituent or an aromatic ring that contains at least one nitrogen atom and/or sulfur atom that may have a substituent, and two Ars may be bonded with each other to form a ring structure; the broken line represents a bond with Y; Y represents a divalent or trivalent organic group having 6 to 30 carbon atoms containing an aromatic ring that may have a substituent or a heteroaromatic ring that may have a substituent, the bonds of which are located in a structure of the aromatic ring or the heteroaromatic ring; R represents a hydrogen atom or a monovalent group having 1 to 68 carbon atoms.

Each "Ar" independently represents an aromatic ring optionally having a substituent or an aromatic ring that contains at least one nitrogen atom and/or sulfur atom optionally having a substituent, and two Ars are optionally bonded with each other to form a ring structure. Illustrative examples of the aromatic ring in the "Ar" include a benzene ring, a naphthalene ring, a pyridine ring, and a thiophene ring. The substituent is not particularly limited, but illustrative examples thereof include an alkoxy group, an alkenyloxy group, an alkynyloxy group, and an aryloxy group having 1 to 30 carbon atoms.

Additionally, Y represents a divalent or trivalent organic group having 6 to 30 carbon atoms containing an aromatic ring that may have a substituent or a heteroaromatic ring that may have a substituent, the bonds of which are located in a structure of the aromatic ring or the heteroaromatic ring.

Illustrative examples of the aromatic ring and the heteroaromatic ring in Y include a benzene ring, a naphthalene ring, a pyridine ring, a furan ring, and a thiophene ring. As the substituent, the same as the substituents illustrated as the substituent in Ar are exemplified. Incidentally, the "organic group" in the present invention means a group that contains at least a carbon atom, which may additionally contains a hydrogen atom, and further a nitrogen atom, an oxygen atom, a sulfur atom, or a silicon atom.

R represents a hydrogen atom or a monovalent group having 1 to 68 carbon atoms, and is preferably a hydrogen atom or a group containing a carbon-carbon triple bond(s) and an aromatic ring or a heteroaromatic ring.

The compound of the present invention is specifically a compound that has units shown by the following general formulae (2-1) and (2-2) (hereinafter, referred to as Compound (2)),

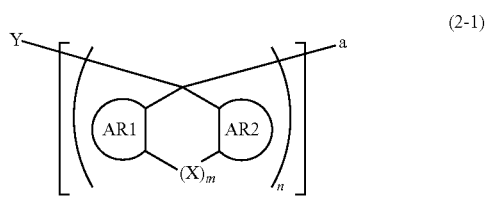

(2-1)

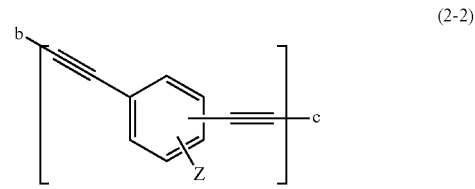

(2-2)

wherein AR1 and AR2 each represent a benzene ring, a pyridine ring, or a naphthalene ring optionally having an alkoxy group, an alkenyloxy group, an alkynyloxy group, or an aryloxy group having 1 to 30 carbon atoms; "m" is 0 or 1; when m=0, the aromatic rings of AR1 and AR2 do not form a bridged structure with each other, when m=1, AR1 and AR2 form a bridged structure in which the aromatic rings of AR1 and AR2 are bonded with each other through X; X represents a single bond or any of groups shown by the following formulae (3);

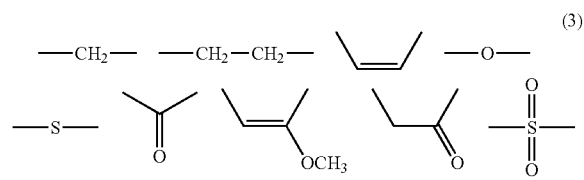

(3)

"n" is 2 or 3; Y has the same meaning as defined above; Z represents a hydrogen atom or a monovalent organic group having 1 to 30 carbon atoms; "a" and "b" represent bonding sites that are bonded with each other, and "c" represents a hydrogen atom, a monovalent organic group having 1 to 30 carbon atoms, or a bonding site that is bonded with "a".

Illustrative examples of the Compound (1) and the Compound (2) include the following structures, but are not limited these structures.

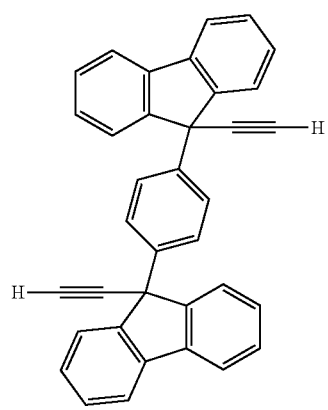
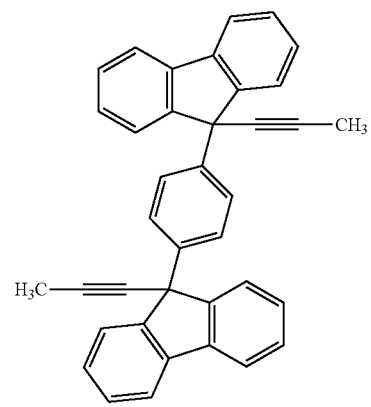
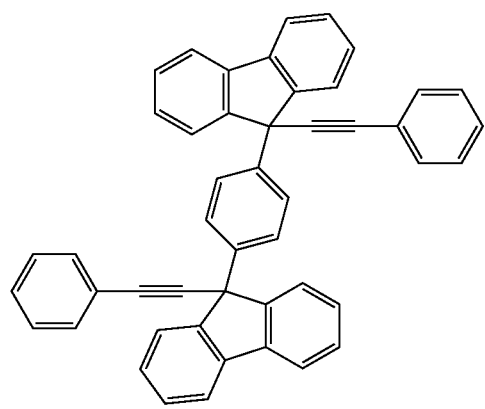
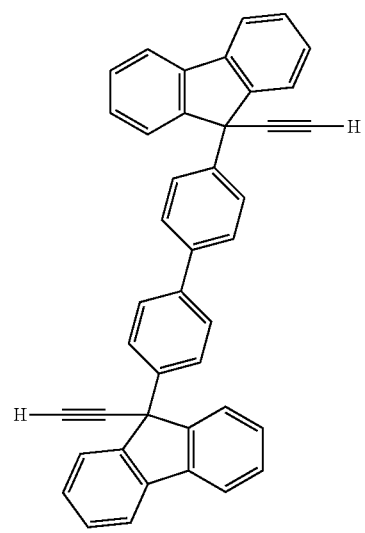
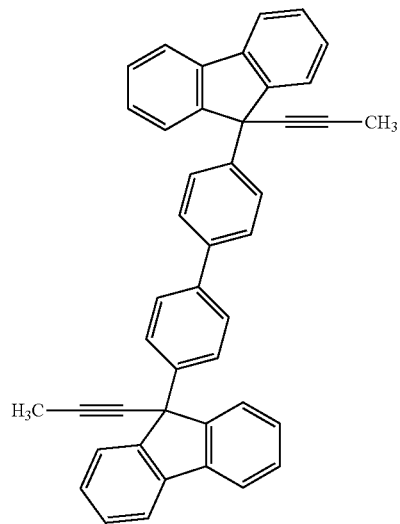
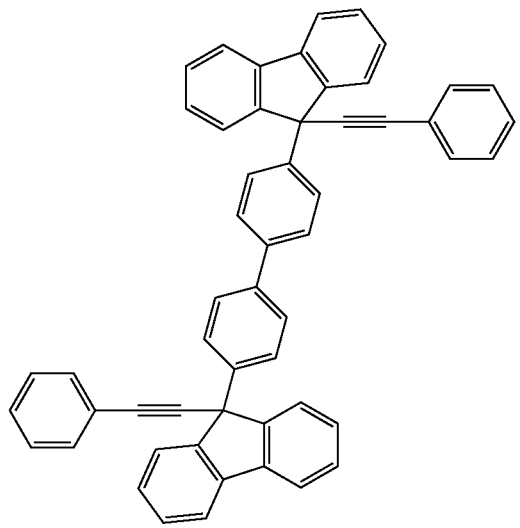

-continued
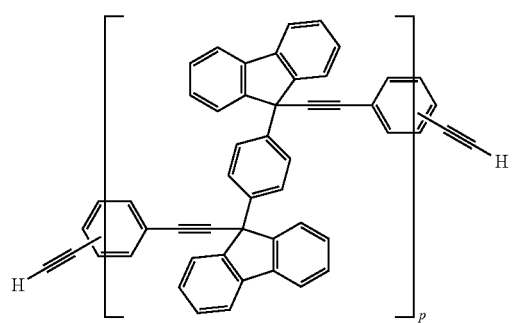
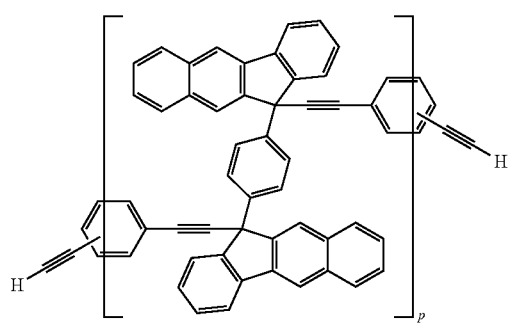
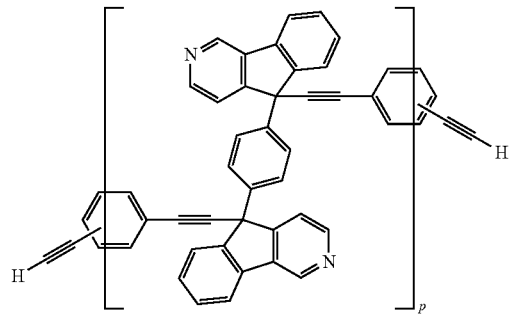
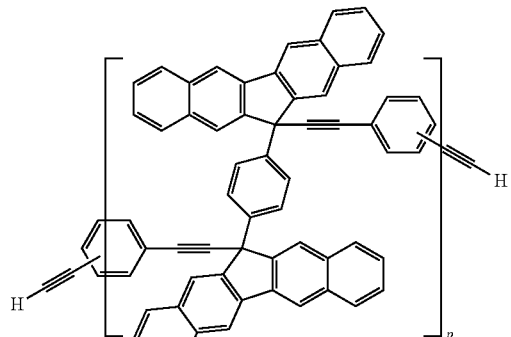
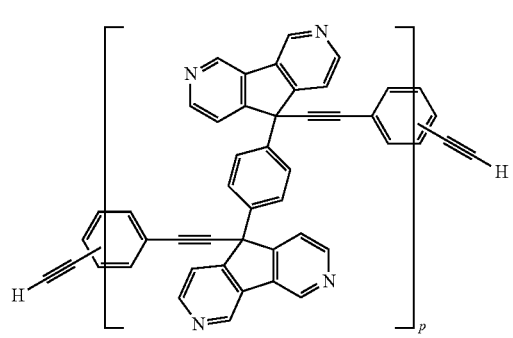
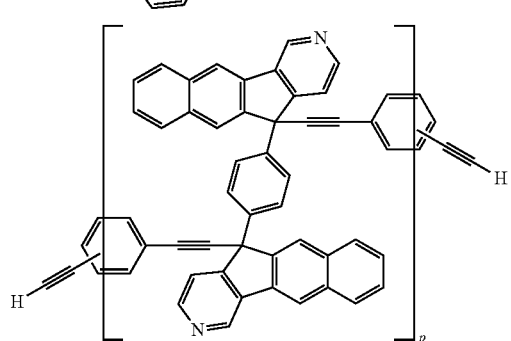
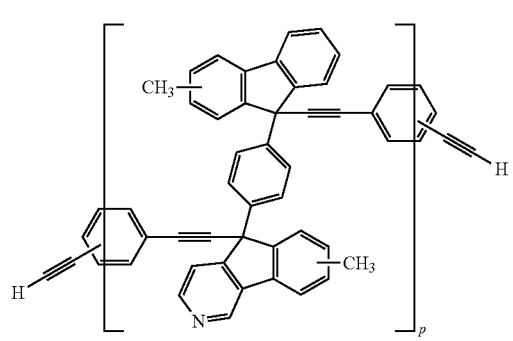
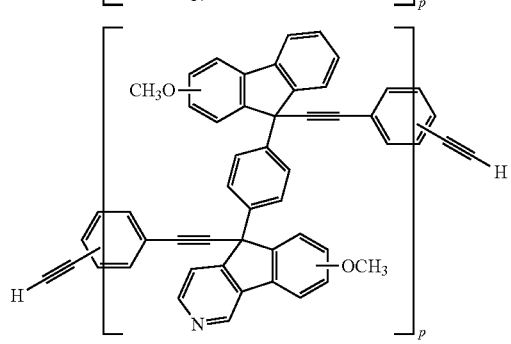
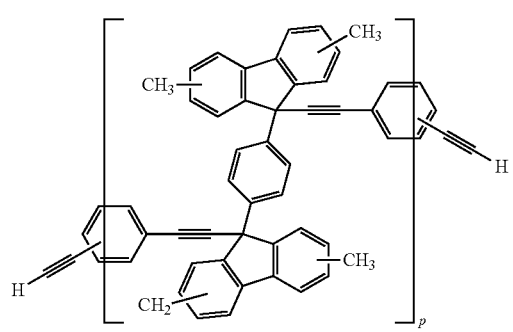
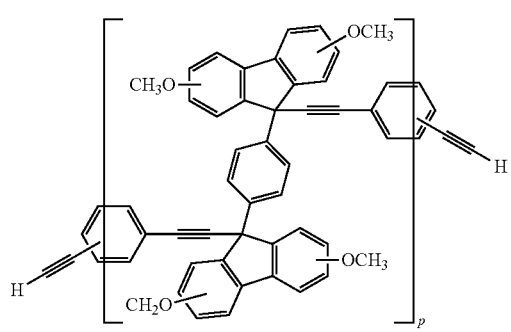

-continued
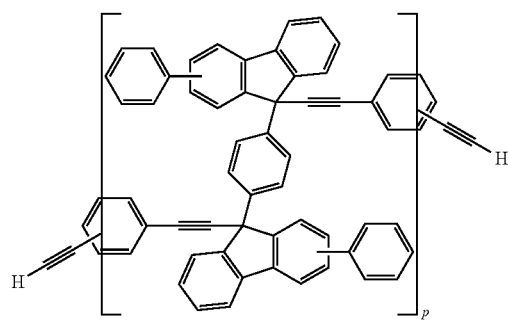
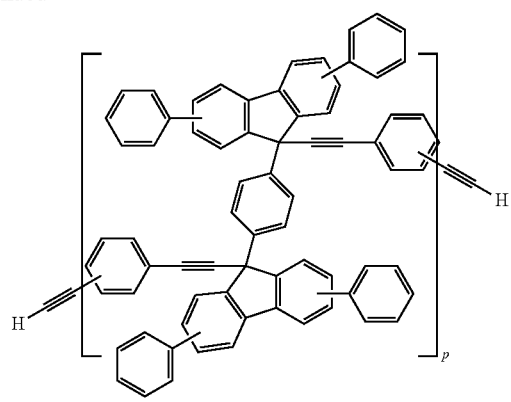
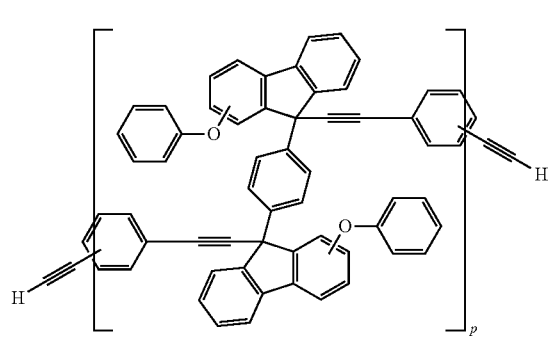
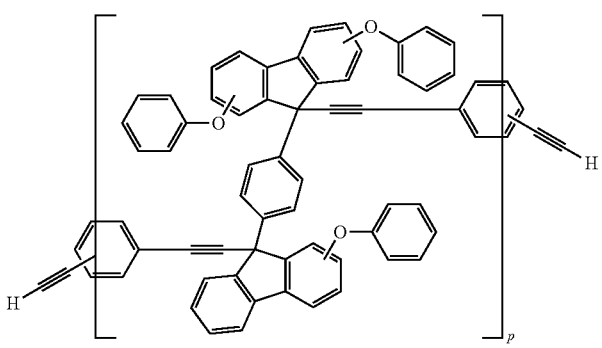
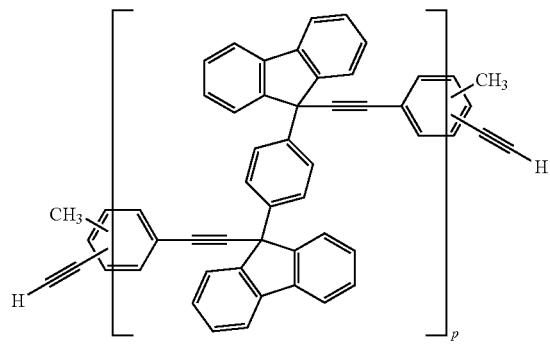
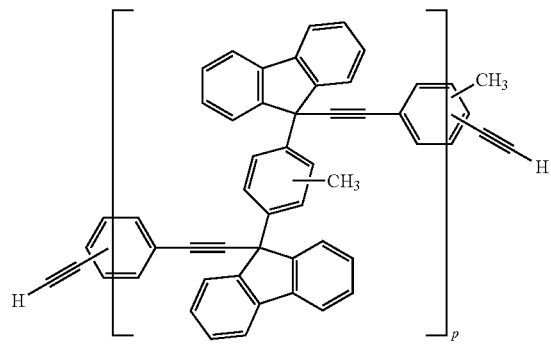
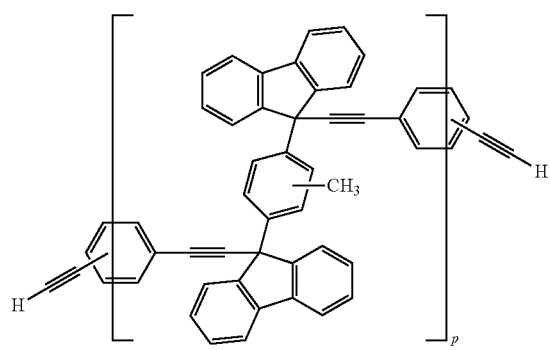
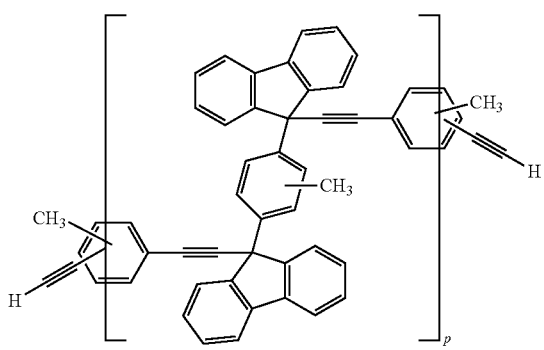

-continued
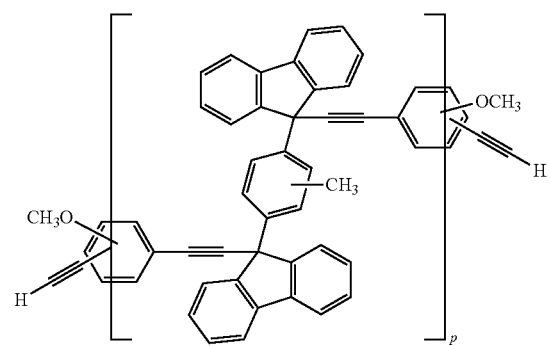
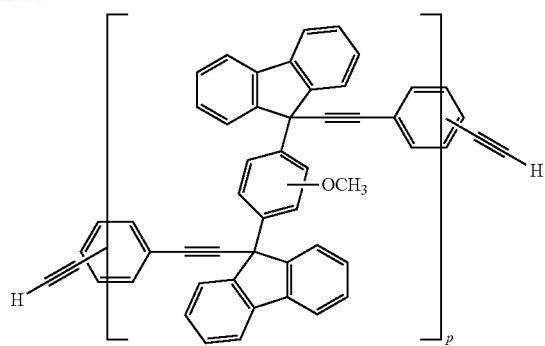
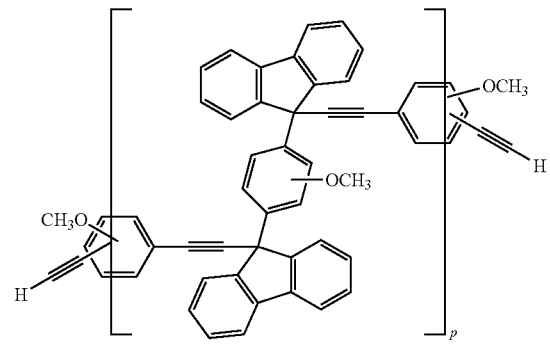
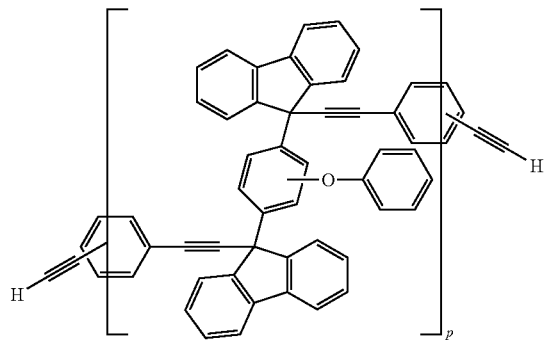
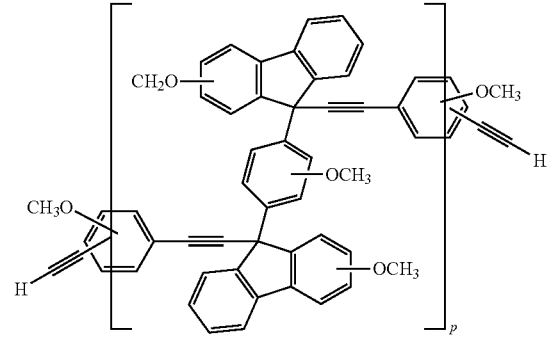
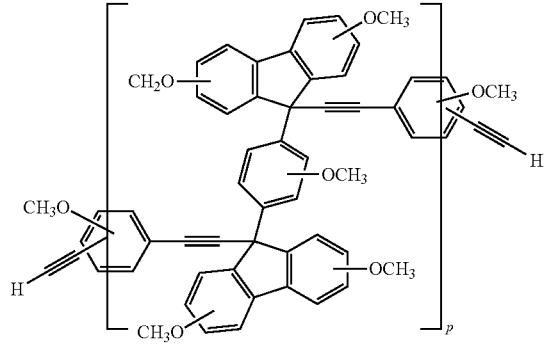
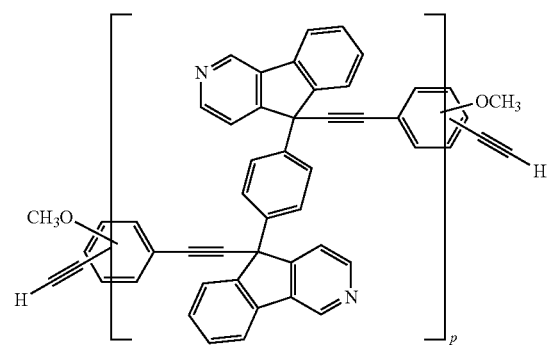
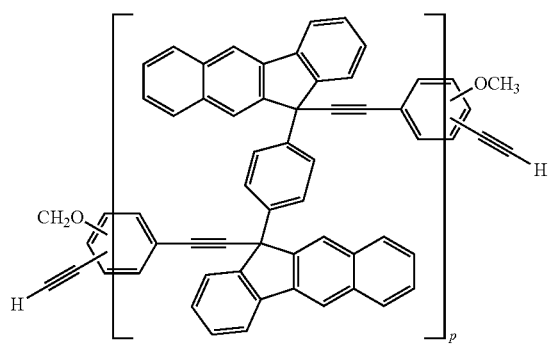
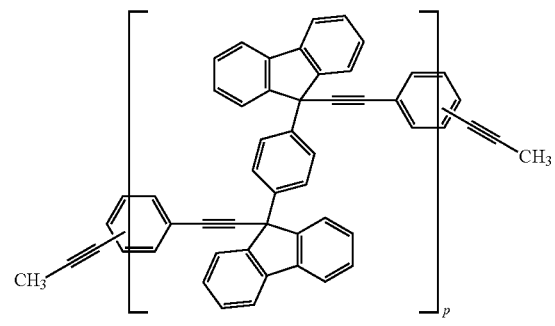
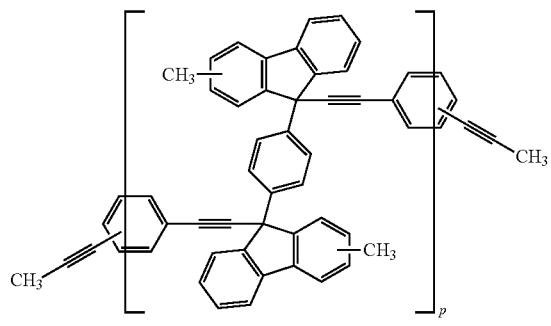

-continued
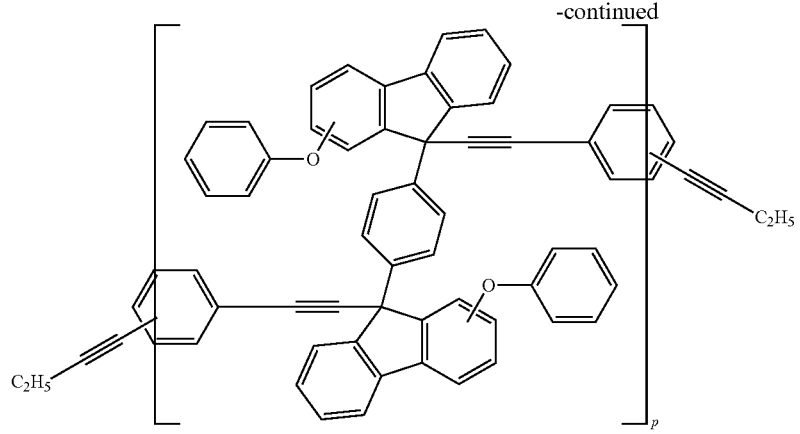
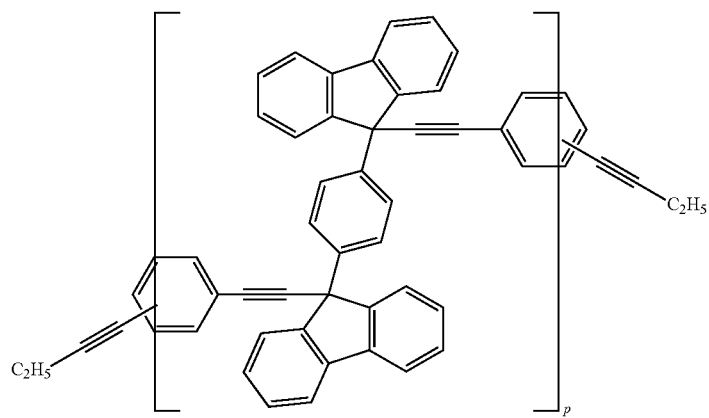
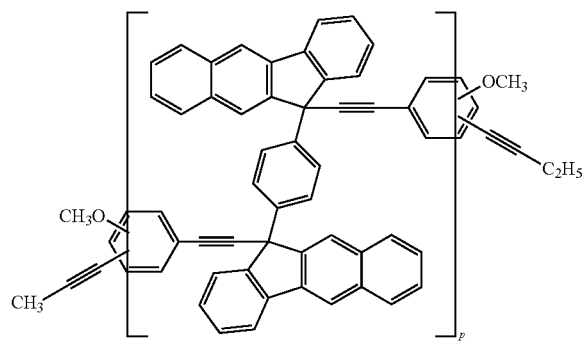
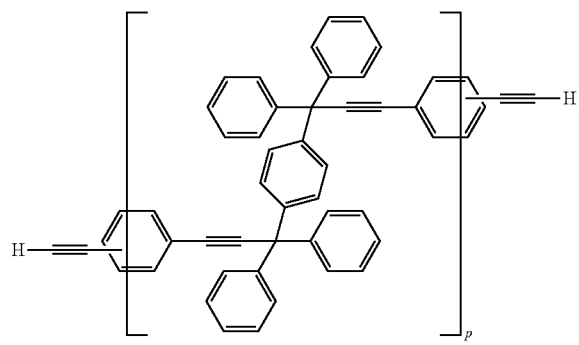
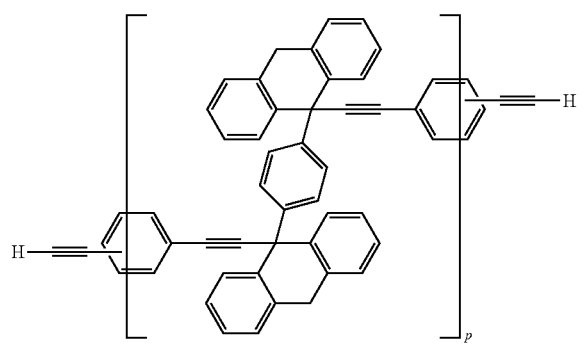
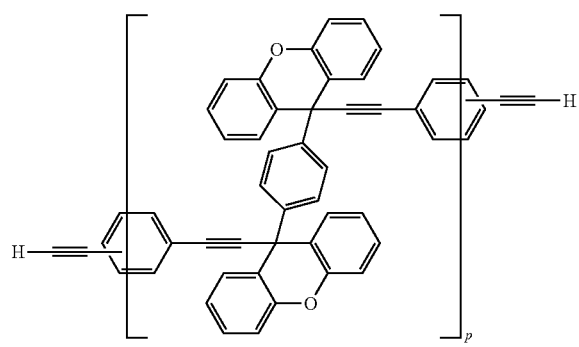

-continued
| 23 | 24 |
|---|---|
| 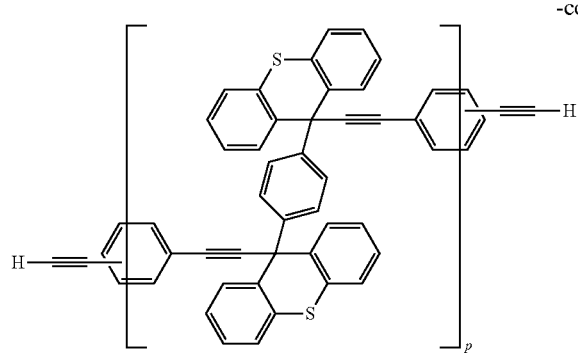 | 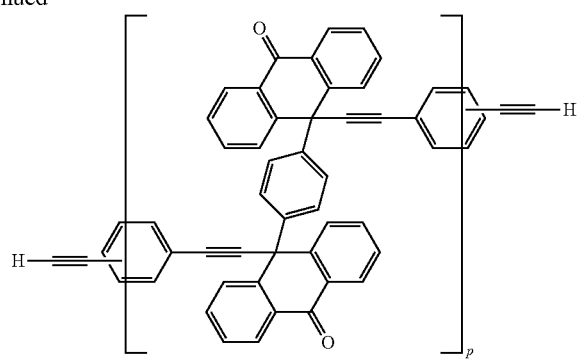 |
| 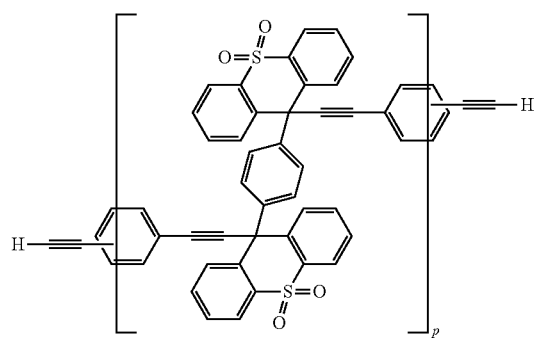 | 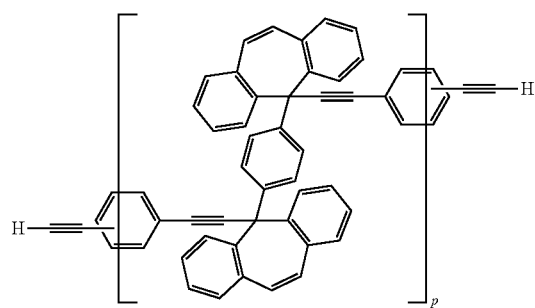 |
| 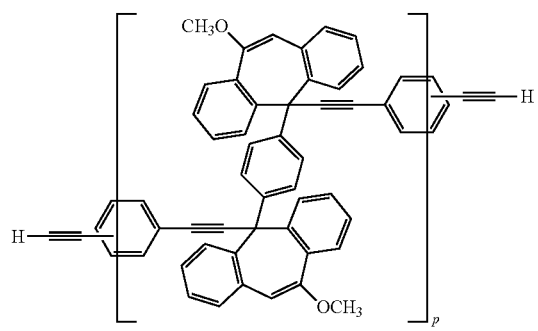 | 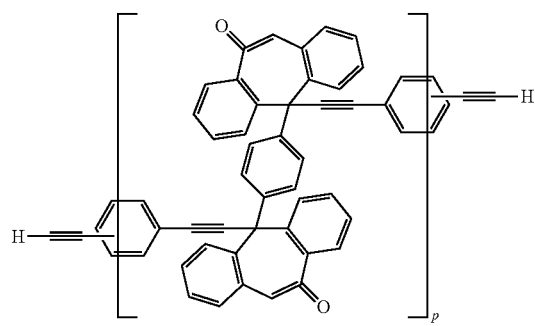 |
| 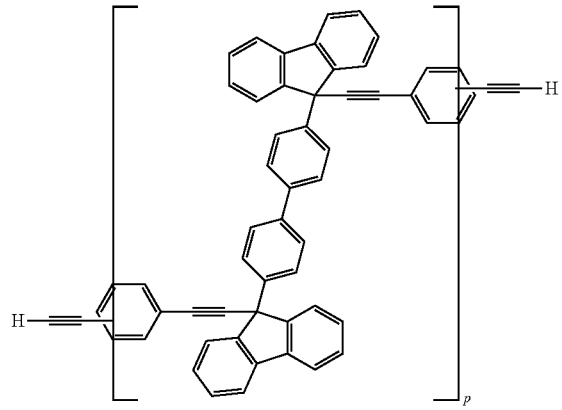 | 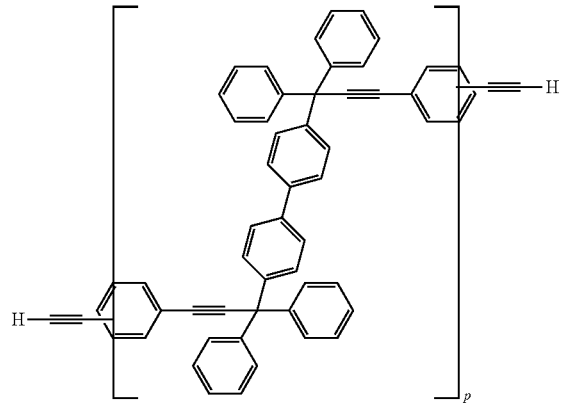 |

-continued
25
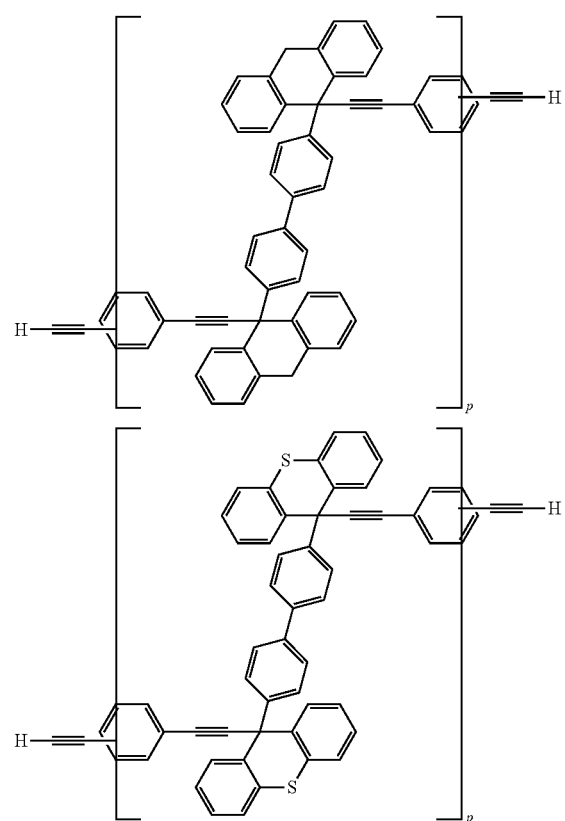
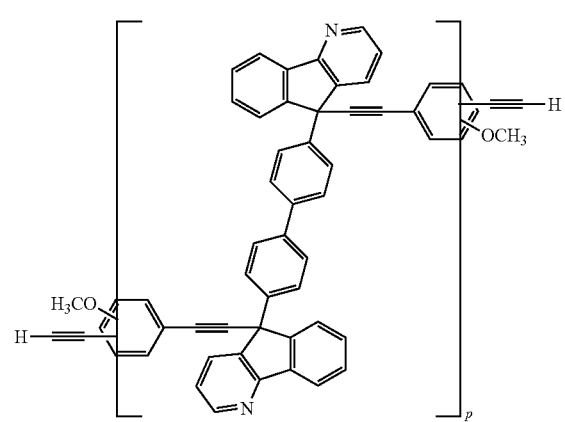
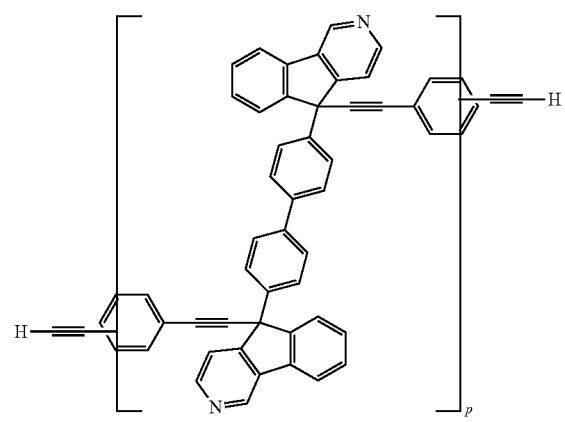
26
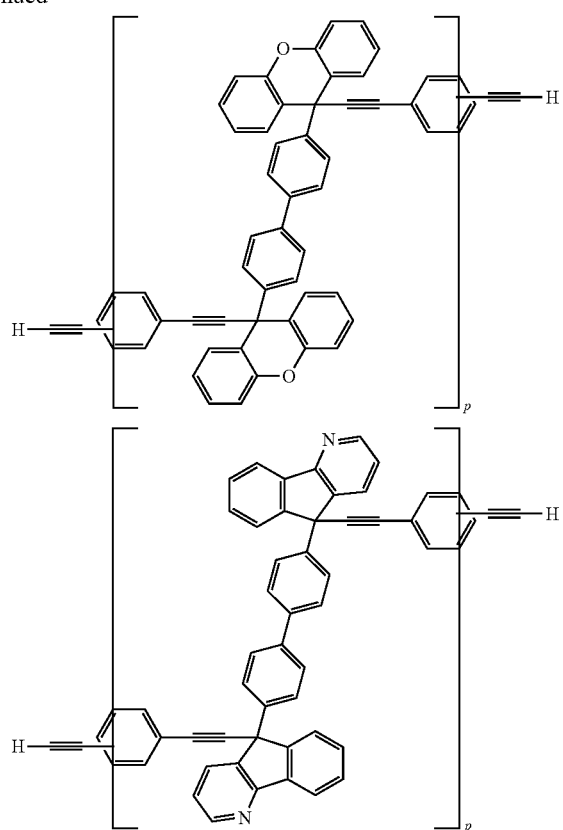
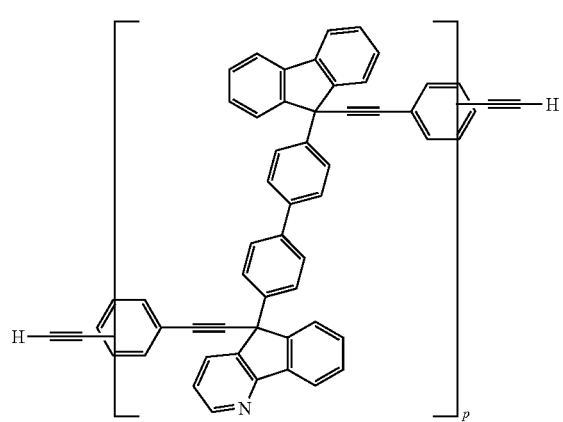
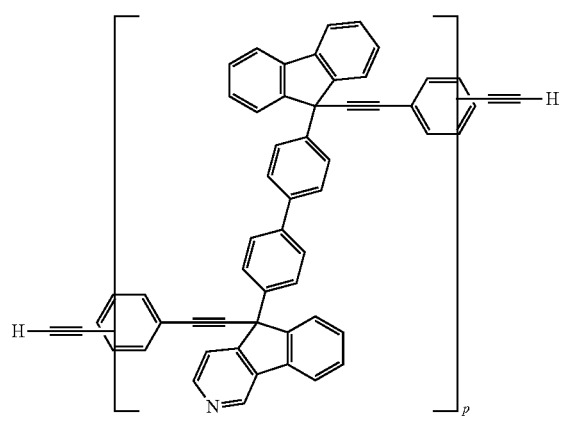

-continued
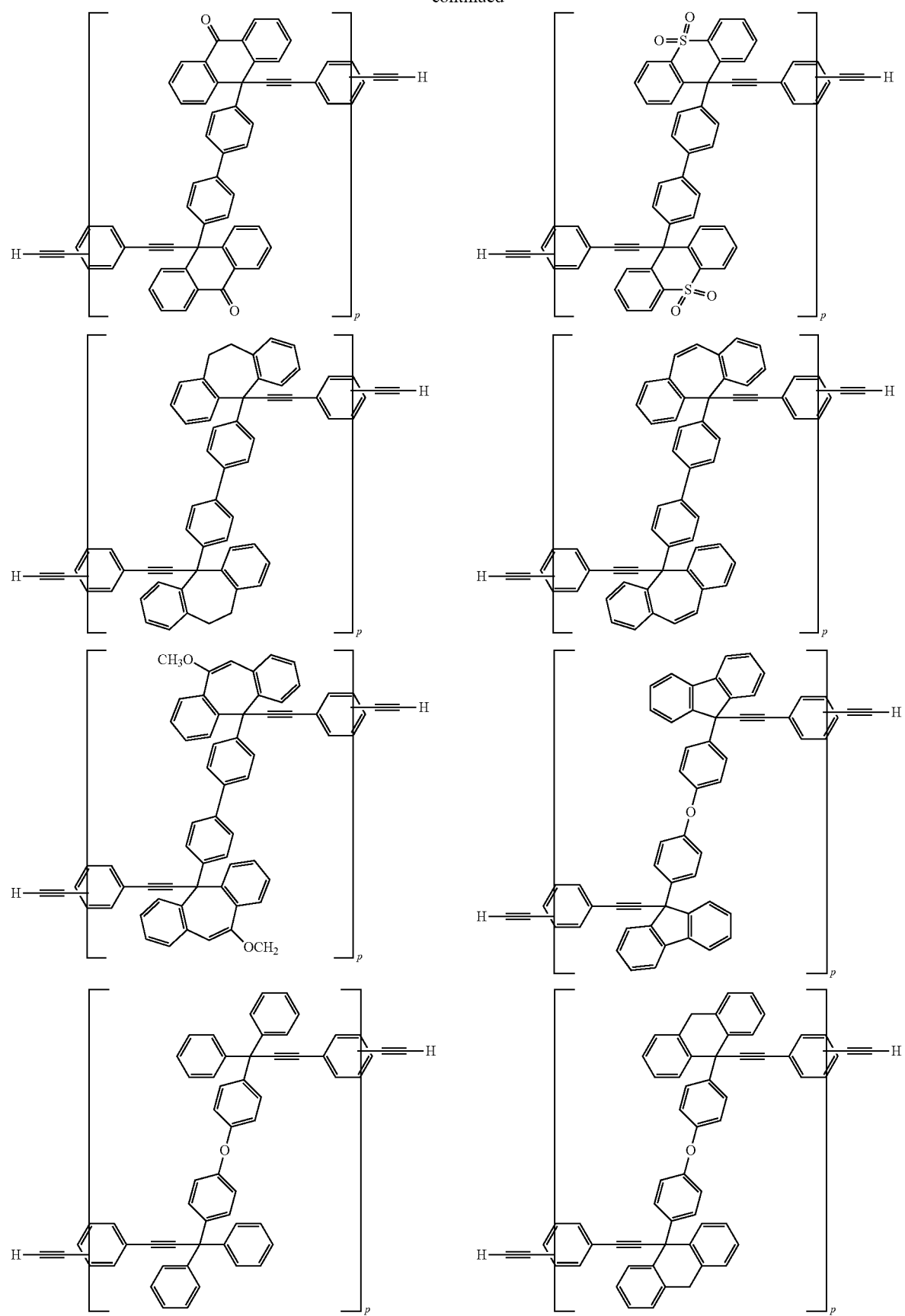

29
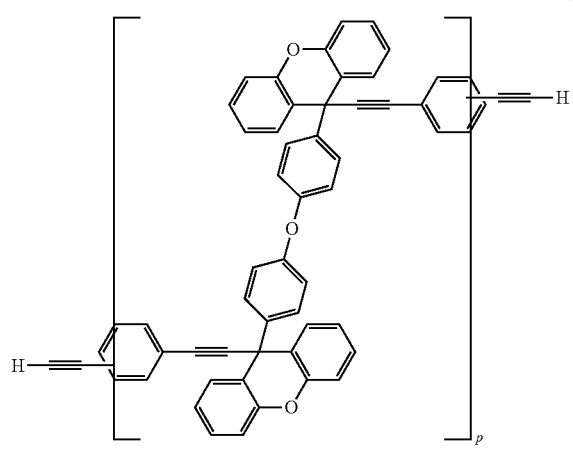
30
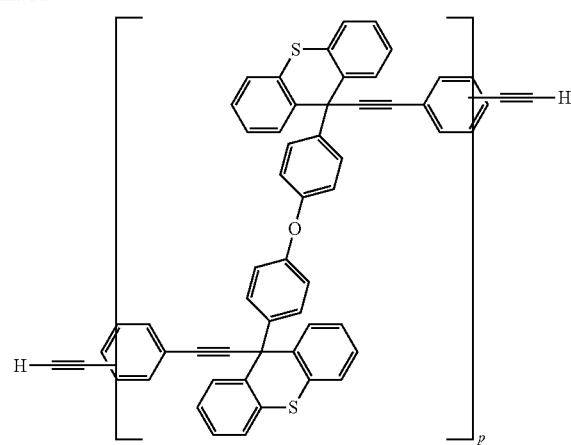
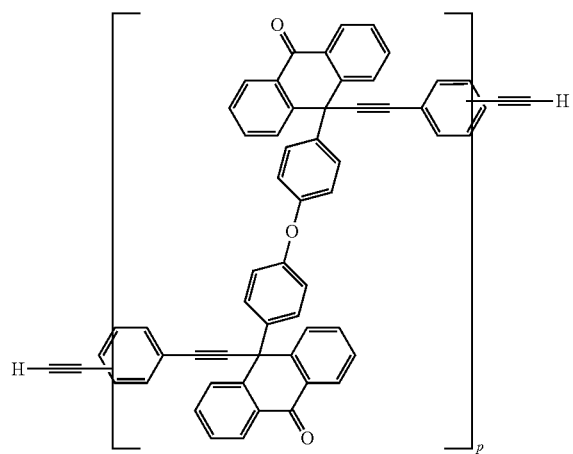
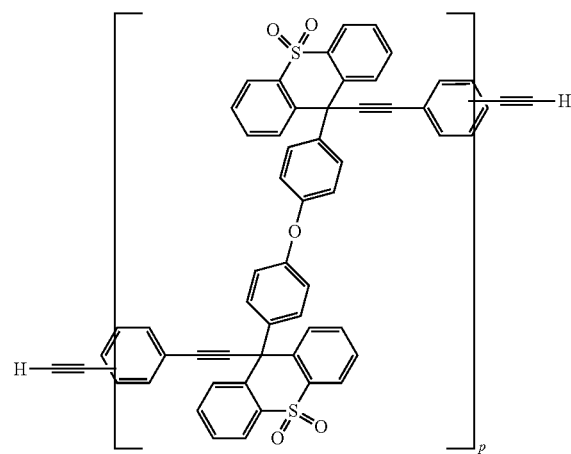
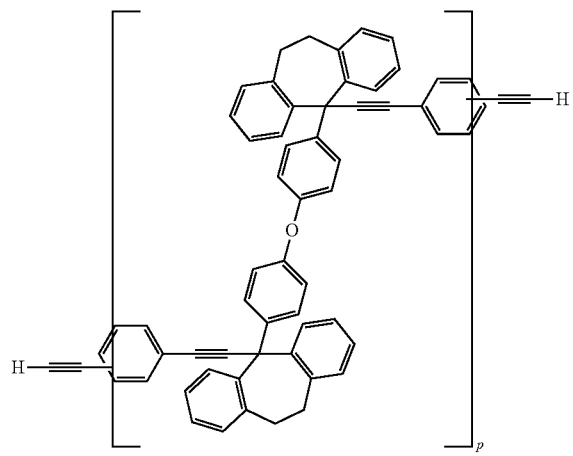
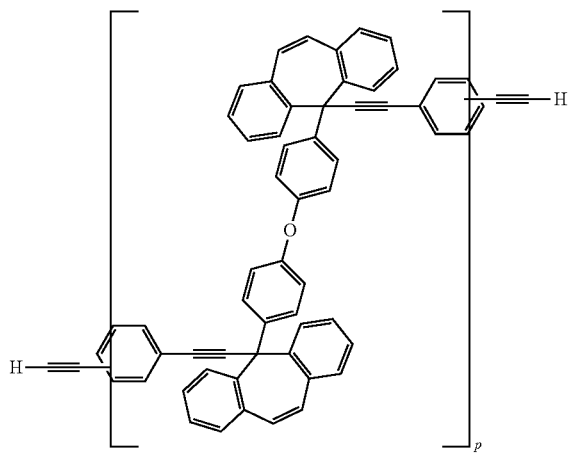

-continued
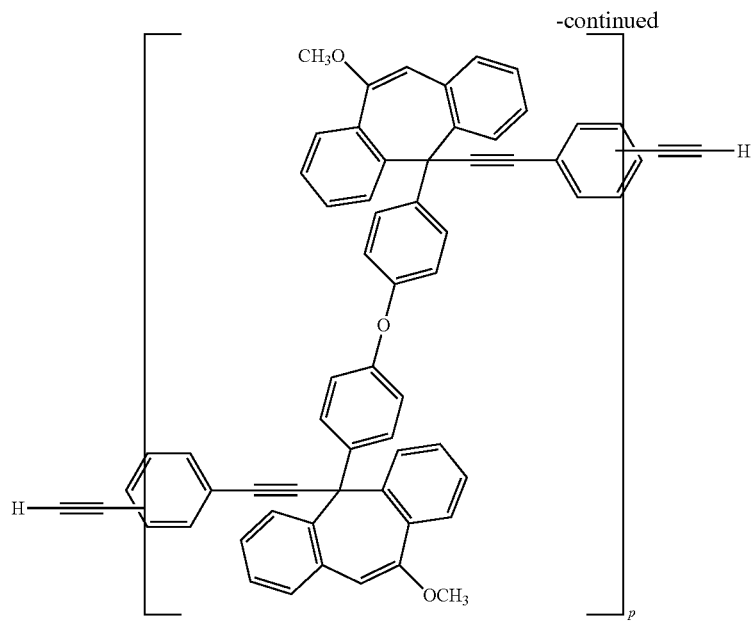
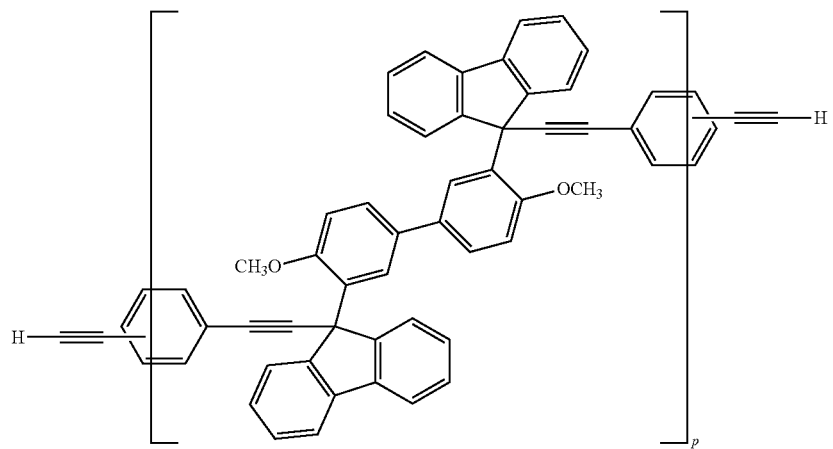
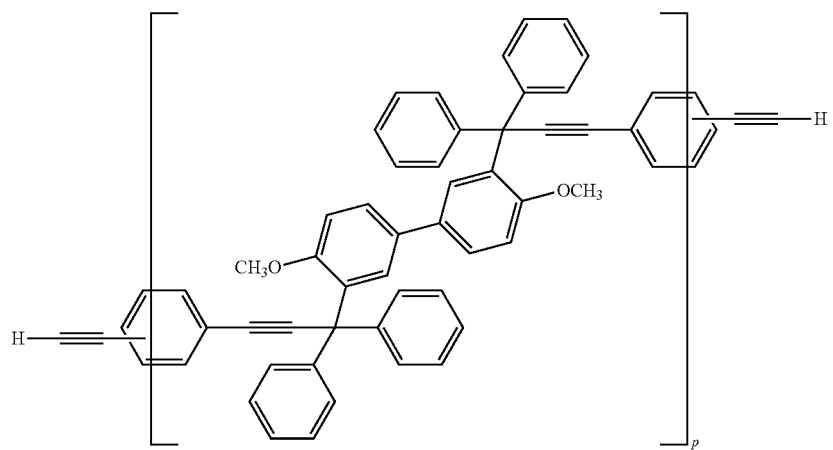

-continued
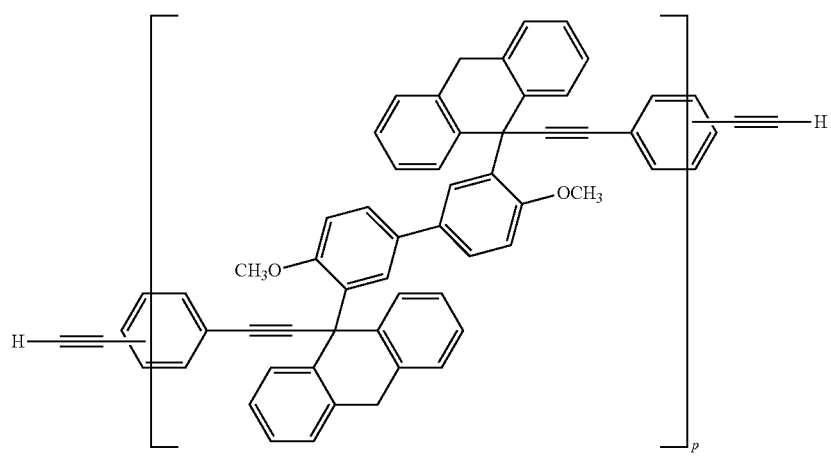
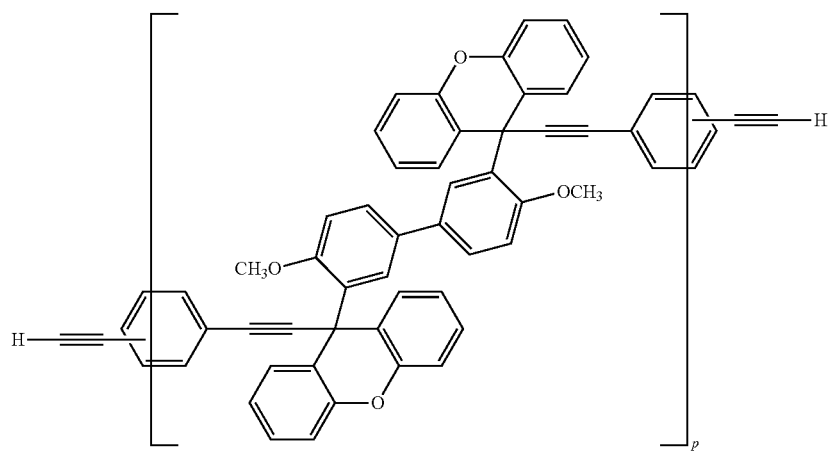
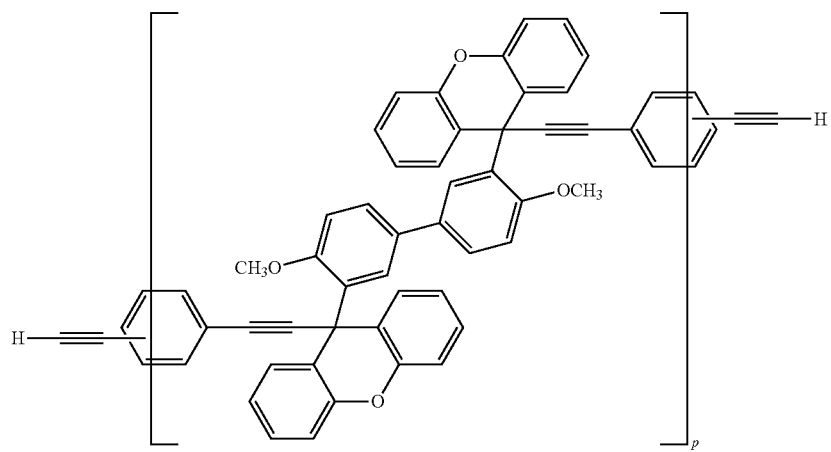

-continued
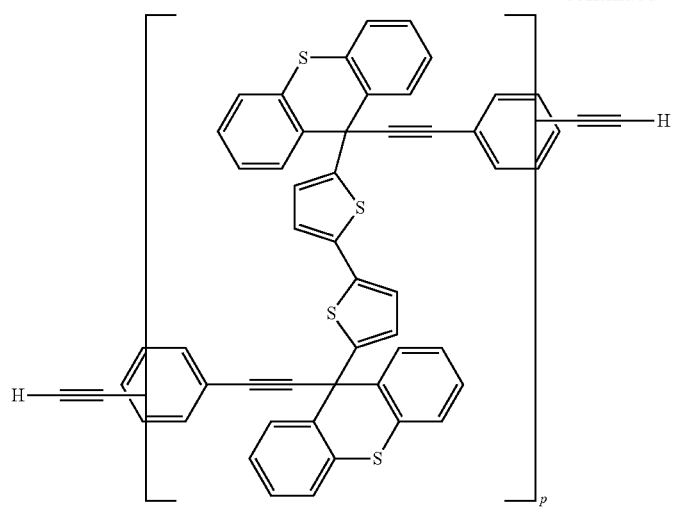
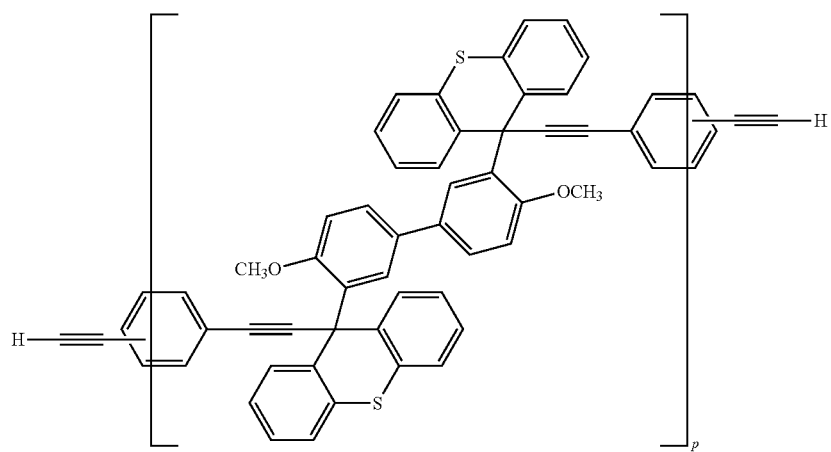
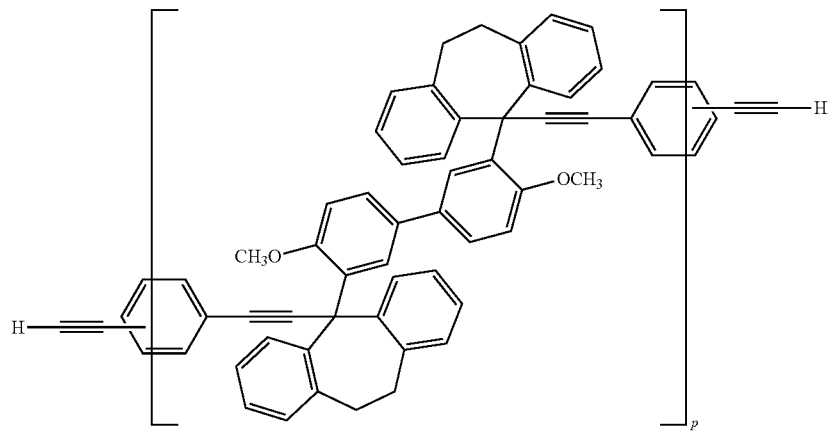

-continued
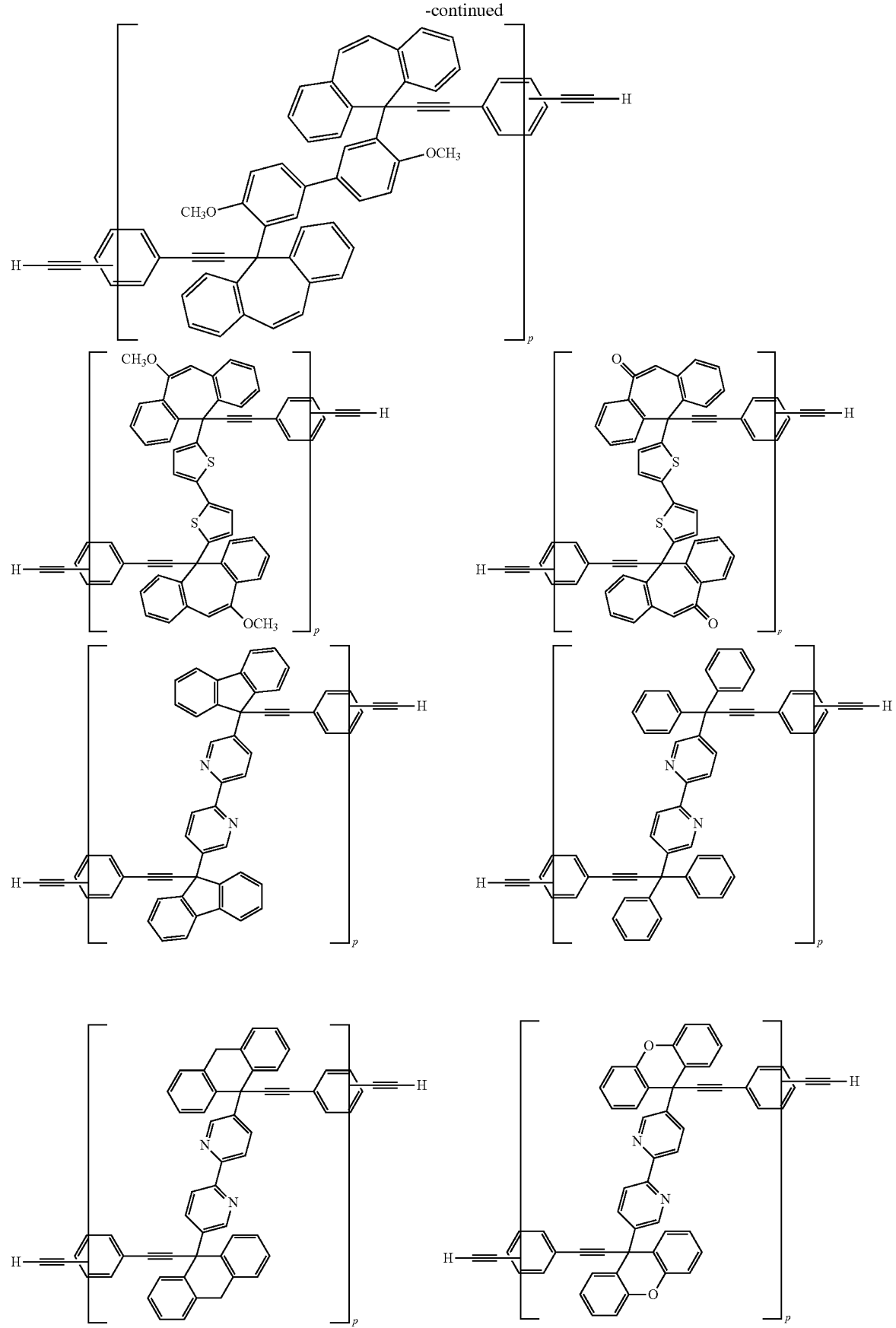

-continued
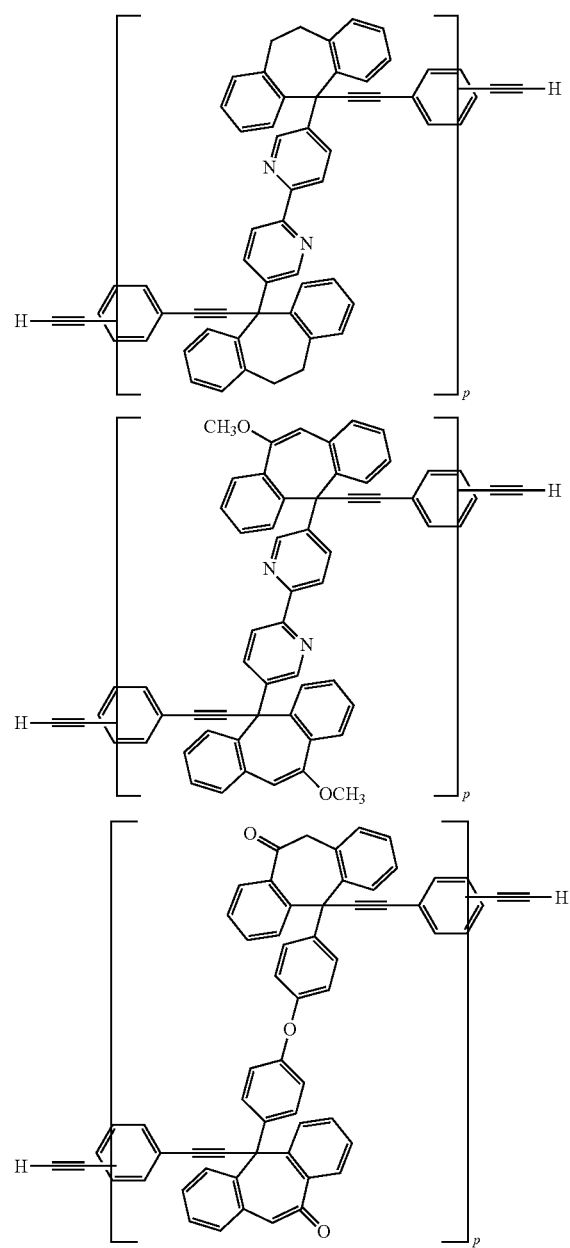
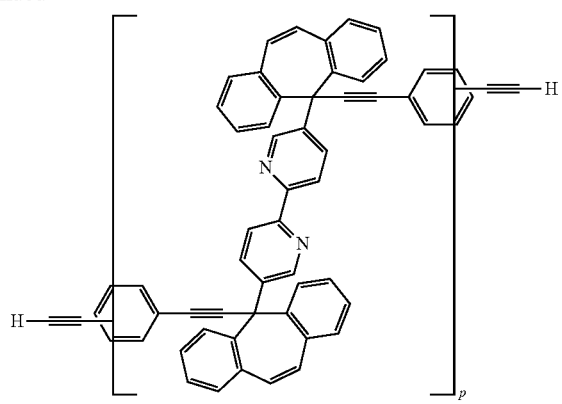
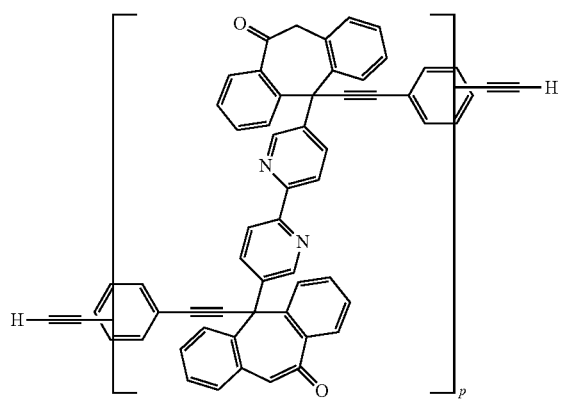
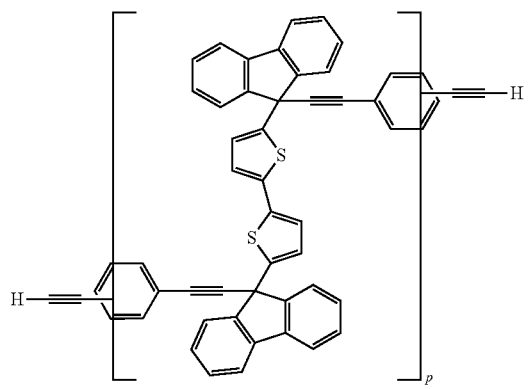
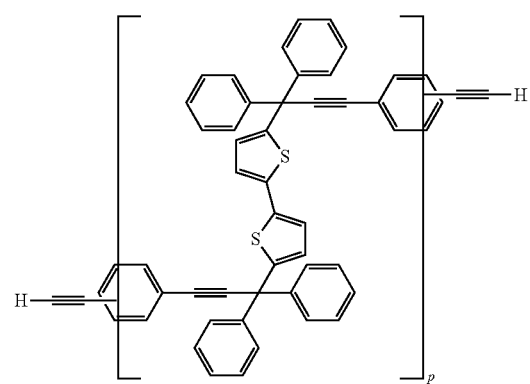
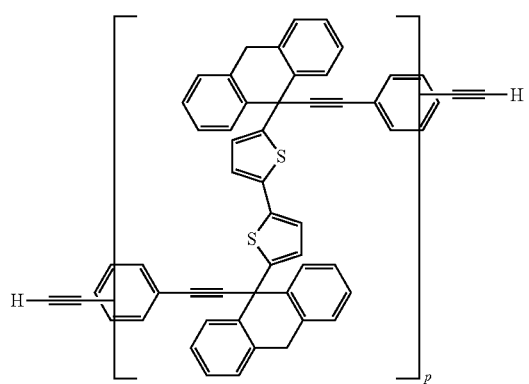

-continued
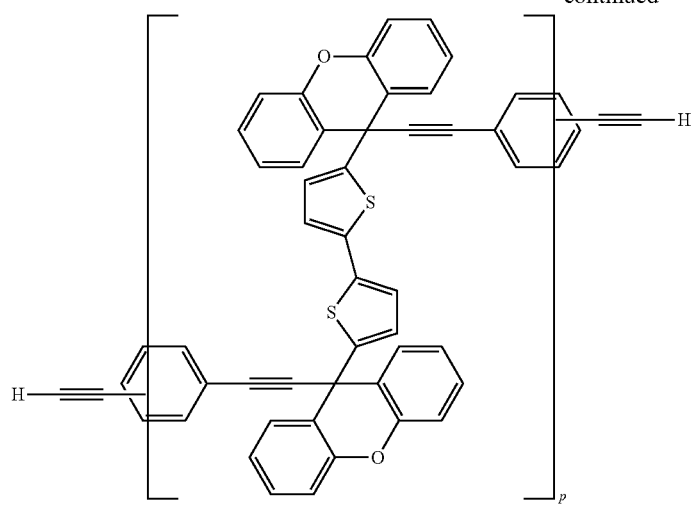
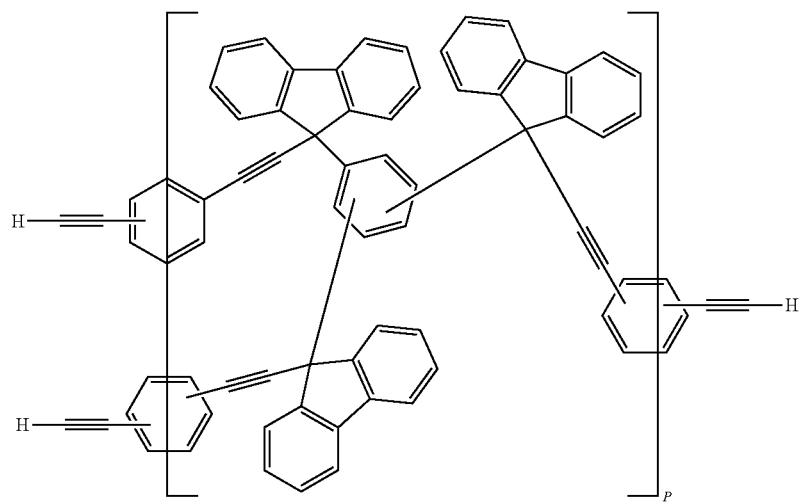
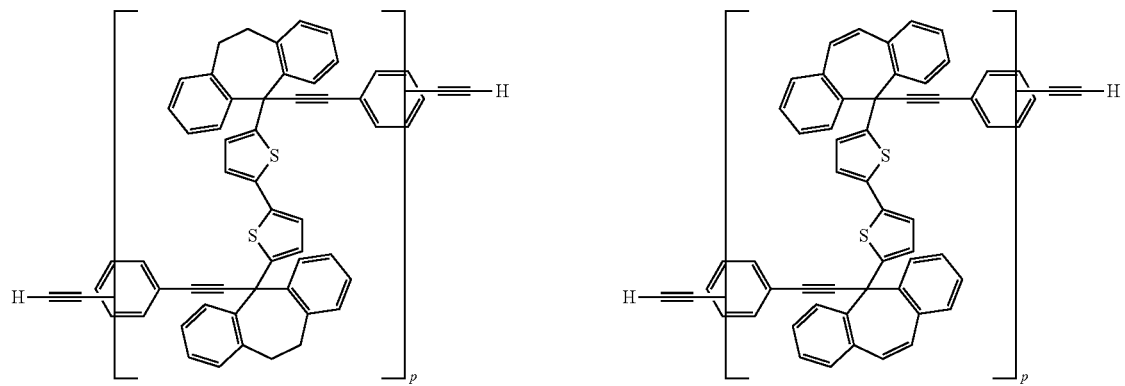

-continued
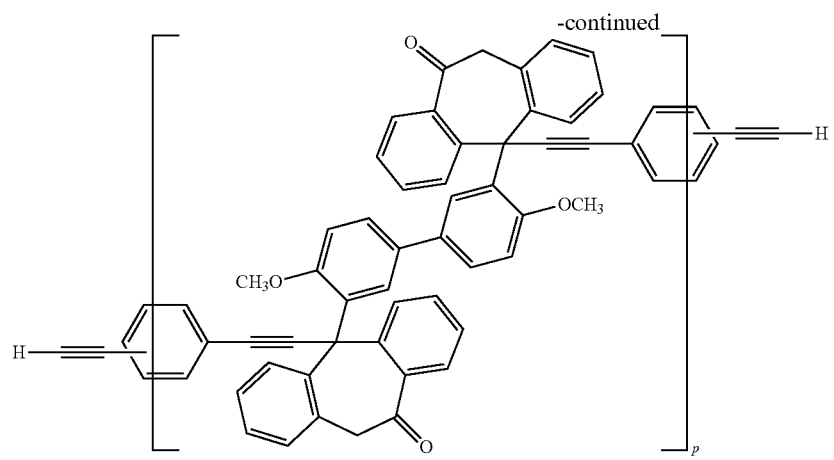
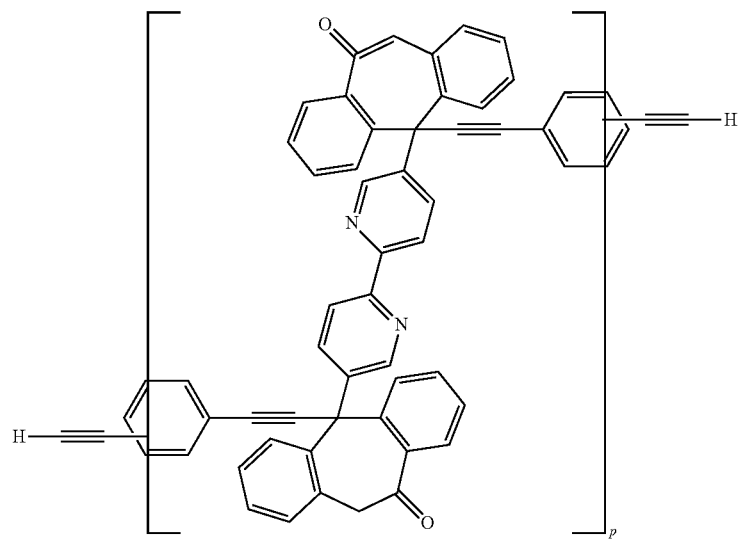
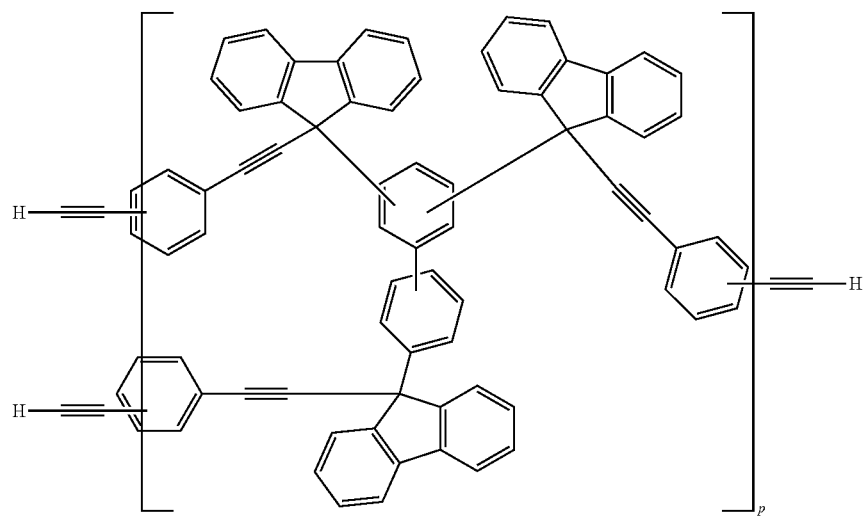

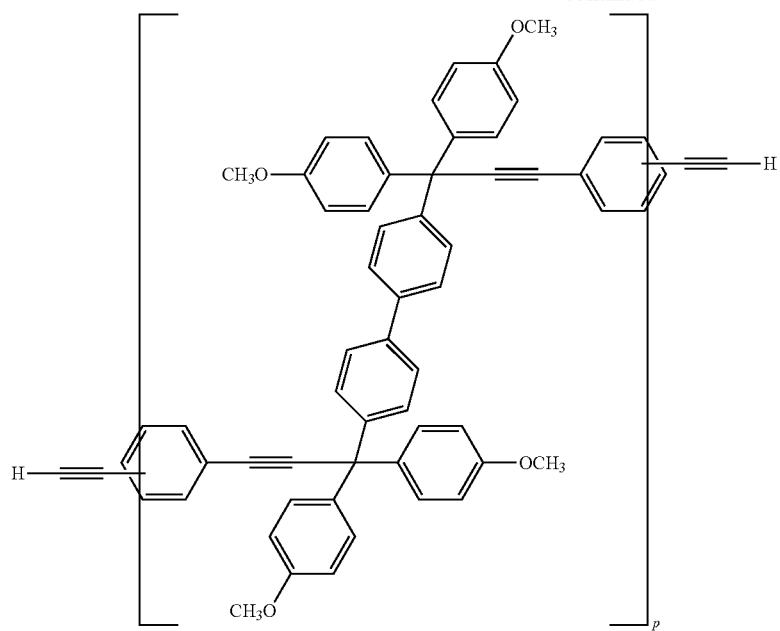
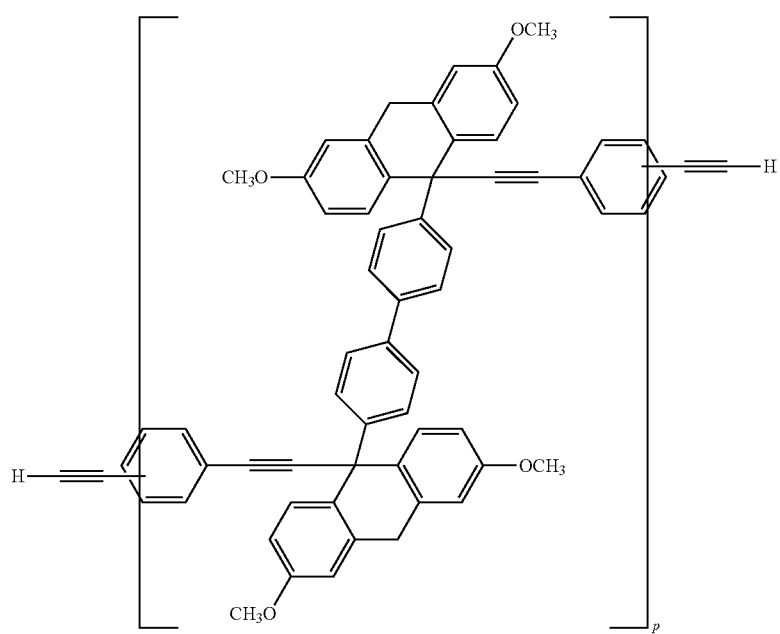

-continued
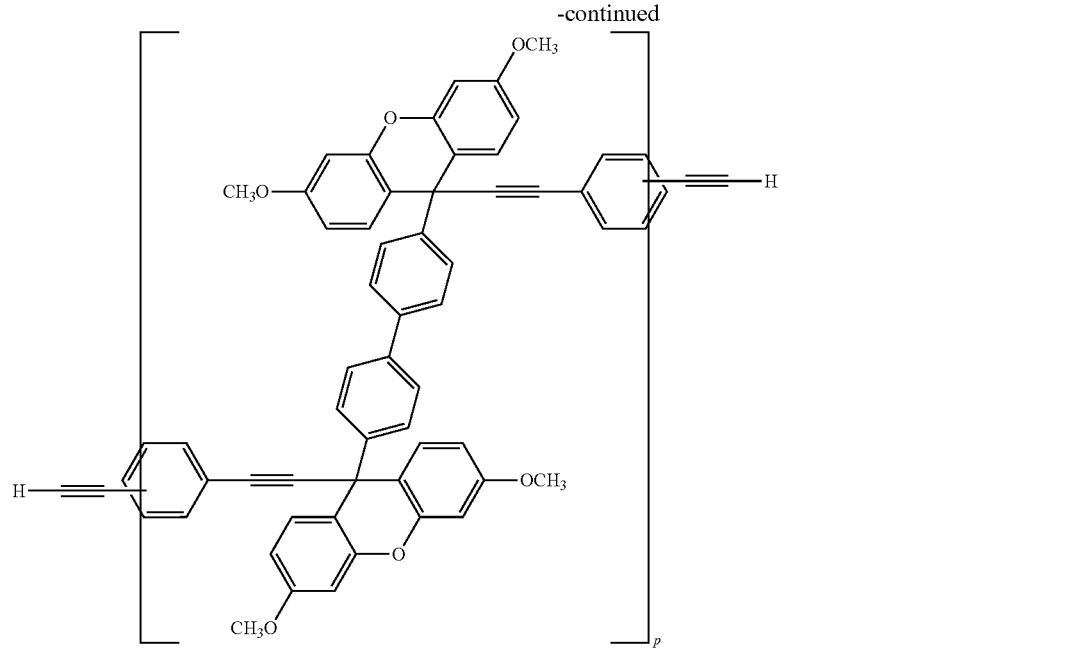
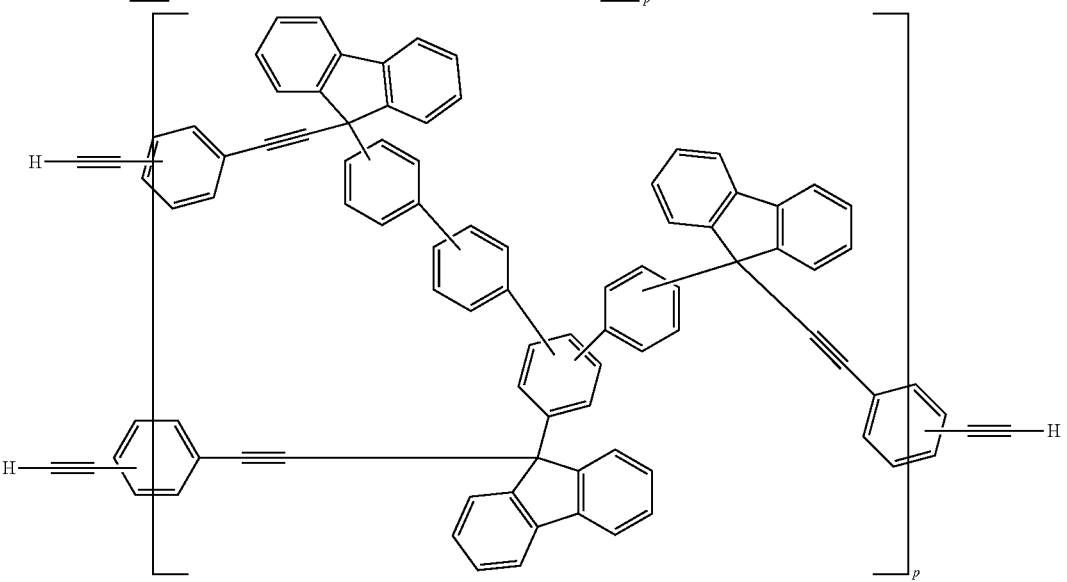
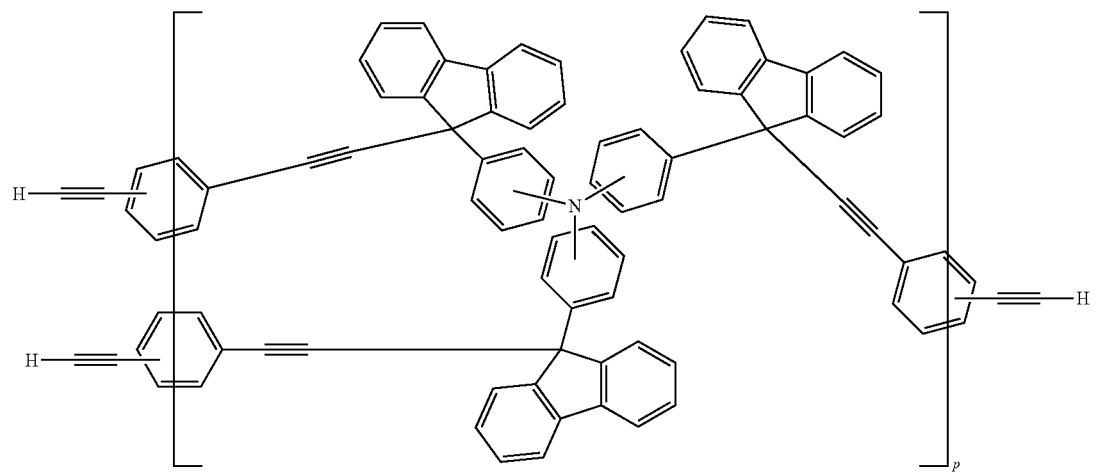

-continued
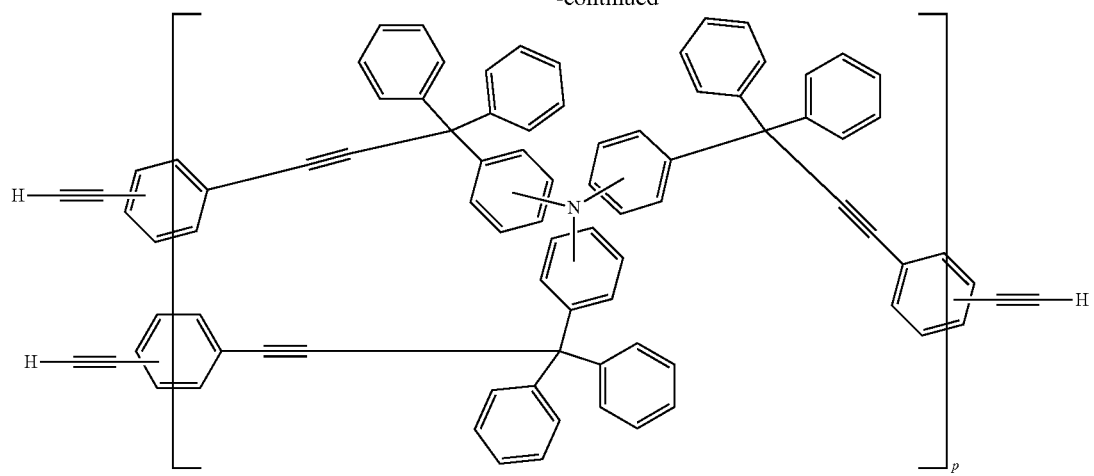
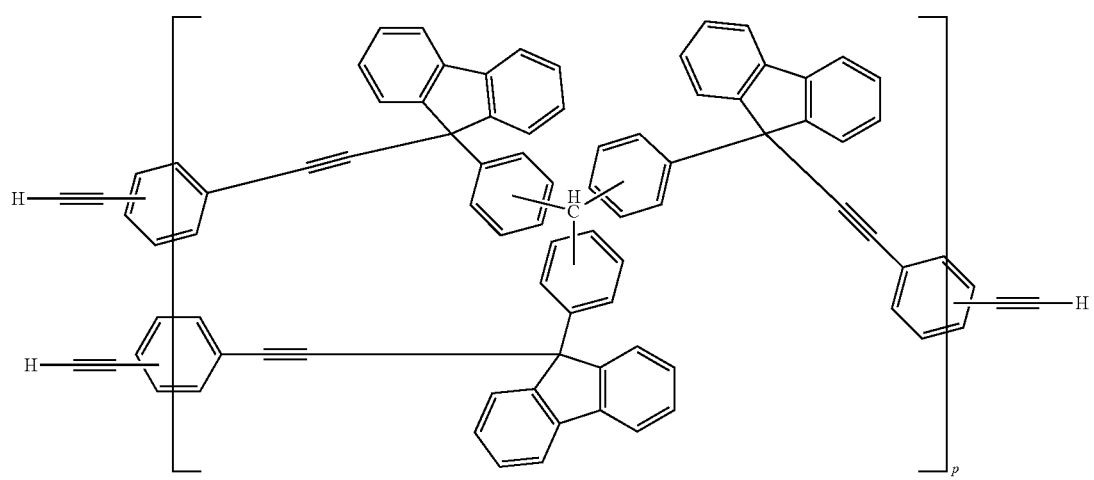
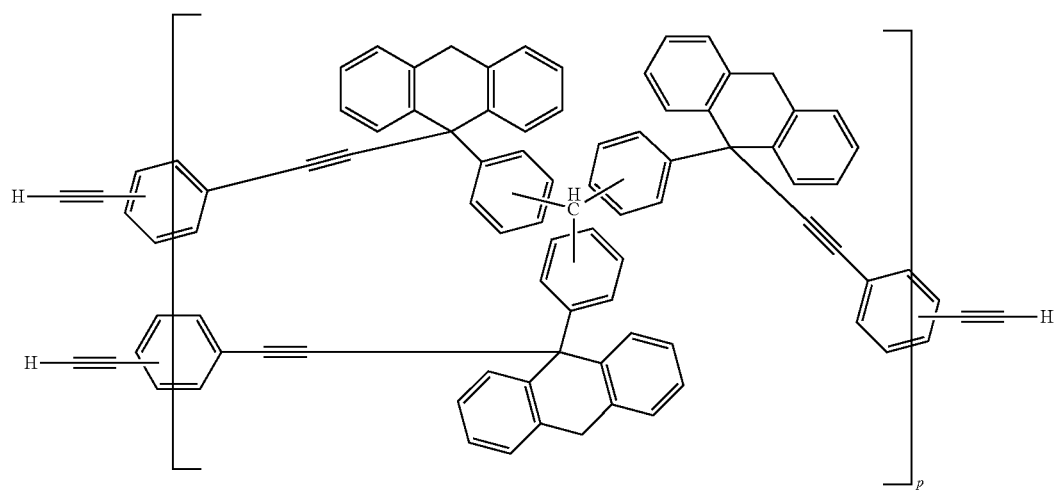

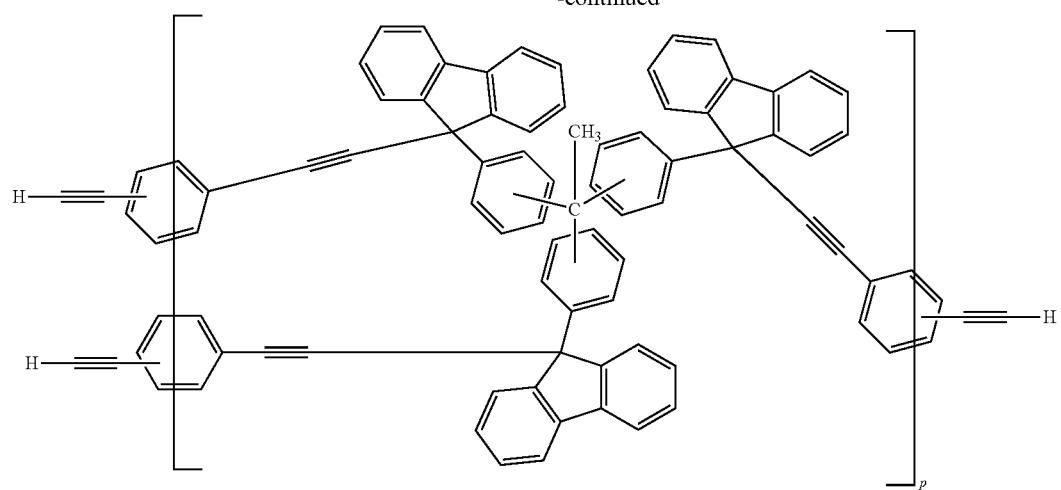
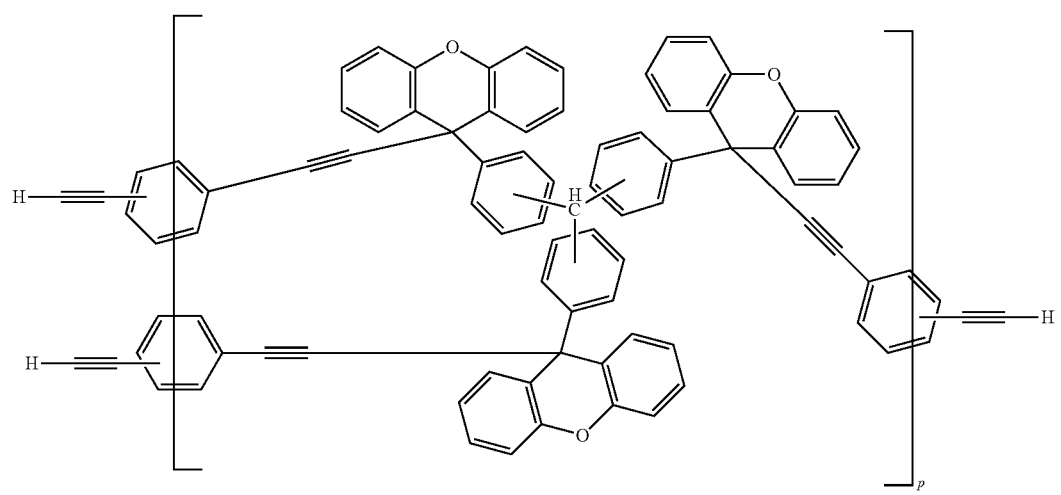
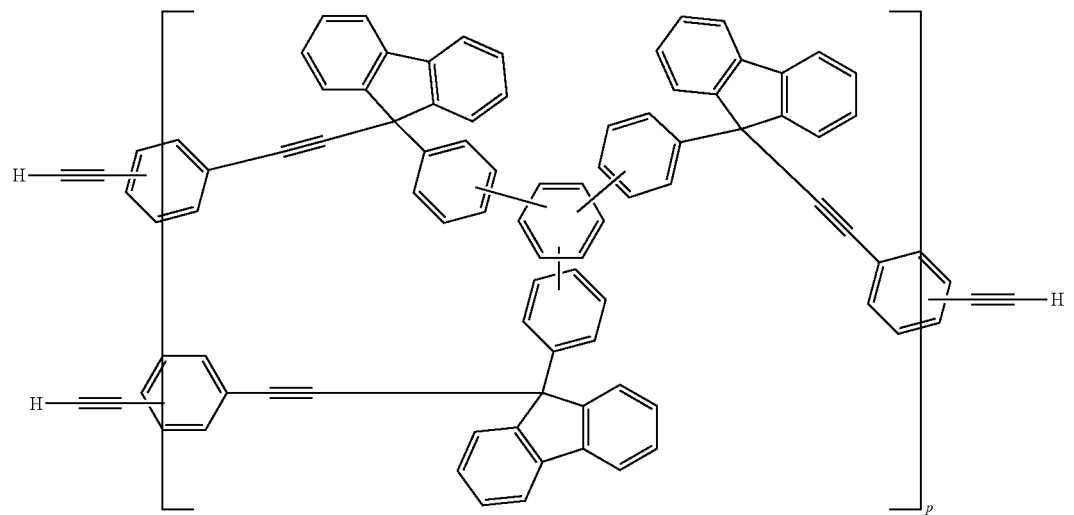

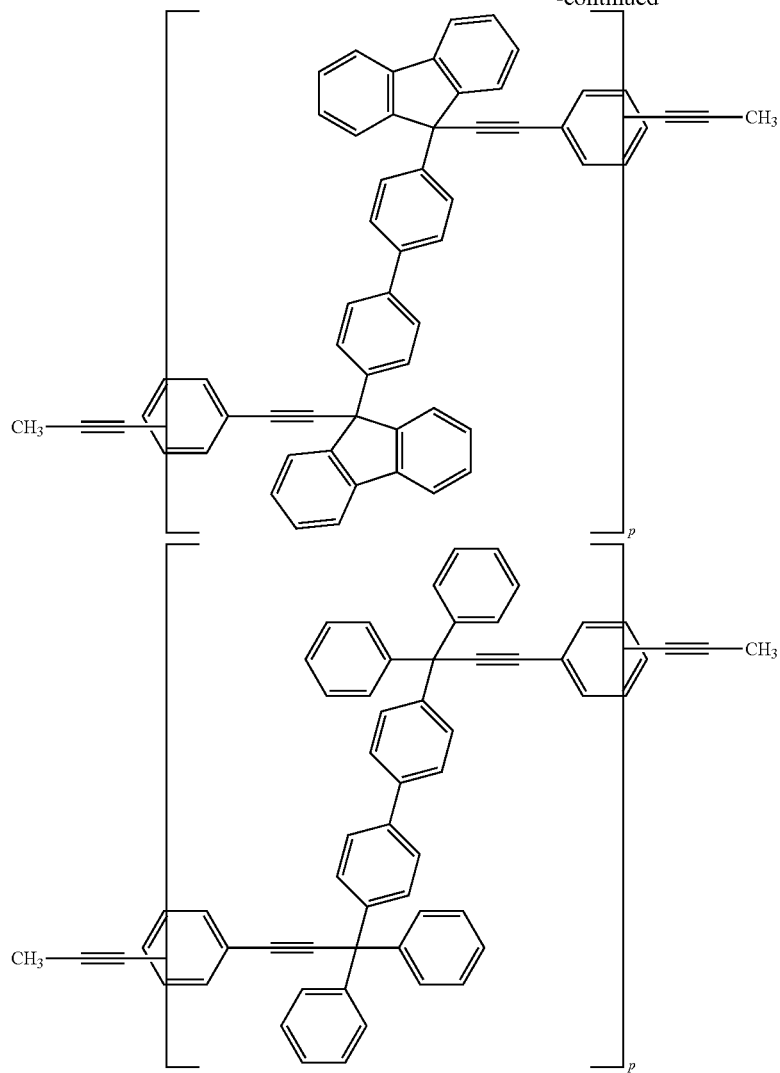
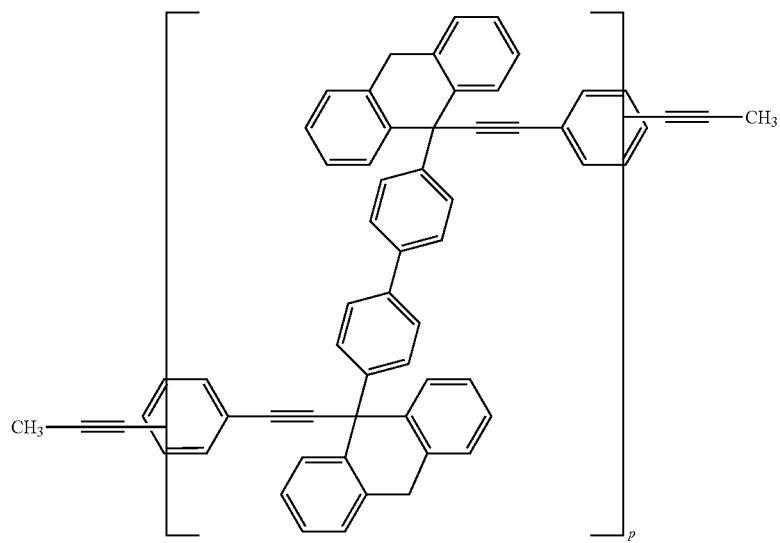

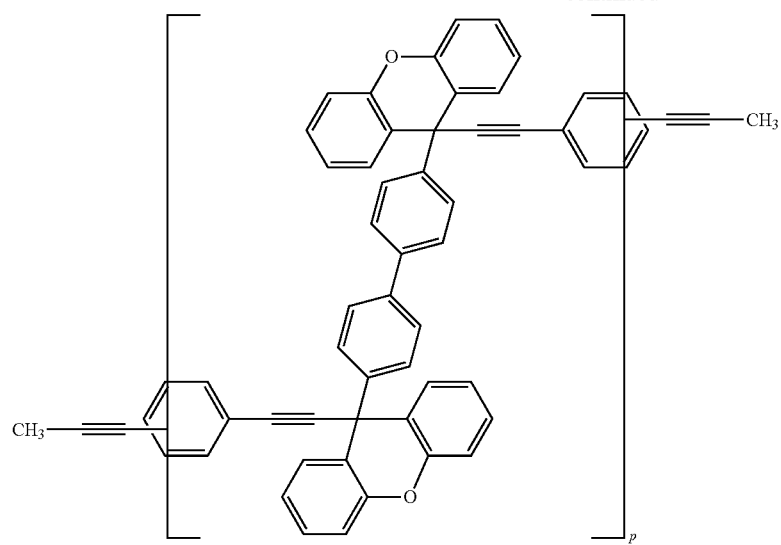
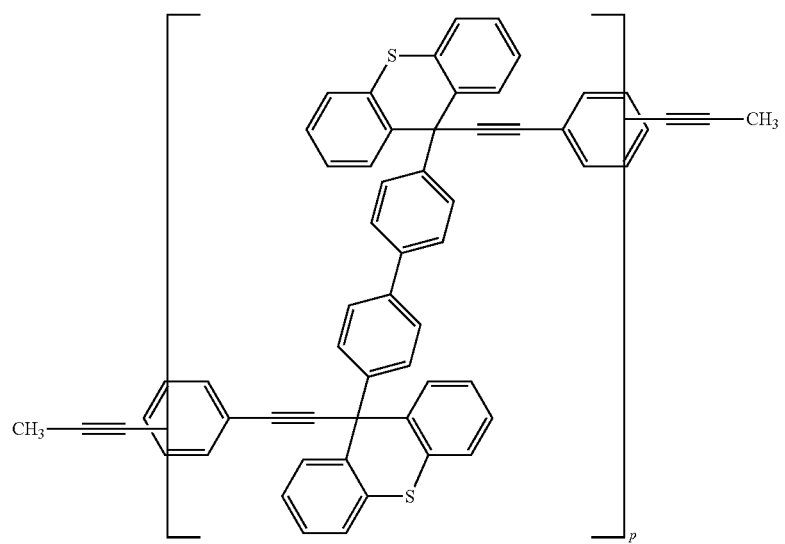
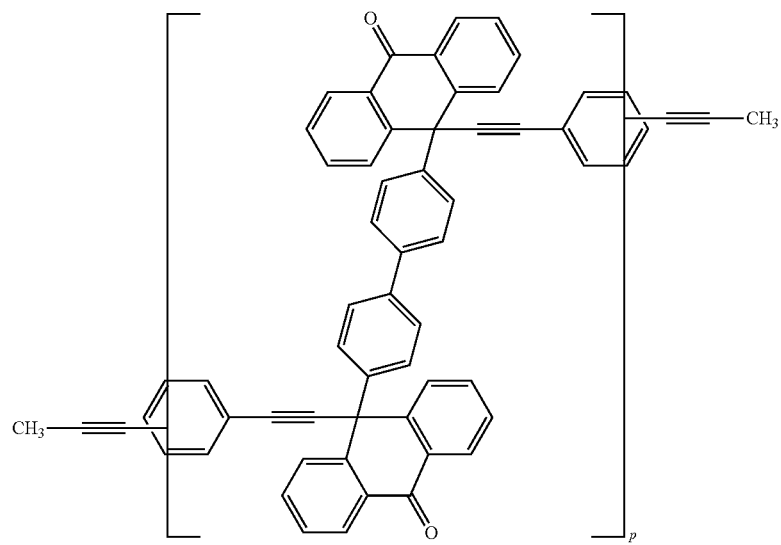

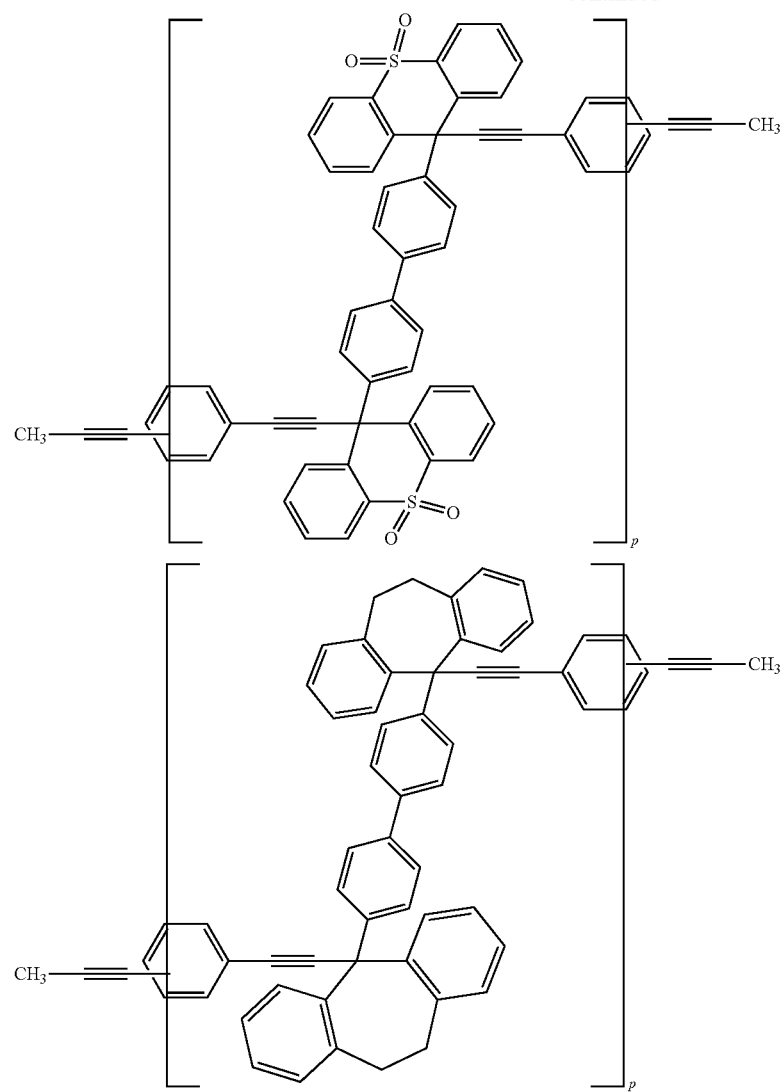
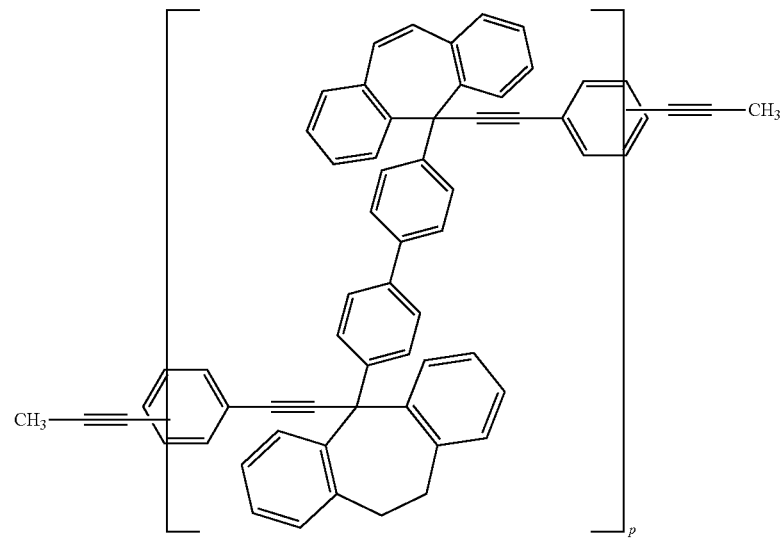

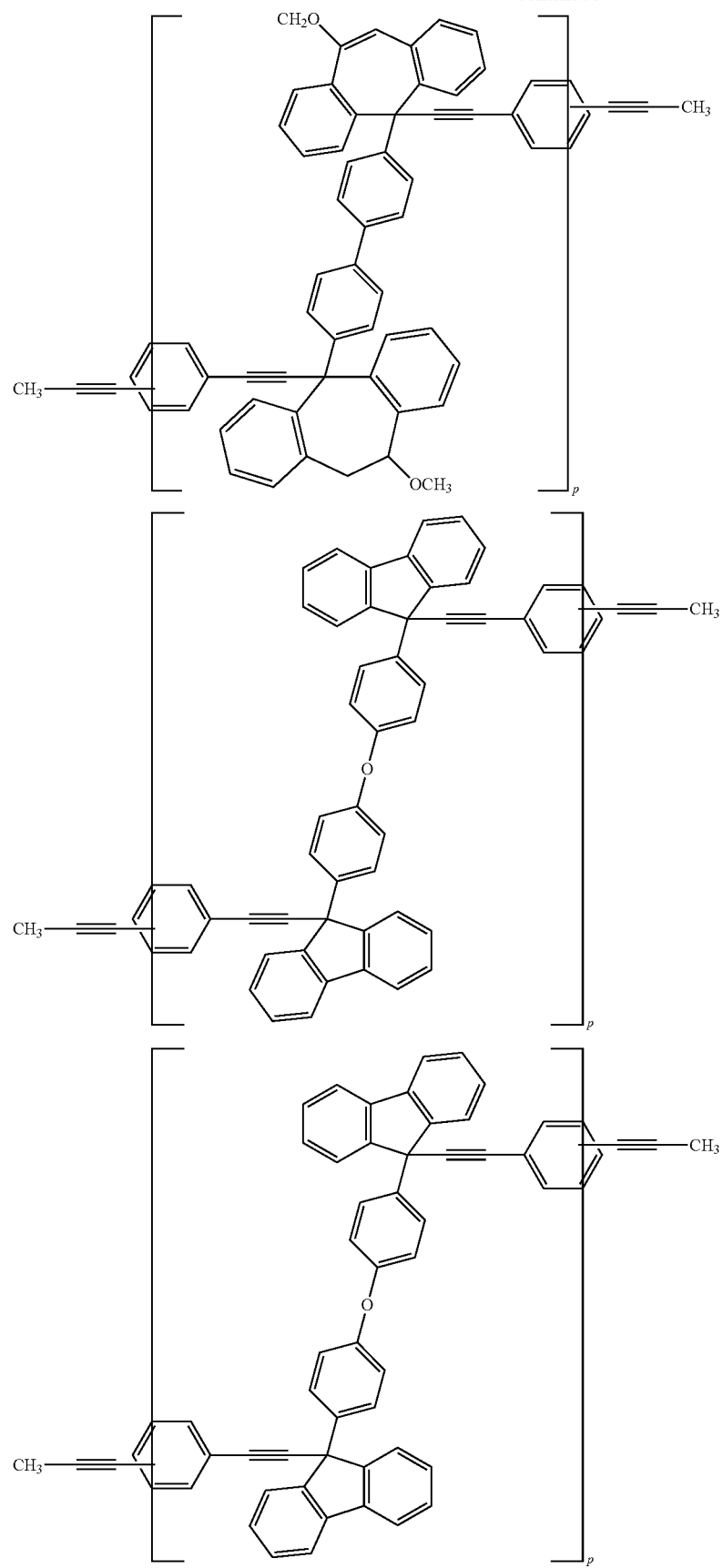

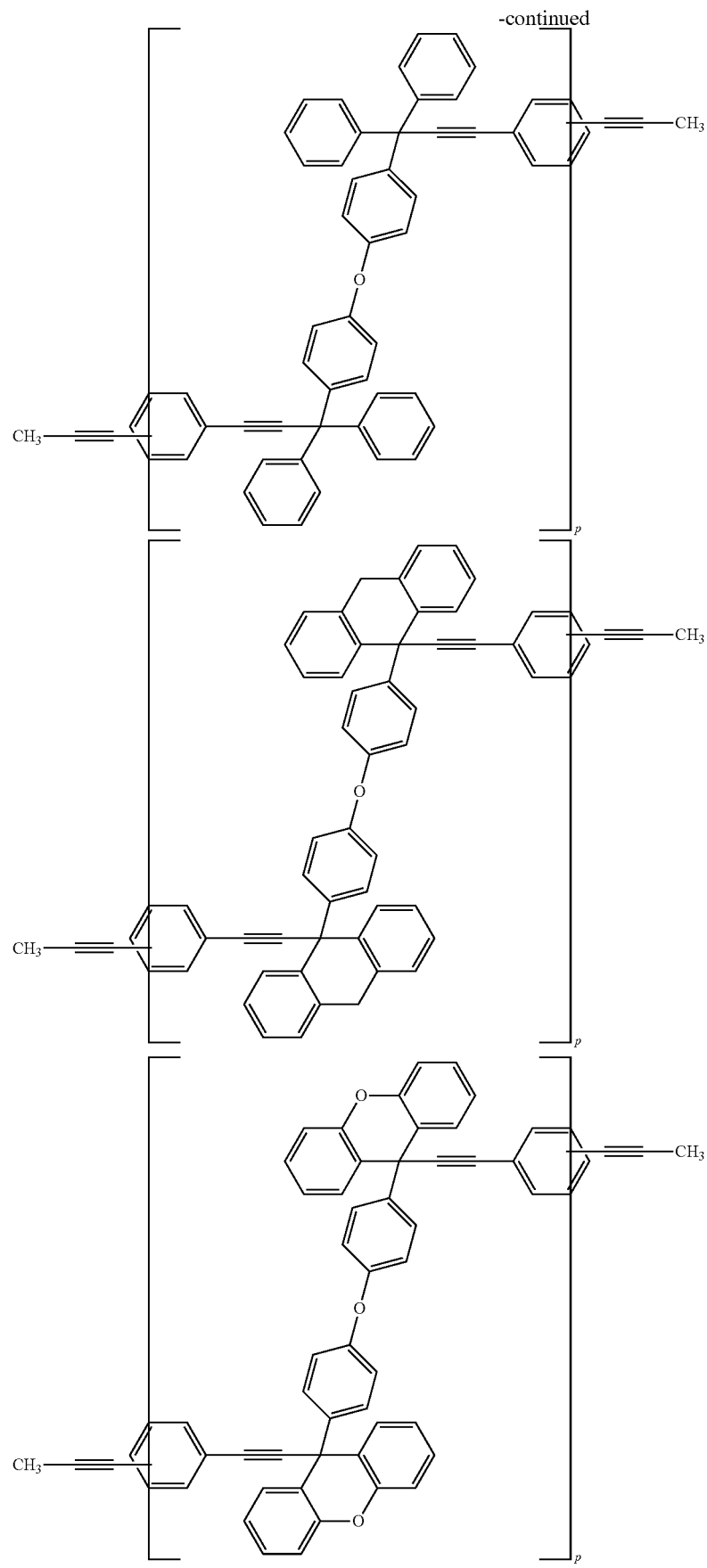

-continued
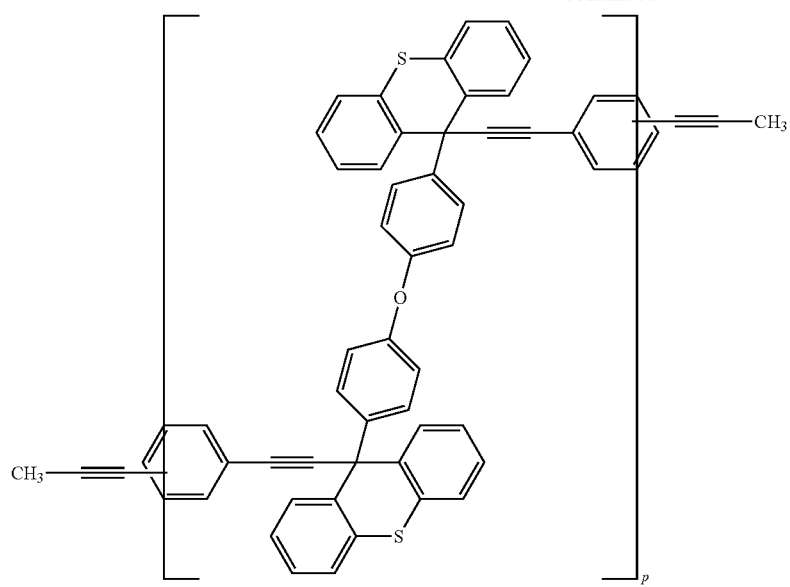
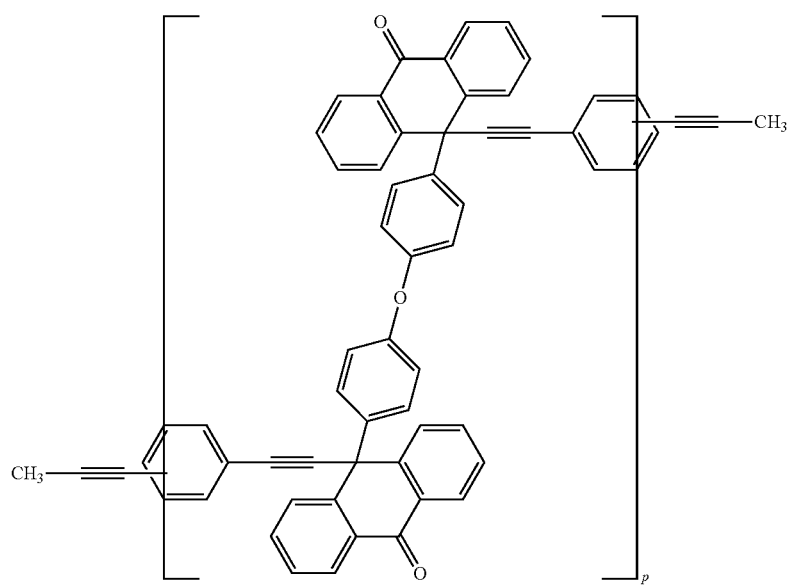

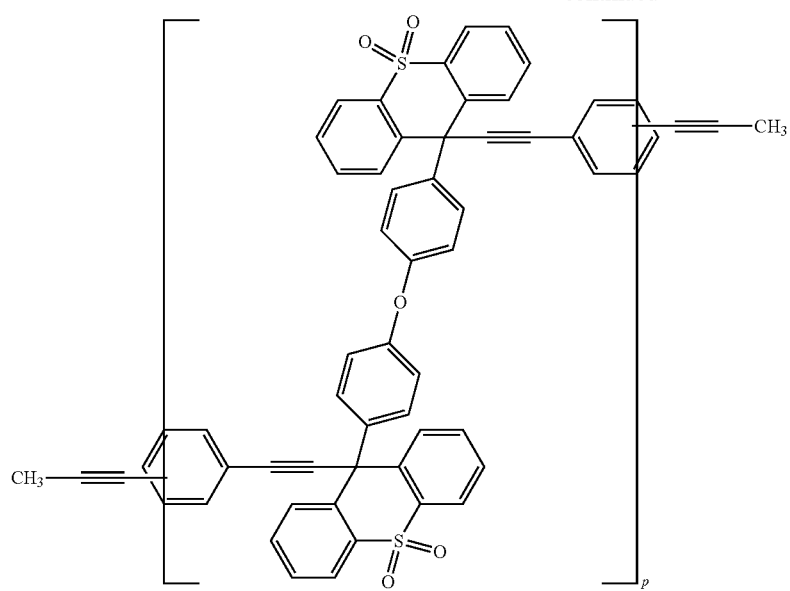
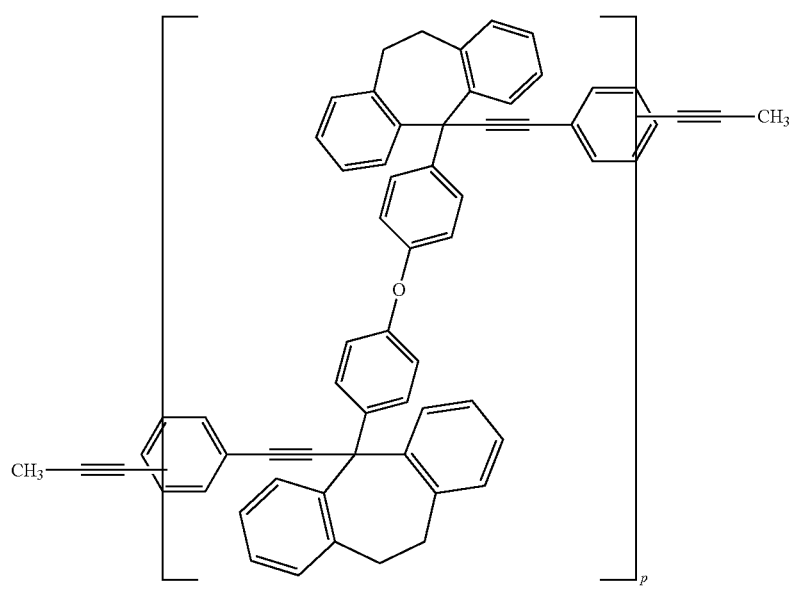

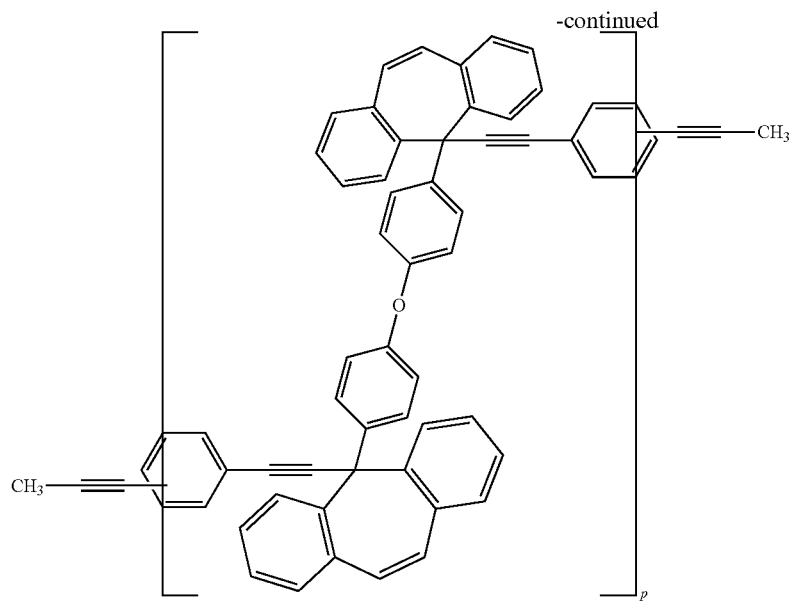

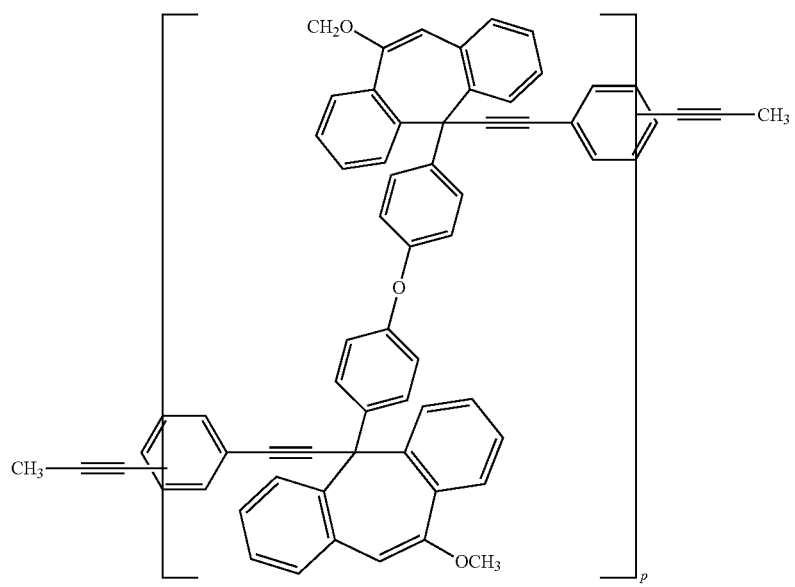

In the formula described above, "p" represents a repeating number and is 1 to 50.

The inventive Compound (1) preferably has a weight average molecular weight ranging 500 to 20,000, which is determined by calculation. The weight average molecular weight is more preferably 15,000 or less in view of planarizing and gap filling characteristics. With such a molecular weight, the compound is more improved in thermal fluidity, and enables the composition containing the same to favorably fill a fine structure formed on a substrate, and to form an organic film to planarize the whole substrate.

[Method for Manufacturing Compound]

The method for manufacturing the inventive Compound (1) may be a method that involves a step of producing a diol and/or triol (iii) by addition reaction of an organometallic reagent (ii) to the following ketone compound (i) (the following formula (4-1)), a step of deriving the compound (iii) to a dihalide and/or trihalide (iv) (the following formula (4-2)), and a step of producing a compound (vi) by substitution reaction of the compound (iv) with an organometallic reagent (v) (the following formula (4-3)),

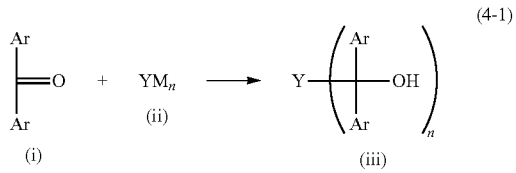

wherein Ar and Y have the same meanings as defined above; "n" is 2 or 3; M represents Li or Mg-Hal, and Hal represents Cl, Br, or I;

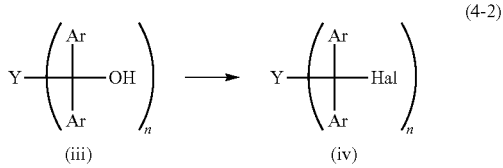

(4-2)

wherein Ar, Y, Hal, and "n" have the same meanings as defined above;

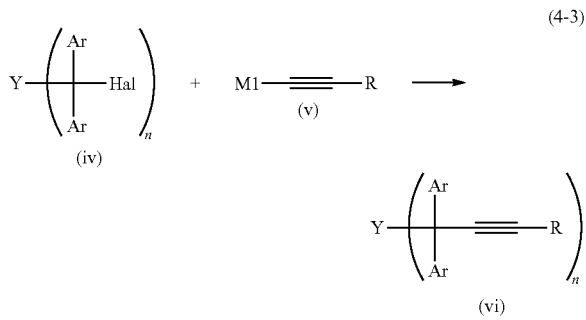

(4-3)

wherein Ar, Y, "n", Hal, and R have the same meanings as defined above; and M1 represents Li or Mg-Hal.

In the reaction of formula (4-1), it is preferable to use the organometallic reagent (ii) in an amount of 0.2/n to 40/n mol, particularly 0.5/n to 2/n mol relative to 1 mol of the ketone compound of the formula (i). As the organometallic reagent (ii), Grignard reagents and organolithium reagents are particularly preferable. Incidentally, as an organometallic reagent for addition reaction with the ketone compound to obtain the compound of the present invention, organometallic reagents other than the compound (ii) can be used. As these organometallic reagents, organozinc reagents, organotitanium reagents, etc. are exemplified. The Grignard reagent and the organolithium reagent may be prepared by direct metallation of a corresponding halide and metal magnesium or metal lithium, or may be prepared by a metal-halogen exchange reaction with an aliphatic organometallic compound such as an isopropyl magnesium halide, methyl lithium, and butyl lithium. Also, the organozinc reagent or the organotitanium reagent can be prepared from a corresponding Grignard reagent or organolithium reagent by the reaction with a zinc halide, a titanium(IV) halide, or a titanium(IV) alkoxide. In the preparation of the organometallic reagent (ii) and/or in the reaction between the organometallic reagent and the ketone compound (i), a metal salt compound may be co-presented. As the metal salt compound, a cyanide, a halide, and a perhalogenic acid salt are exemplified, and particularly lithium salts such as lithium chloride, lithium bromide, lithium iodide, and lithium perchlorate, and copper salts such as copper(I) cyanide, copper(II) cyanide, copper(I) chloride, copper(II) chloride, and dilithium tetrachlorocuprate are preferably exemplified. These metal salts are capable of increasing the solubility of the organometallic reagent to facilitate the preparation thereof and controlling the nucleophilicity or Lewis acidity of the reagent when the metal salt compound is added in an amount of 0.01 to 5.0 equivalents, preferably 0.2 to 2.0 equivalents based on an amount of the organometallic reagent. The solvent to be used for preparing the organometallic reagent (ii) and in the reaction with the ketone compound (i) may be exemplified ethers such as diethyl ether, dibutyl ether, tetrahydrofuran, 1,4-dioxane, cyclopentyl methyl ether, and t-butyl methyl ether; hydrocarbons such as benzene, toluene, xylene, mesitylene, hexane, heptane, octane, and isooctane; an aprotic polar solvent such as N,N,N',N'-tetramethylethylenediamine, hexamethylphosphoric triamide, and N,N-dimethylformamide, which can be used singly or by mixture. The reaction temperature may vary depending on a kind of the ketone compound (i) and the organometallic reagent (ii) as well as the reaction conditions, but is preferably −70 to 150° C. The temperature can be selected in many ways such as −70 to 10° C. in case of using an organolithium reagent as the compound (ii) and from room temperature to the boiling point of the solvent (under reflux) in case of using a Grignard reagent as the compound (ii). The reaction is desirably completed by tracing the reaction using chromatography to determine the reaction time, but may be performed for 30 minutes to 48 hours normally.

As the method of the reaction of formula (4-2) for deriving the diol and/or triol (iii) to the dihalide and/or trihalide (iv), it is possible to use a reaction of the diol and/or triol (iii) with a halogenated compound such as hydrogen chloride, hydrogen bromide, thionyl chloride, thionyl bromide, phosgene, and carboxylic acid halide such as acetyl chloride and acetyl bromide. Illustrative examples of the solvent to be used for this reaction include ethers such as ethylene glycol monomethyl ether, propylene glycol monomethyl ether, diethyl ether, dibutyl ether, diethylene glycol diethyl ether, diethylene glycol dimethyl ether, tetrahydrofuran, and 1,4-dioxane; chlorinated solvent such as methylene chloride, chloroform, dichloroethane, and trichloroethylene; hydrocarbons such as hexane, heptane, benzene, toluene, xylene, and cumene; nitriles such as acetonitrile; ketones such as acetone, ethyl methyl ketone, and isobutyl methyl ketone; esters such as ethyl acetate, n-butyl acetate, and propylene glycol methyl ether acetate; and an aprotic polar solvent such as dimethylsulfoxide, N,N-dimethylformamide, and hexamethylphosphoric triamide, which can be used singly or by mixture of two or more kinds. The reaction temperature is preferably from −50° C. to the boiling point of the solvent, more preferably room temperature to 100° C.

In the reaction of formula (4-3), the compound (vi), that is, the compound (1) is obtained by substitution reaction of the dihalide and/or trihalide (iv) with the organometallic reagent (v). In this case, Grignard reagents and organolithium reagents are particularly preferable as the organometallic reagent (v). Incidentally, as the organometallic reagent to obtain the compound of the present invention, organometallic reagents other than the compound (v) can be used. As these organometallic reagents, organozinc reagents, organotitanium reagents, etc. are exemplified. The Grignard reagent and the organolithium reagent may be prepared by a reaction of a corresponding acetylene compound and alkylmagnesium halide including Grignard reagents such as methylmagnesium chloride, methylmagnesium bromide, ethylmagnesium chloride, and ethylmagnesium bromide, or an aliphatic organometallic compound such as methyl lithium or n-butyl lithium. Illustrative examples of the solvent to be used for the reaction of the dihalide or trihalide (iv) with the organometallic reagent (v) include ethers such as diethyl ether, dibutyl ether, tetrahydrofuran, 1,4-dioxane, cyclopentyl methyl ether, and t-butyl methyl ether; hydrocarbons such as benzene, toluene, xylene, mesitylene, hexane, heptane, octane, and isooctane; aprotic polar solvents such as N,N,N',N'-tetramethylethylenediamine, hexamethylphosphoric triamide, and N,N-dimethylformamide, which can be used singly or by mixture of two or more kinds. The reaction temperature may vary depending on a kind of the dihalide or trihalide (iv) and the organometallic reagent (v) as well as the reaction conditions, but is preferably −70 to 150° C. The temperature can be selected in many ways such as from room temperature to the boiling point of the solvent (under reflux) when the compound (v) is a Grignard reagent and −70 to 10° C. when the compound (v) is an organolithium reagent. The reaction is desirably completed by tracing the reaction using chromatography to determine the reaction time, but may be performed for 30 minutes to 48 hours normally.

The method for manufacturing the inventive Compound (2) may be a method that involves a step of producing a diol and/or triol (viii) by addition reaction of the organometallic reagent (ii) to the following ketone compound (vii) (the following formula (5-1)), a step of deriving the compound (viii) to a dihalide and/or trihalide (ix) (the following formula (5-2)), and a step of producing a polymer by substitution reaction of the compound (ix) with an organometallic reagent (x) (the following formula (5-3)),

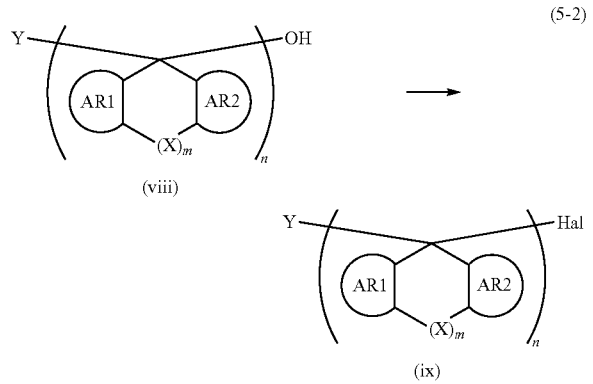

wherein AR1, AR2, X, Y, "m", and "n" have the same meanings as defined above; M represents Li or Mg-Hal, and Hal represents Cl, Br, or I;

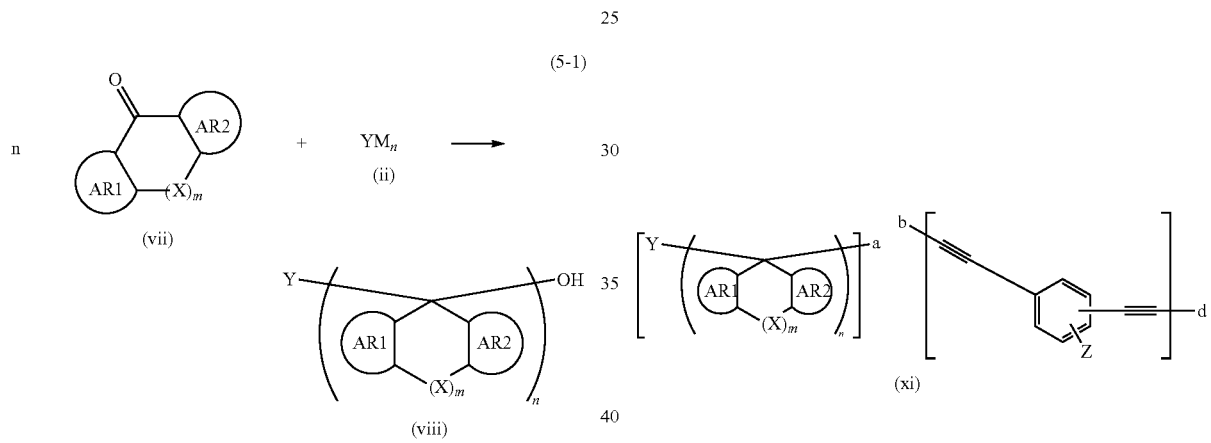

wherein AR1, AR2, X, Y, "m", "n", and Hal have the same meanings as defined above;

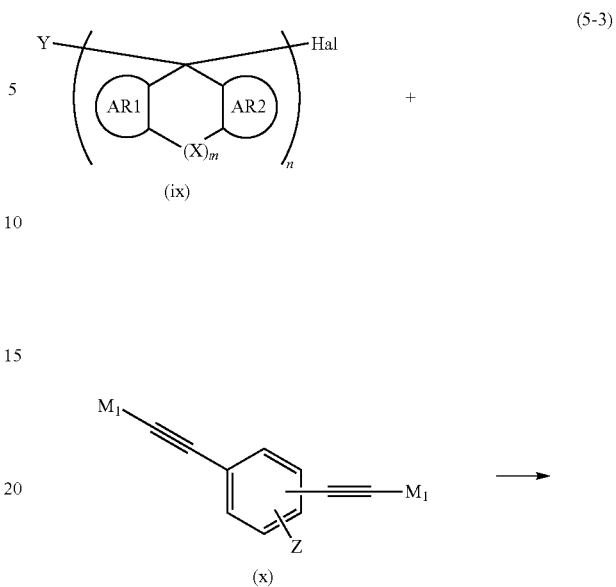

wherein AR1, AR2, X, Y, Z, "m", "n", and Hal have the same meanings as defined above; M1 represents Li or Mg-Hal; "a" bonds with "b", and "d" represents a hydrogen atom or bonds with "a".

In the reaction of formula (5-1), the diol and/or triol (viii) can be obtained by the same method of the formula (4-1) using the compound (vii) instead of the ketone compound (i).

In the reaction of formula (5-2), the dihalide and/or trihalide (ix) can be obtained by the same method of the formula (4-2) using the compound (viii) instead of the diol and/or triol (iii).

In the reaction of formula (5-3), the compound (xi), that is, Compound (2) can be obtained by the same method of the formula (4-3) using the compound (ix) instead of the dihalide and/or trihalide (iv).

At this stage, the dihalide and/or trihalide (ix) may be changed to a compound (xiii) by substitution reaction with the organometallic reagent (x) (the following formula (5-4)), followed by reaction with a halide, an acyl chloride, an acid anhydride, a mesylate ester, a tosylate ester, or a sulfate ester to introduce a monovalent organic group having 1 to 30 carbon atoms to the terminal of the compound (the following formula (5-5)).

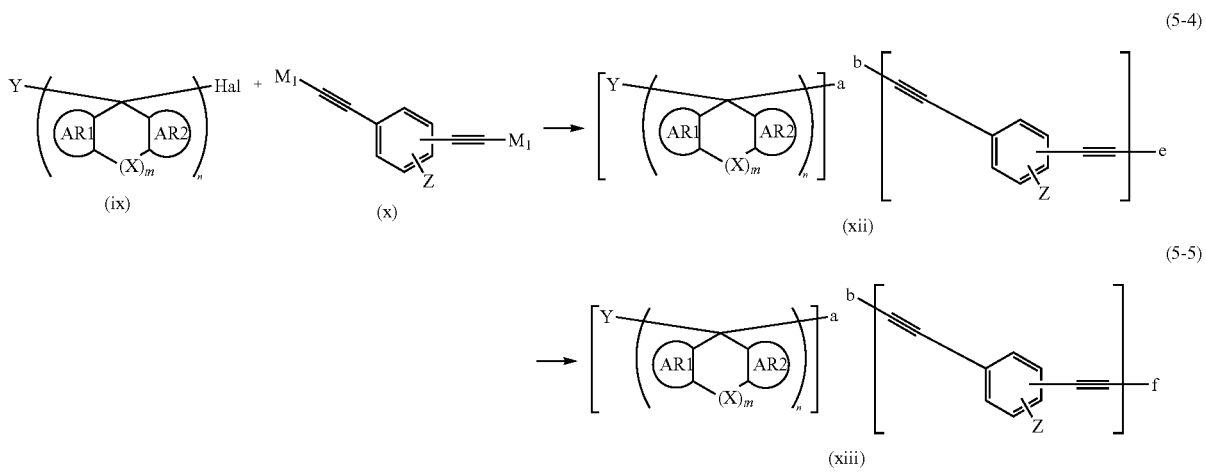

In this formula, AR1, AR2, X, Y, Z, "m", "n", and Hal have the same meanings as defined above; M1 represents Li or Mg-Hal; "a" bonds with "b"; "e" represents M1 or bonds with "a"; and "f" represents a monovalent organic group having 1 to 30 carbon atoms or bonds with "a".

These reactions may be performed such that the substitution reaction of the compound (ix) with the compound (x) and the subsequent reaction to introduce an organic group are performed continuously in the same reaction vessel. These reactions may also be performed such that the reaction of the formula (5-3) is followed by post-treatment to isolate the Compound (2), the isolated Compound (2) is subjected to reaction with an aliphatic organometallic compound to prepare an organometallic reagent, and this reactant is subjected to reaction with a compound selected from halides, mesylate esters, tosylate esters, and sulfate esters to introduce a monovalent organic group.

The following describes a design of Compound (1) of the present invention.

In the inventive Compound (1), the triple bond(s) is disposed to the outer side of the molecule, and accordingly, heat crosslinking reaction occurs even in non-oxygen conditions, which do not cause oxidative crosslinking reaction. The propargyl group have been known as a functional group that is reactive in non-oxygen conditions. In Compound (1) of the present invention, the triple bond and the quarternary carbon are disposed without having an ether structure therebetween, and the heat resistance is more improved thereby. Additionally, the compound has a plurality of aromatic rings that are disposed efficiently in the main skeleton, and realizes very high heat resistance thereby. Accordingly, this compound is very suitable for an organic under layer film for lithography, which is required to be curable in an inert gas to form a film without forming byproducts.

As described above, the inventive compound is capable of curing even in an inert gas, and provides a composition for forming an organic film that has heat resistance at a temperature of 400° C. or more and improved gap filling/planarizing characteristics.

It is to be noted that in the present invention, the planarizing characteristics means a property to make the surface of a substrate planar. With the composition that contains a compound of the present invention, it is possible to decrease a step of 100 nm in a substrate 1 to 30 nm or less by applying a composition 3' for forming an organic film onto the substrate 1, followed by heating to form an organic film 3 as shown in FIG. 1, for example. Incidentally, the stepped profile shown in FIG. 1 represents a typical example of the stepped profiles in substrates for semiconductor device production, and the stepped profile of a substrate that can be planarized by the composition that contains a compound of the present invention is not limited thereto.

<Composition for forming Organic Film>

The present invention also provides a composition for forming an organic film that contains (A) the inventive compound having two or more structures shown by the general formula (1-1) in the molecule, together with (B) an organic solvent. Incidentally, the inventive compound can be used singly or in combination of two or more kinds in the inventive composition for forming an organic film.

The organic solvent (B) that is usable for the inventive composition for forming an organic film is not particularly limited so long as it dissolves the inventive compound, the acid generator, the crosslinking agent, and other additives. Specifically, it is possible to use solvents having a boiling point less than 180° C. such as solvents described in paragraphs [0091]-[0092] of Japanese Patent Laid-Open Publication No. 2007-199653. Among them, propylene glycol monomethyl ether acetate, propylene glycol monomethyl ether, 2-heptanone, cyclopentanone, cyclohexanone, and a mixture of two or more kinds of these are preferably used.

The composition like this is a composition for forming an organic film that can be applied by spin coating to bring excellent dry etching durability as well as heat resistance at a temperature of 400° C. or more and improved gap filling/planarizing characteristics since the composition contains the inventive compound described above.

As the organic solvent of the inventive composition for forming an organic film, it is possible to add a high boiling point solvent having a boiling point of 180° C. or more to the solvent having a boiling point less than 180° C. (it is possible to use admixture of a solvent having a boiling point less than 180° C. and a solvent having a boiling point of 180° C. or more). As the high boiling point organic solvent, it is possible to use any solvent including hydrocarbons, alcohols, ketones, esters, ethers, chlorinated solvents, etc. so long as it can dissolve the compound of the present invention. Specific examples thereof include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4- heptanediol, 2-ethyl-1,3-hexanediol, diethylene glycol, dipropylene glycol, triethylene glycol, tripropylene glycol, glycerin, n-nonyl acetate, ethylene glycol monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monopheyl ether, diethylene glycol monobenzyl ether, diethylene glycol diethyl ether, diethylene glycol dibutyl ether, diethylene glycol butyl methyl ether, triethylene glycol dimethyl ether, triethylene glycol monomethyl ether, triethylene glycol n-butyl ether, triethylene glycol butyl methyl ether, triethylene glycol diacetate, tetraethylene glycol dimethyl ether, dipropylene glycol monomethyl ether, dipropylene glycol mono-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol monomethyl ether acetate, dipropylene glycol methyl n-propyl ether, dipropylene glycol methyl ether acetate, 1,4-butanediol diacetate, 1,3-butylene glycol diacetate, 1,6-hexanediol diacetate, triethylene glycol diacetate, γ-butyrolactone, dihexyl malonate, diethyl succinate, dipropyl succinate, dibutyl succinate, dihexyl succinate, dimethyl adipate, diethyl adipate, and dibutyl adipate, which can be used singly or by mixture of two or more kinds.

The high boiling point solvent may be appropriately selected such that the boiling point is adjusted to a temperature of heat treatment of the composition for forming an organic film. The high boiling point solvent to be added preferably has a boiling point of 180 to 300° C., more preferably 200 to 300° C. With such a boiling point, sufficient thermal fluidity can be obtained since the baking (heat treatment) can be performed without a risk that the solvent evaporates instantly due to the boiling point being too low. With such a boiling point, the film after baking does not contain the remained solvent that has failed to evaporate, and the film properties such as etching durability are not affected.

When the high boiling point solvent is used, the blending amount of the high boiling point solvent is preferably 1 to 30 parts by mass relative to 100 parts by mass of the solvent having a boiling point less than 180° C. Such a blending amount does not cause risks that sufficient thermal fluidity cannot be obtained in baking due to too small blending amount, or the solvent remains in the film to degrade the film properties such as etching durability due to too large blending amount.

The composition for forming an organic film like this, with the compound for forming an organic film being additionally provided with thermal fluidity by adding the high boiling point solvent, becomes a composition for forming an organic film having improved gap filling/planarizing characteristics.

Into the inventive composition for forming an organic film, (C) acid generator can be added to promote the curing reaction further. As the acid generator, any type can be added including acid generators that generate acid by heat decomposition and acid generators that generate acid by light irradiation. Specific examples of the acid generator that can be added include materials described in paragraphs [0061]-[0085] of JP 2007-199653A, but is not limited thereto.

The above acid generator can be used singly or by mixture of two or more kinds. When the acid generator is added, the blending amount is preferably 0.05 to 50 parts by mass, more preferably 0.1 to 10 parts by mass relative to 100 parts by mass of the compound (A).

Into the inventive composition for forming an organic film, (D) a surfactant can be added to improve coatability in spin coating. The surfactant can be used those described in paragraphs [0142]-[0147] of JP 2009-269953A.

Into the inventive composition for forming an organic film, a (E) crosslinking agent can be added to improve the curability and to prevent intermixing with the upper layer film. The crosslinking agent is not particularly limited, and it is possible to use wide variety of known crosslinking agents in various types. Illustrative examples thereof include melamine crosslinking agents, glycoluril crosslinking agents, benzoguanamine crosslinking agents, urea crosslinking agents, β-hydroxyalkylamide crosslinking agents, isocyanurate crosslinking agents, aziridine crosslinking agents, oxazoline crosslinking agents, and epoxy crosslinking agents.

Illustrative examples of the melamine crosslinking agent include hexamethoxymethylated melamine, hexabutoxymethylated melamine, alkoxy and/or hydroxy substituents thereof, and partial self-condensates thereof. Illustrative examples of the glycoluril crosslinking agent include tetramethoxymethylated glycoluril, tetrabutoxymethylated glycoluril, alkoxy and/or hydroxy substituents thereof, and partial self-condensates thereof. Illustrative examples of the benzoguanamine crosslinking agent include tetramethoxymethylated benzoguanamine, tetrabutoxymethylated benzoguanamine, alkoxy and/or hydroxy substituents thereof, and partial self-condensates thereof. Illustrative examples of the urea crosslinking agent include dimethoxymethylated dimethoxyethyleneurea, alkoxy and/or hydroxy substituents thereof, and partial self-condensates thereof. Illustrative examples of the p-hydroxyalkylamide crosslinking agent include N,N,N',N'-tetra(2-hydroxyethyl)adipate amide. Illustrative examples of the isocyanurate crosslinking agent include triglycidylisocyanurate and triallylisocyanurate. Illustrative examples of the aziridine crosslinking agent include 4,4'-bis(ethyleneiminocarbonylamino)diphenylmethane and 2,2-bishydroxymethylbutanol-tris[3-(1-aziridinyl)propionate]. Illustrative examples of the oxazoline crosslinking agent include 2,2'-isopropylidene-bis(4-benzyl-2-oxazoline), 2,2'-isopropylidene-bis(4-phenyl-2-oxazoline), 2,2'-methylene-bis(4,5-diphenyl-2-oxazoline), 2,2'-methylene-bis(4-phenyl-2-oxazoline), 2,2'-methylene-bis(4-tert-butyl-2-oxazoline), 2,2'-bis(2-oxazoline), 1,3-phenylene-bis(2-oxazoline), 1,4-phenylene-bis(2-oxazoline), and copolymers of 2-isopropenyloxazoline. Illustrative examples of the epoxy crosslinking agent include diglycidyl ether, ethylene glycol diglycidyl ether, 1,4-butanediol diglycidyl ether, 1,4-cyclohexanedimethanol diglycidyl ether, poly(glycidyl methacrylate), trimethylolethane triglycidyl ether, trimethylolpropane triglycidyl ether, and pentaerythritol tetraglycidyl ether.

Into the inventive composition for forming an organic film, (F) a plasticizer can be added to improve the gap filling/planarizing characteristics. The plasticizer is not particularly limited, and it is possible to use wide variety of known plasticizers in various types. Illustrative examples thereof include low molecular weight compounds such as phthalate esters, adipate esters, phosphate esters, trimellitate esters, and citrate esters; polymers such as polyethers, polyesters, and polyacetal polymers described in JP 2013-253227A.

As an additive to bring the inventive composition for forming an organic film to have further gap filling/planarizing characteristics that is same as in the case of plasticizer, the following examples are preferably used: a liquid state additive having a polyethylene glycol or polypropylene glycol structure, or heat decomposable polymer having a weight loss ratio between 30° C. and 250° C. of 40% by mass or more and a weight average molecular weight of 300 to 200,000. This heat decomposable polymer preferably contains a repeating unit having an acetal structure shown by the following general formula (DP1) or (DP1a).

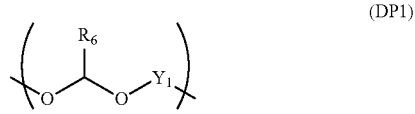
(DP1)

In the formula, $R_6$ represents a hydrogen atom or a saturated or unsaturated monovalent organic group having 1 to 30 carbon atoms which may be substituted; and $Y_1$ represents a saturated or unsaturated divalent organic group having 2 to 30 carbon atoms.

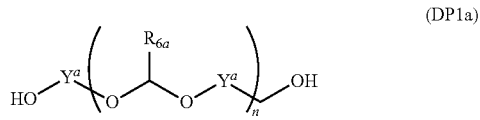
(DP1a)

In the formula, $R_{6a}$ represents an alkyl group having 1 to 4 carbon atoms; $Y^a$ represents a saturated or unsaturated divalent hydrocarbon group having 4 to 10 carbon atoms, which may have an ether bond; and "n" represents an average repeating unit number and is 3 to 500.

As described above, the inventive composition for forming an organic film forms an organic film that has excellent dry etching durability as well as heat resistance at a temperature of 400° C. or more and improved gap filling/planarizing characteristics. Accordingly, it is very useful for an organic under layer film material used for multilayer resist processes such as a two-layer resist process, a three-layer resist process using a silicon-containing resist middle layer film or a silicon-containing inorganic hard mask, and a four-layer resist process using a silicon-containing resist middle layer film or a silicon-containing inorganic hard mask and an organic bottom antireflective coating. The inventive composition for forming an organic film has excellent gap filling/planarizing characteristics without forming byproducts even in film forming in an inert gas, and is favorably used as a planarization material in a production step of a semiconductor device other than the multilayer resist processes.

<Method for forming Organic Film>

The heating step of film forming for forming an organic film can employ one-stage baking, two-stage baking, or multi-stage baking with three or more stages, but one-stage baking or two-stage baking is economical and preferable. The film forming by one-stage baking is preferably performed at a temperature of 100° C. or more and 600° C. or less for 5 to 3600 seconds, particularly at a temperature of 150° C. or more and 500° C. or less for 10 to 7200 seconds.

The heat treatment under these conditions makes it possible to promote the planarization by thermal fluidity and the crosslinking reaction. Onto this obtained film, a coating-type silicon middle layer film or a CVD hard mask is optionally formed in multilayer resist processes. When the coating-type silicon middle layer film is applied, the organic under layer film is preferably formed at a temperature higher than the temperature to form the silicon middle layer film. The silicon middle layer film is usually formed at a temperature of 100° C. or more and 400° C. or less, preferably 150° C. or more and 350° C. or less. When the organic under layer film is formed at a temperature higher than this temperature, it is possible to prevent the organic under layer film from being dissolved by a composition for forming the silicon middle layer film to form an organic film without mixing with the composition. Additionally, it is possible to eliminate the risk that the organic under layer film causes heat decomposition to form byproducts during forming the silicon middle layer film.

When the CVD hard mask is applied, the organic under layer film is preferably formed at a temperature higher than the temperature to form the CVD hard mask. As the temperature to form the CVD hard mask, a temperature of 150° C. or more and 500° C. or less can be exemplified.

On the other hand, in film forming by two-stage baking, when the first-stage baking is performed in air atmosphere, this baking is performed under the conditions that the upper limit of the treatment temperature in air atmosphere is set to 300° C. or less, preferably 250° C. or less and in a range of 10 to 600 seconds if the substrate can cause corrosion due to oxygen. The second-stage in an inert gas is preferably performed by setting the baking temperature to a temperature higher than the baking temperature in the first-stage and 600° C. or less, preferably 500° C. or less for 10 to 7200 seconds.

The inventive composition for forming an organic film can be applied to a method for forming an organic film that functions as an organic under layer film used for a production process of a semiconductor device in which a substrate to be processed is subjected to heat treatment in an atmosphere with the oxygen concentration of 1% or less to form a cured film in order to prevent corrosion of the substrate to be processed.

In the first step of the method for forming such an organic film, the inventive composition for forming an organic film described above is spin coated onto a substrate to be processed. After the spin coating, in two-stage baking, the first baking step is performed in air at a temperature of 300° C. or less, and then the second-stage baking step is performed in an atmosphere with the oxygen concentration of 1% or less. In case of one stage baking, the first-stage baking in air can be skipped. Incidentally, illustrative examples of the atmosphere in baking include inert gases such as nitrogen, argon, and helium. The inventive material is capable of forming a sufficiently cured organic film without forming sublimated products even when it is heated in such an inert gas atmosphere.

The method for forming an organic film can be used for a substrate to be processed that has a structure or step with the height of 30 nm or more. As described above, the inventive composition for forming an organic film excels in gap filling/planarizing characteristics, thereby being capable of forming a planar cured film even when the substrate to be processed has a structure or a step (unevenness) with the height of 30 nm or more. That is, the above method for forming an organic film is particularly useful for forming a planar organic film onto such a substrate to be processed.

The thickness of an organic film to be formed is appropriately selected, but is preferably set to 30 to 20,000 nm, particularly 50 to 15,000 nm.

The above method for forming an organic film is applicable to both cases of using the inventive composition for forming an organic film that becomes an under layer film of a multilayer resist process and for forming an organic film for a planarization film.

The inventive composition for forming an organic film is usable for forming an organic film that is capable of planarizing the surface of substrate topography used in a production process of a semiconductor device, and is applicable to a method for forming an organic film in which the inventive composition is spin coated onto a substrate to be processed, the substrate coated with the composition for forming an organic film is subjected to heat treatment in air atmosphere at a temperature of 50° C. or more and 250° C. or less for 10 to 600 seconds, and subsequently subjected to heat treatment in an inert gas at a temperature of 250° C. or more for 10 to 7200 seconds to form a cured film.

In the first step of the method for forming an organic film, the inventive composition for forming an organic film described above is spin coated onto a substrate to be processed. The use of a spin coating method allows to securely obtain good gap filling characteristics. After the spin coating, baking (heat treatment) is performed in order to promote the planarization by thermal flow and subsequent crosslinking reaction. It is to be noted that this baking allows the solvent in the composition to evaporate, and is capable of preventing mixing even when a resist upper layer film or a silicon-containing resist middle layer film is formed on the organic film.

<Patterning Process>

[Three-Layer Resist Process Using Silicon-Containing Resist Middle Layer Film]

The patterning process can be performed such that an organic film is formed on a substrate to be processed by using the inventive composition for forming an organic film, a silicon-containing film is formed on the organic film by using a silicon containing film-forming material, a resist upper layer film is formed on the silicon-containing film by using a photoresist composition, a circuit pattern is formed on the resist upper layer film, the pattern is transferred to the silicon-containing film by etching using the patterned resist upper layer film, the pattern is transferred to the organic film by etching using the patterned silicon-containing film, and the pattern is transferred to the substrate to be processed by etching using the patterned organic film.

As the substrate to be processed, it is preferable to use a semiconductor device substrate or the semiconductor device substrate having any of a film selected from a metal film, a metal carbide film, a metal oxide film, a metal nitride film, a metal oxycabide film, and a metal oxynitride film formed thereon. Although it is not particularly limited, specific examples thereof include substrates of Si, α-Si, p-Si, $SiO_2$, SiN, SiON, W, TiN, and Al, for example, and these substrate having the above metal thin film formed thereon as a layer to be processed.

As the layer to be processed, various Low-k films and their stopper films can be used, including Si, $SiO_2$, SiON, SiN, p-Si, α-Si, W, W—Si, Al, Cu, and Al—Si, which can be formed to a thickness of 50 to 10,000 nm usually, and particularly 100 to 5,000 nm. It is to be noted that when a layer to be processed is formed, the substrate and the layer to be processed are made from using different materials.

Incidentally, the metal to compose the layer to be processed is preferably silicon, titanium, tungsten, hafnium, zirconium, chromium, germanium, copper, silver, gold, aluminum, indium, gallium, arsenic, palladium, iron, tantalum, iridium, cobalt, manganese, molybdenum, or alloy thereof.

As the substrate to be processed, a substrate to be processed that has a structure or a step with the height of 30 nm or more is preferably used.

When the substrate to be processed is subjected to forming of an organic film by using the inventive composition for forming an organic film, the above method for forming an organic film may be applied.

Subsequently, onto the organic film, a resist middle layer film (silicon-containing resist middle layer film) is formed by using a silicon containing resist middle layer film material. This middle layer film material is preferably based on polysiloxane. The silicon-containing resist middle layer film can possess an antireflective effect. Particularly for exposure at 193 nm, k value becomes higher to increase the reflection of a substrate when the composition for forming an organic layer is a highly aromatic-containing material with high etching selectivity from a substrate. However, the reflection can be decreased to 0.5% or lower if the silicon-containing resist middle layer film has appropriate absorption, k value. Since the silicon-containing resist middle layer film has an antireflective effect, it is preferable to use polysiloxane capable of crosslinking by acid or heat with the pendant structure or polysiloxane structure having a light absorbing group containing anthracene for exposure to light of 248 nm or 157 nm, and a phenyl group or a silicon-silicon bond for exposure to light of 193 nm.

Then, onto the silicon-containing resist middle layer film, a resist upper layer film is formed by using a photoresist composition. The resist upper layer film material may be either positive tone or negative tone, and photoresist compositions in common use can be used. The resist upper layer film material is preferably subjected to spin coating, followed by pre-baking at a temperature of 60 to 180° C. for 10 to 300 seconds. Subsequently, this is subjected to exposure, post-exposure baking (PEB), and development in accordance with a conventional method to give a resist upper layer film pattern. Incidentally, the film thickness of the resist upper layer film is not particularly limited, but is preferably 30 to 500 nm, particularly 50 to 400 nm.

Subsequently, on the resist upper layer film, a circuit pattern (resist upper layer film pattern) is formed. The circuit pattern is preferably formed by lithography using a light having a wavelength of 10 nm or more and 300 nm or less, direct writing with an electron beam, nanoimprinting, or a combination thereof.

The light for exposure can be a high-energy beam having a wavelength of 300 nm or less, and specific examples thereof include deep ultraviolet rays, KrF excimer laser (248 nm), ArF excimer laser (193 nm), $F_2$ laser (157 nm), $Kr_2$ laser (146 nm), Ara laser (126 nm), soft X-rays (EUV) of 3 to 20 nm, electron beams (EB), ion beams, and X-rays.

In forming the circuit pattern, the circuit pattern is preferably developed by aqueous alkaline development or organic solvent development.

Then, the pattern is transferred to the silicon-containing resist middle layer film by etching using the patterned resist upper layer film. The etching of the silicon-containing resist middle layer film, which is performed by using the patterned resist upper layer film, is preferably performed by using a fluorocarbon base gas. In this way, a silicon-containing resist middle layer film pattern is formed.

Next, the pattern is transferred to the organic film by etching using the patterned silicon-containing resist middle layer film. The etching of the organic film using the patterned silicon-containing resist middle layer film is preferably performed by using an etching gas mainly composed of oxygen gas or hydrogen gas since silicon-containing resist middle layer films have higher etching durability against oxygen gas or hydrogen gas compared to organic materials. In this way, the organic film pattern is successfully formed.

Subsequently, the pattern is transferred to the substrate to be processed by etching using the patterned organic film. The subsequent etching of a substrate to be processed (layer to be processed) can be performed by a common method such as etching with fluorocarbon base gas when the substrate to be processed is a low dielectric constant insulation film of $SiO_2$, SiN, or silica, and etching with chlorine-base or bromine-base gas when the substrate to be processed is p-Si, Al, or W. When the substrate is processed by etching with fluorocarbon base gas, the silicon-containing resist middle layer pattern is delaminated at the time of substrate processing. On the other hand, when the substrate is processed by etching with chlorine-base or bromine-base gas, the substrate processing has to be followed by dry etching delamination with fluorocarbon base gas separately performed in order to delaminate the silicon-containing resist middle layer pattern.

The organic film obtained by using the inventive composition for forming an organic film is excellent in etching durability in the etching of a substrate to be processed as described above.

[Four-Layer Resist Process Using Silicon-Containing Resist Middle Layer Film and Organic Bottom Antireflective Coating]

The patterning process can also be performed such that an organic film is formed on a substrate to be processed by using the inventive composition for forming an organic film, a silicon-containing resist middle layer film is formed on the organic film by using a silicon containing resist middle layer film material, an organic bottom antireflective coating is formed on the silicon-containing resist middle layer film, a resist upper layer film is formed on the organic bottom antireflective coating by using a photoresist composition, a circuit pattern is formed on the resist upper layer film, the pattern is transferred to the organic bottom antireflective coating and the silicon-containing resist middle layer film by dry etching using the patterned resist upper layer film, the pattern is transferred to the organic film by etching using the patterned silicon-containing resist middle layer film, and the pattern is transferred to the substrate to be processed by etching using the patterned organic film.

Incidentally, this method can be performed in the same way as in the three layer resist process by using the silicon-containing resist middle layer film except that the organic bottom antireflective coating (BARC) is formed between the silicon-containing resist middle layer film and the resist upper layer film.

The organic bottom antireflective coating can be formed by spin coating using a conventional organic bottom antireflective coating material.

[Three-Layer Resist Process Using Inorganic Hard Mask]

As the patterning process by the three layer resist process using the composition for forming an organic film of the present invention, the patterning process can also be performed such that an organic film is formed on a substrate to be processed by using the inventive composition for forming an organic film, an inorganic hard mask selected from a silicon oxide film, a silicon nitride film, a silicon oxynitride film, titanium oxide film, and titanium nitride film is formed on the organic film, a resist upper layer film is formed on the inorganic hard mask by using a resist upper layer film material composed of a photoresist composition, a circuit pattern is formed on the resist upper layer film, the pattern is transferred to the inorganic hard mask by etching using the patterned resist upper layer film, the pattern is transferred to the organic film by etching using the patterned inorganic hard mask, and the pattern is transferred to the substrate to be processed by etching using the patterned organic film.

Incidentally, this method can be performed in the same way as in the three layer resist process by using the silicon-containing resist middle layer film except that an inorganic hard mask is formed on the organic film instead of the silicon-containing resist middle layer film.

The inorganic hard mask selected from a silicon oxide film, a silicon nitride film, and a silicon oxynitride film (SiON film) can be formed by a CVD method or an ALD method. The method for forming a silicon nitride film is described in, for example, JP 2002-334869A and WO2004/066377. The inorganic hard mask preferably has a film thickness of 5 to 200 nm, more preferably 10 to 100 nm. As the inorganic hard mask, the SiON film, which has marked antireflective properties, is most preferably used. The temperature of a substrate can reach to 300 to 500° C. when an SiON film is formed. Accordingly, the under layer film must be durable to temperatures ranging from 300 to 500° C. The organic film formed by using the inventive composition for forming an organic film has higher heat resistance and is durable to temperatures ranging from 300 to 500° C., thereby making it possible to combine an inorganic hard mask formed by a CVD method or an ALD method and an organic film formed by a spin coating method.

[Four-Layer Resist Process Using Inorganic Hard Mask and Organic Bottom Antireflective Coating]

As the patterning process by the four layer resist process using the composition for forming an organic film of the present invention, the patterning process can also be performed such that an organic film is formed on a substrate to be processed by using the inventive composition for forming an organic film, an inorganic hard mask selected from a silicon oxide film, a silicon nitride film, and a silicon oxynitride film is formed on the organic film, an organic bottom antireflective coating is formed on the inorganic hard mask, a resist upper layer film is formed on the organic bottom antireflective coating by using a resist upper layer film material composed of a photoresist composition, a circuit pattern is formed on the resist upper layer film, the pattern is transferred to the organic bottom antireflective coating and the inorganic hard mask by etching using the patterned resist upper layer film, the pattern is transferred to the organic film by etching using the patterned inorganic hard mask, and the pattern is transferred to the substrate to be processed by etching using the patterned organic film.

Incidentally, this method can be performed in the same way as in the three layer resist process by using the inorganic hard mask except that the organic bottom antireflective coating (BARC) is formed between the inorganic hard mask and the resist upper layer film.

In particular, when a SiON film is used as the inorganic hard mask, it is possible to decrease reflection by virtue of the two-layer antireflective films of the SiON film and the BARC film, even by a liquid immersion exposure at a higher NA exceeding 1.0. Another merit of the formation of the BARC includes obtaining of reduced footing of the resist upper layer film pattern compared to just on the SiON film.

Figure 2:
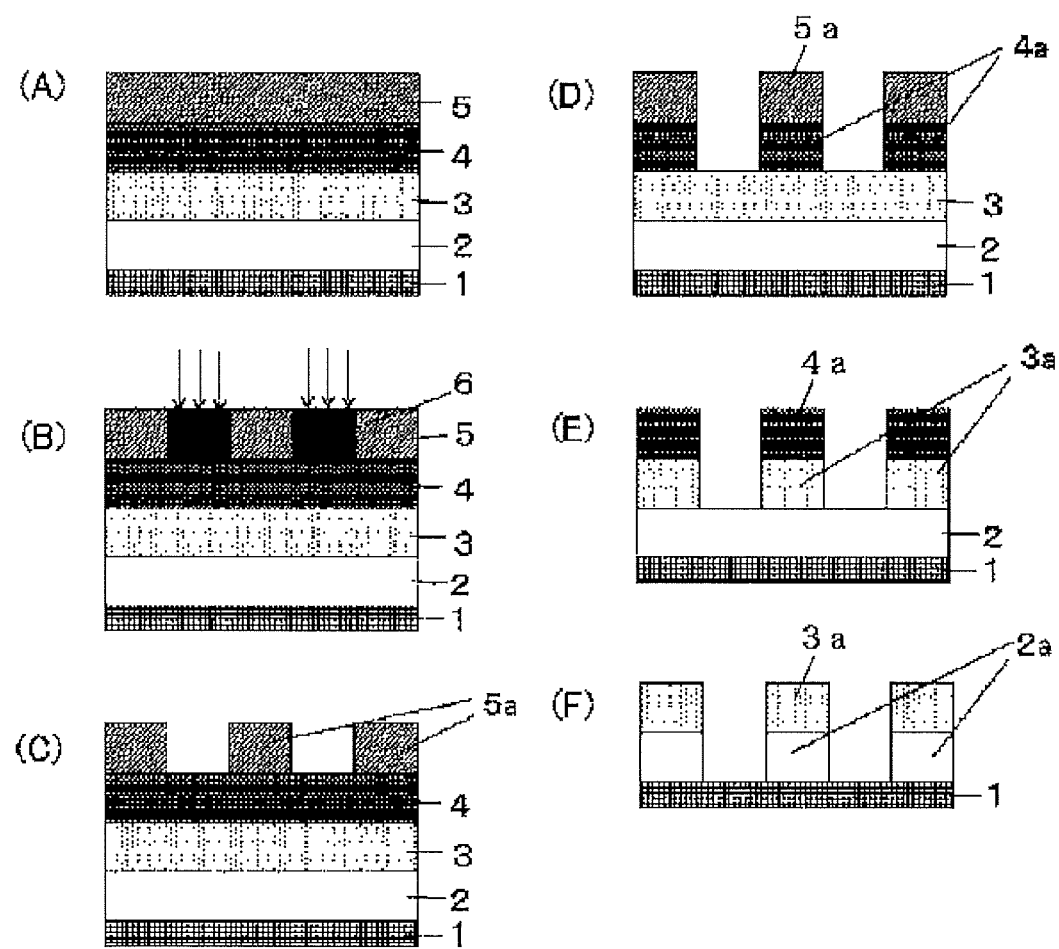
FIG. 2 is an explanatory diagram of an example of a patterning process by the three-layer resist process.

An example of the patterning process by a three layer resist process is shown in FIGS. 2(A) to (F). In the three layer resist process, as shown in FIG. 2(A), on a layer to be processed 2 formed on a substrate 1, an organic film 3 is formed by using the inventive composition for forming an organic film, followed by forming a silicon-containing resist middle layer film 4, and forming a resist upper layer film 5 thereon. Then, as shown in FIG. 2(B), the exposure area 6 of the resist upper layer film 5 is exposed, followed by performing post-exposure baking (PEB). Subsequently, as shown in FIG. 2(C), a resist upper layer film pattern 5a is formed by specify kind of development. Next, as shown in FIG. 2(D), a silicon-containing resist middle layer film pattern 4a is formed by dry etching processing of the silicon-containing resist middle layer film 4 with fluorocarbon base gas using the resist upper layer film pattern 5a as a mask. Then, as shown in FIG. 2(E), subsequent to removing the resist upper layer film pattern 5a, an organic film pattern 3a is formed by oxygen plasma etching of the organic film 3 using the silicon-containing resist middle layer film pattern 4a as a mask. Additionally, as shown in FIG. 2(F), subsequent to removing the silicon-containing resist middle layer film pattern 4a, a pattern 2a is formed by etching processing of the layer to be processed 2 using the organic film pattern 3a as a mask.

In case of forming an inorganic hard mask, the process may be performed by changing the silicon-containing resist middle layer film 4 to the inorganic hard mask; and in case of forming a BARC, the process may be performed by forming the BARC between the silicon-containing resist middle layer film 4 and the resist upper layer film 5. It is possible to continuously perform etching of the BARC preceding to the etching of the silicon-containing resist middle layer film 4. It is also possible to perform etching of the BARC only, followed by etching of the silicon-containing resist middle layer film 4 after changing the etching apparatus, for example.

As described above, the inventive patterning process makes it possible to form a fine pattern on a substrate to be processed with high accuracy by a multilayer resist process.

EXAMPLES

Hereinafter, the present invention will be specifically described by showing Synthesis Examples, Comparative Synthesis Examples, Examples, and Comparative Examples, but the present invention is not limited thereto. Incidentally, as the weight average molecular weight and dispersity, weight average molecular weight (Mw) and number average molecular weight (Mn) are determined in terms of polystyrene by gel permeation chromatography (GPC) using tetrahydrofuran as an eluent, and then the dispersity (Mw/Mn) was determined.

Synthesis Examples: Synthesis of Highly Heat-Resistant Organic Compounds

[Synthesis Example 1] Synthesis of Compound (A1)

A mixture of 200 g of Diol (B1), 800 g of 1,2-dichloroethene, and 76 g of acetyl chloride was heated to reflux for 72 hours. After cooling to room temperature, 400 mL of diisopropyl ether was added thereto. The yielded solid was filtered off, and dried in vacuum to give 211 g of Dichloride (B2).

Into an ice-cooled mixture of 10.2 g of ethynylbenzene and 80 g of toluene, 100 mL of 1 N tetrahydrofuran solution of ethylmagnesium bromide was added, and this was allowed to gradually raise the temperature to room temperature. After addition of 13.2 g of Dichloride (B2), this was heated and stirred at 60° C. for 5 hours. After cooling, dilute hydrochloric acid was added to stop the reaction. This was washed with water, followed by concentration in vacuum to give 16.3 g of the object (A1). The following are analytical results of IR and LC-MS for the synthesized Compound (A1).

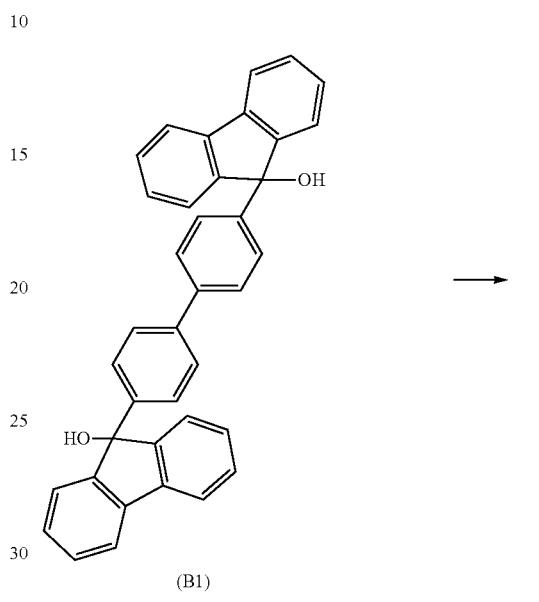

(B1)

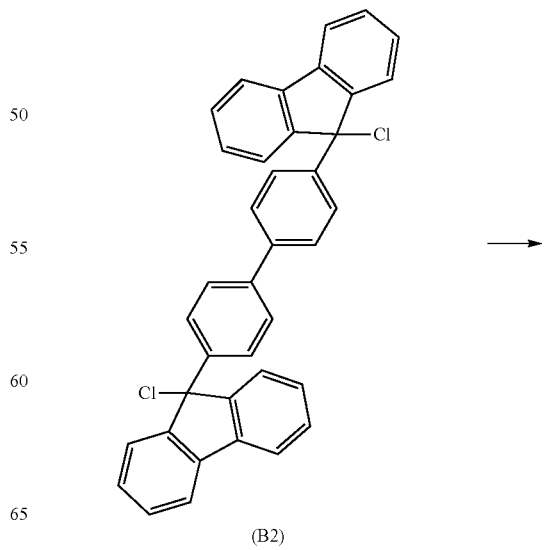

(B2)

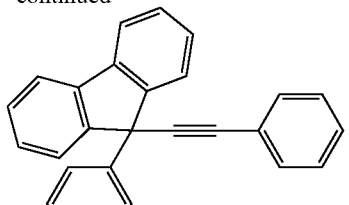

(A1)

IR (D-ATR): ν=3285, 3060, 1600, 1490, 1448, 815, 754, 744, and 690 cm⁻¹

LC-MS (MM-ES Positive/aq.AcONH₄-MeCN): m/z=683 ($C_{54}H_{34}+H^+$).

[Synthesis Example 2] Synthesis of Compound (A2)

Compound (A2) was synthesized by the method in accordance with Synthesis Example 1 except for using 1-ethynyl-4-methoxybenzene instead of ethynylbenzene. The following are analytical results of IR and LC-MS for the synthesized Compound (A2).

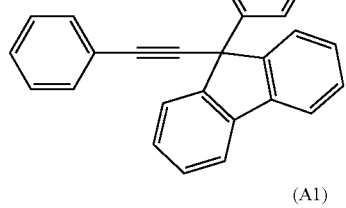

(A2)

IR (D-ATR): ν=3037, 2955, 2933, 2835, 1605, 1509, 1448, 1290, 1248, 1170, 1030, 831, 812, 765, 754, and 736 cm⁻¹

LC-MS (MM-ES Positive/aq.AcONH₄-MeCN): m/z=743 ($C_{56}H_{38}O_2+H^+$).

[Synthesis Example 3] Synthesis of Compound (A3)

To a mixture of 6.9 g of Dichloride (B2) and 50 g of toluene, 100 mL of 0.5 N tetrahydrofuran solution of eth- ylmagnesium bromide was added, and this was refluxed with heating for 200 minutes. After cooling, dilute hydrochloric acid was added to stop the reaction. This was washed with water, followed by concentration in vacuum to give 6.6 g of the compound (A3). The weight average molecular weight (Mw) and dispersity (Mw/Mn) were determined by GPC, and found that Mw=1100 and Mw/Mn=1.74. The following are analytical results of IR and ¹H NMR for the synthesized Compound (A3).

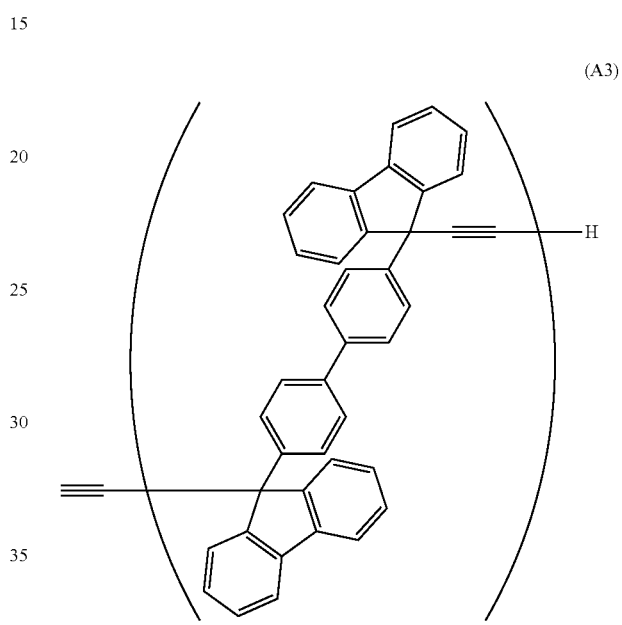

(A3)

IR (D-ATR): ν=3291, 3061, 3036, 1604, 1493, 1475, 1448, 1005, 920, 815, 753, 730, and 650 cm⁻¹

1H NMR (600 MHz, THF-d8) δ (ppm): 2.85-2.90 (2H, HC≡C—), 7.00-7.85 (49H, Ar—H).

[Synthesis Example 4] Synthesis of Compound (A4)

Into an ice-cooled mixture of 11 g of 1,3-diethynylbenzene and 80 g of toluene, 100 mL of 1 N tetrahydrofuran solution of ethylmagnesium bromide was added, and allowed to warm to room temperature. After addition of 23 g of Dichloride (B2), this was heated and stirred at 60° C. for 2 hours. After cooling, dilute hydrochloric acid was added to stop the reaction. This was washed with water and concentrated in vacuum, and then methanol was added thereto. The yielded solid was filtered off, washed with methanol, and dried in vacuum to give 27 g of the object (A4). The weight average molecular weight (Mw) and dispersity (Mw/Mn) were determined by GPC, and found that Mw=2000 and Mw/Mn=1.58.

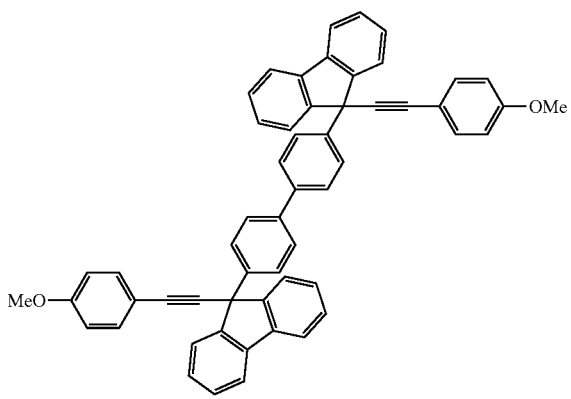

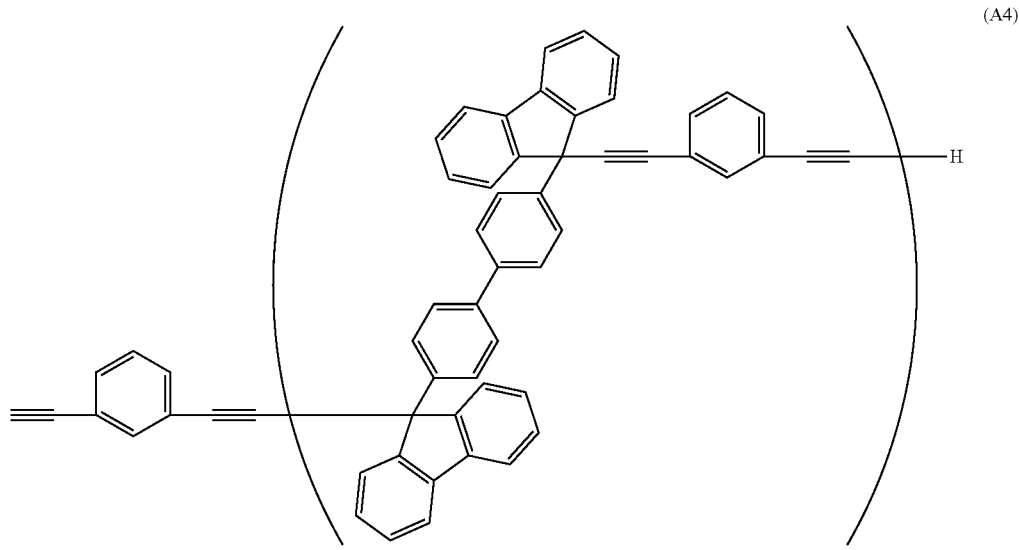

(A4)

The following are analytical results of IR for the synthesized Compound (A4).

IR (D-ATR): ν=3291, 3061, 3028, 1594, 1493, 1475, 1448, 813, 794, 753, and 732 cm$^{-1}$.

[Synthesis Example 5] Synthesis of Compound (A5)

Under an $N_2$ atmosphere, to a mixture of 219 g of bis(4-bromophenyl) ether and 1000 mL of t-butyl methyl ether cooled to −20° C., 500 mL of 2.67 M n-butyl lithium hexane solution was added, and this was stirred at −20° C. for 20 minutes. To this, 229 g of fluoren-9-one (B4) was added. This was allowed to gradually warm to room temperature, and stirred for 4 hours. The reaction was stopped by adding water. This was washed with water and concentrated in vacuum, and subsequently, hexane was added thereto. The yielded solid was filtered off, washed with hexane, and dried in vacuum to give 293 g of Diol (B5).

A mixture of 265 g of Diol (B5), 1000 g of 1,2-dichloroethene, and 157 g of acetyl chloride was stirred at room temperature for 22 hours. To this, 1000 mL of hexane was added. The yielded solid was filtered off and dried in vacuum to give 181 g of Dichloride (B6).

Into an ice-cooled mixture of 10.1 g of 1,3-diethynylbenzene and 50 g of toluene, 50 mL of 1 N tetrahydrofuran solution of ethylmagnesium bromide was added, and this was allowed to gradually warm to room temperature. After addition of 11.4 g of Dichloride (B6), this was warmed to 40° C. and stirred for 4 hours. The reaction was stopped by addition of dilute hydrochloric acid. This was washed with water and concentrated in vacuum, and then methanol was added thereto. The yielded solid was filtered off, washed with methanol, and dried in vacuum to give 13.3 g of the object (A5). The weight average molecular weight (Mw) and dispersity (Mw/Mn) were determined by GPC, and found that Mw=1000 and Mw/Mn=1.17.

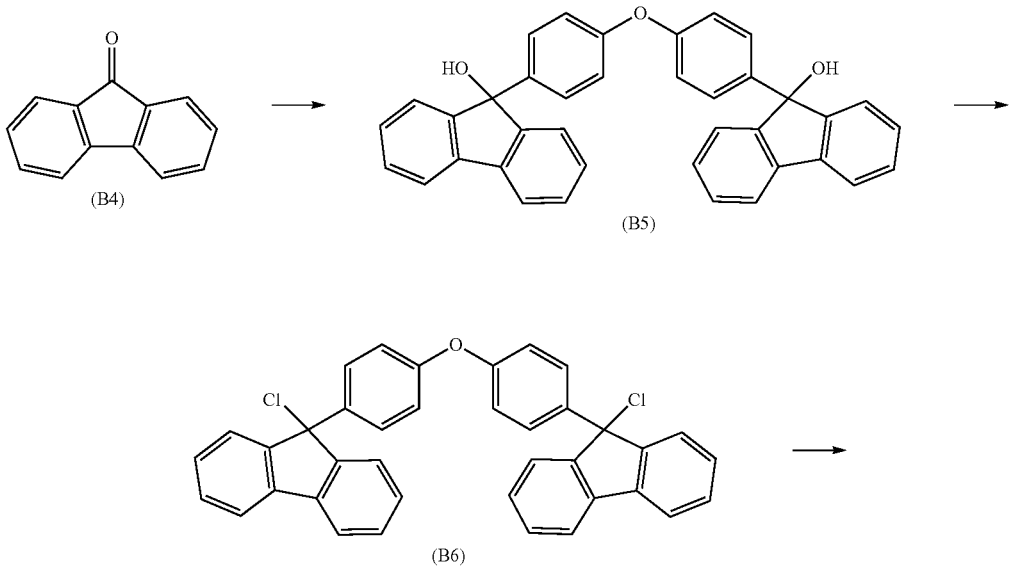

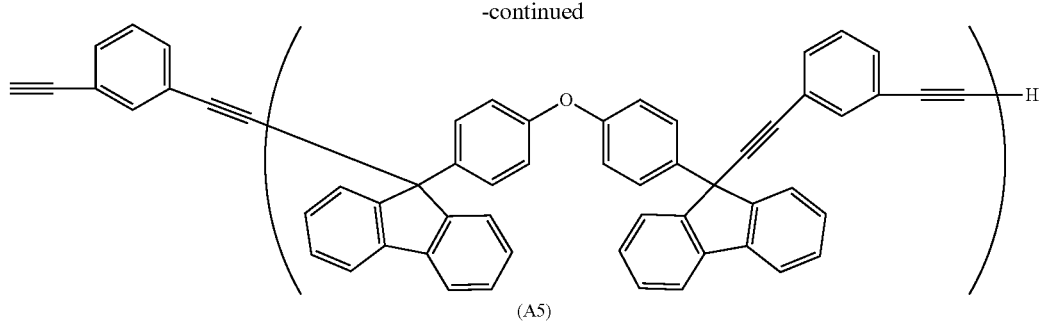

(A5)

The following are analytical results of IR for the synthesized Compound (A5).

IR (D-ATR): ν=3289, 3062, 1594, 1496, 1475, 1448, 1240, 825, 751, and 733 cm$^{-1}$.

[Synthesis Example 6] Synthesis of Compound (A6)

Under an N$_2$ atmosphere, to a mixture of 43.2 g of 2,8-dibromodibenzofuran and 200 mL of t-butyl methyl ether cooled to −20° C., 100 mL of 2.65 M n-butyl lithium hexane solution was added, and this was stirred at −20° C. for 15 minutes. To this, 45.4 g of fluoren-9-one (B4) was added. This was allowed to gradually raise the temperature to room temperature, and stirred at room temperature for 5 hours. The reaction was stopped by adding water. This was washed with water and concentrated in vacuum, and subsequently, heptane was added thereto. The yielded solid was filtered off, washed with heptane, and dried in vacuum to give 60.2 g of Diol (B7).

A mixture of 31.7 g of Diol (B7), 150 g of 1,2-dichloroethene, and 18.8 g of acetyl chloride was warmed to 40° C. and stirred for 18 hours. After cooling to room temperature, 300 mL of hexane was added. The yielded solid was filtered off and dried in vacuum to give 24.9 g of Dichloride (B8).

Into an ice-cooled mixture of 10.5 g of 1,3-diethynylbenzene and 140 g of toluene, 100 mL of 1 N tetrahydrofuran solution of ethylmagnesium bromide was added, and this was allowed to gradually warm to room temperature. After addition of 23.6 g of Dichloride (B8), this was warmed to 40° C. and stirred for 19 hours. After cooling to room temperature, dilute hydrochloric acid was added to stop the reaction. This was washed with water and concentrated in vacuum, and then diisopropyl ether was added thereto. The yielded solid was filtered off, washed with diisopropyl ether, and dried in vacuum to give 21.4 g of the object (A6). The weight average molecular weight (Mw) and dispersity (Mw/Mn) were determined by GPC, and found that Mw=1600 and Mw/Mn=1.44.

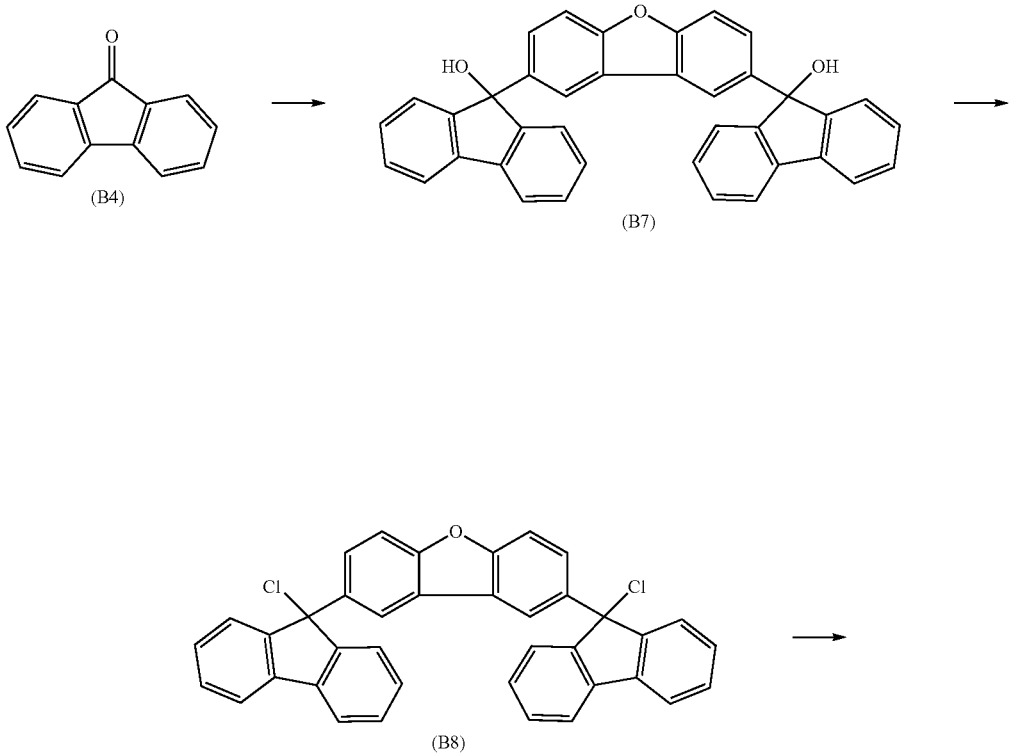

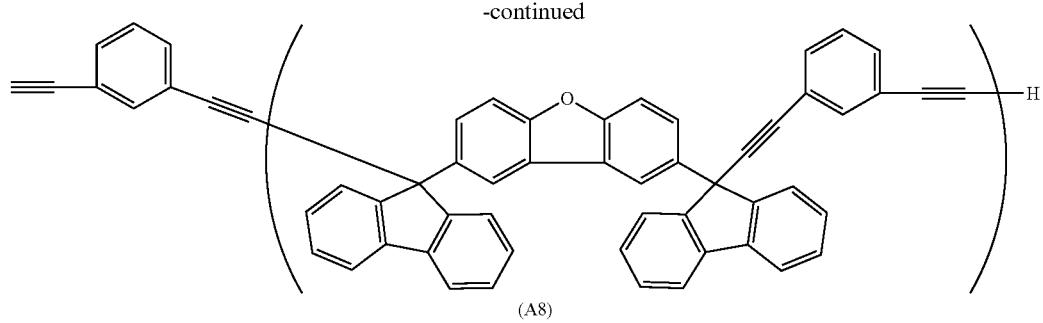

(A8)

The following are analytical results of IR for the synthesized Compound (A6).

IR (D-ATR): ν=3292, 3061, 1594, 1476, 1448, 1205, 812, 793, 746, and 733 cm$^{-1}$.

[Synthesis Example 7] Synthesis of Compound (A7)

Under an $N_2$ atmosphere, to a mixture of 31.1 g of 3,6-dibromo-9-phenylcarbazole and 200 mL of t-butyl methyl ether cooled to −20° C., 100 mL of 1.55 M n-butyl lithium hexane solution was added, and this was stirred at −10° C. for 30 minutes. To this, 26.5 g of fluoren-9-one (B4) was added. This was allowed to gradually warm to room temperature, and stirred for 6 hours. The reaction was stopped by adding water. This was washed with water and concentrated in vacuum, and subsequently, heptane was added thereto. The yielded solid was filtered off, washed with heptane, and dried in vacuum to give 36.7 g of Diol (B9).

A mixture of 18.1 g of Diol (B9), 80 g of 1,2-dichloroethene, and 9.4 g of acetyl chloride was heated to 60° C. and stirred for 21 hours. After cooling to room temperature, 45 mL of diisopropyl ether was added. The yielded solid was filtered off and dried in vacuum to give 12.7 g of Dichloride (B10).

Into an ice-cooled mixture of 5.0 g of 1,3-diethynylbenzene and 60 g of toluene, 48 mL of 1 N tetrahydrofuran solution of ethylmagnesium bromide was added, and this was allowed to gradually raise the temperature to room temperature. After addition of 12.8 g of Dichloride (B10), this was stirred at room temperature for 22 hours. The reaction was stopped by adding dilute hydrochloric acid. This was washed with water and concentrated in vacuum, and then diisopropyl ether was added thereto. The yielded solid was filtered off, washed with diisopropyl ether, and dried in vacuum to give 15.7 g of the object (A7). The weight average molecular weight (Mw) and dispersity (Mw/Mn) were determined by GPC, and found that Mw=1500 and Mw/Mn=1.37.

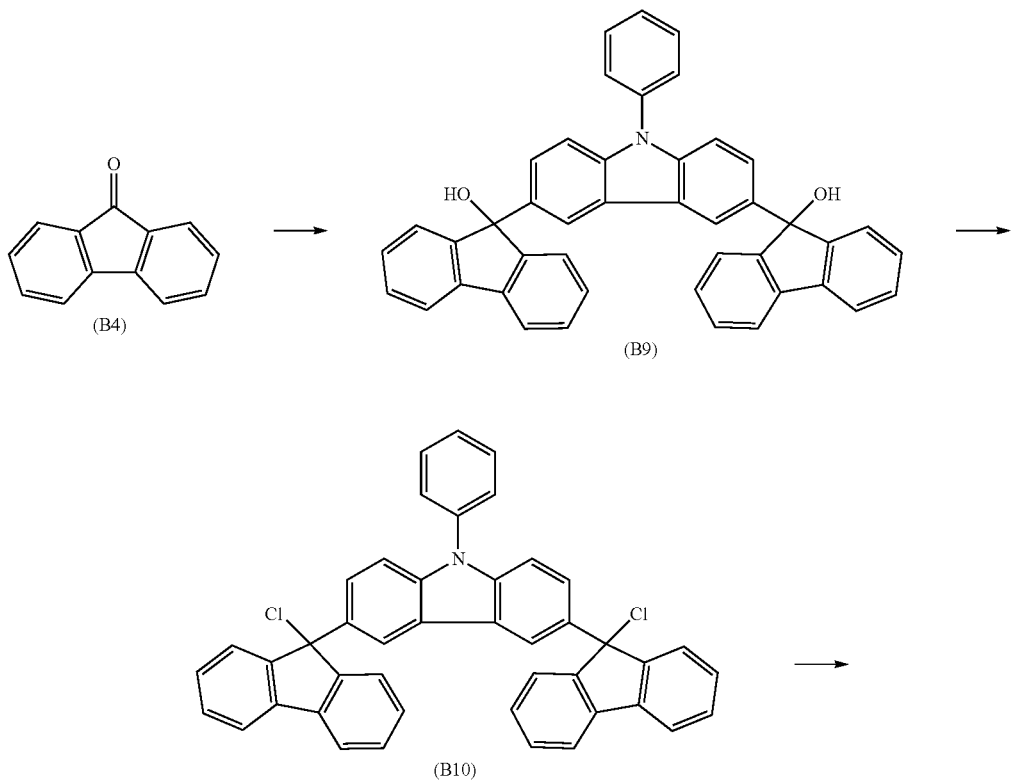

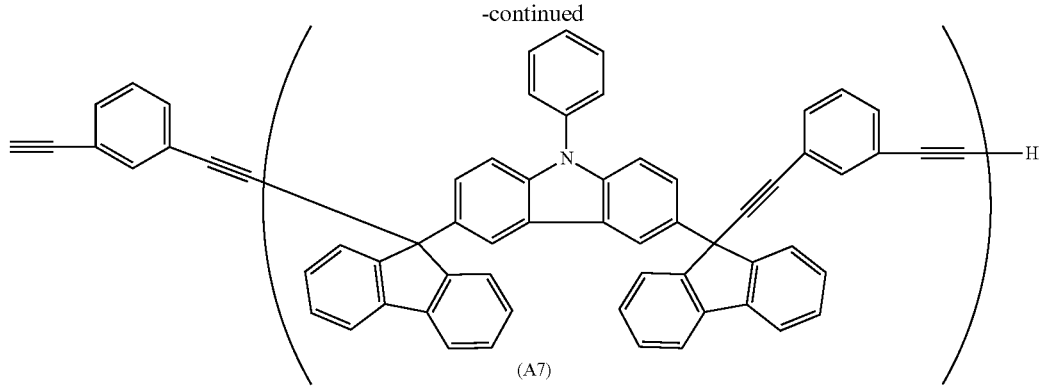

(A7)

The following are analytical results of IR for the synthesized Compound (A7).

IR (D-ATR): ν=3292, 3062, 1596, 1501, 1483, 1475, 1448, 1236, 809, 793, 746, and 732 cm$^{-1}$.

[Synthesis Example 8] Synthesis of Compound (A8)

Under an N$_2$ atmosphere, to a mixture of 28.8 g of 3,3'-dibromo-4,4'-dimethoxybiphenyl and 200 mL of t-butyl methyl ether cooled to −20° C., 100 mL of 1.55 M n-butyl lithium hexane solution was added, and this was stirred at −20° C. for 10 minutes. To this, 26.5 g of fluoren-9-one (B4) was added. This was allowed to gradually warm to room temperature, and stirred for 4 hours. The reaction was stopped by adding water. This was washed with water and concentrated in vacuum, and subsequently, heptane was added thereto. The yielded solid was filtered off, washed with heptane, and dried in vacuum to give 36.0 g of Diol (B11).

A mixture of 11.5 g of Diol (B11), 50 g of 1,2-dichloroethene, and 6.3 g of acetyl chloride was heated to 60° C. and stirred for 22 hours. After cooling to room temperature, 30 mL of hexane was added. The yielded solid was filtered off and dried in vacuum to give 6.7 g of Dichloride (B12).

Into an ice-cooled mixture of 2.1 g of 1,3-diethynylbenzene and 30 g of toluene, 20 mL of 1 N tetrahydrofuran solution of ethylmagnesium bromide was added, and this was allowed to gradually warm to room temperature. After addition of 5.1 g of Dichloride (B12), this was heated to 60° C. and stirred for 4 hours. After cooling to room temperature, dilute hydrochloric acid was added to stop the reaction. This was washed with water and concentrated in vacuum, and then diisopropyl ether was added thereto. The yielded solid was filtered off, washed with diisopropyl ether, and dried in vacuum to give 4.2 g of the object (A8). The weight average molecular weight (Mw) and dispersity (Mw/Mn) were determined by GPC, and found that Mw=2100 and Mw/Mn=1.64.

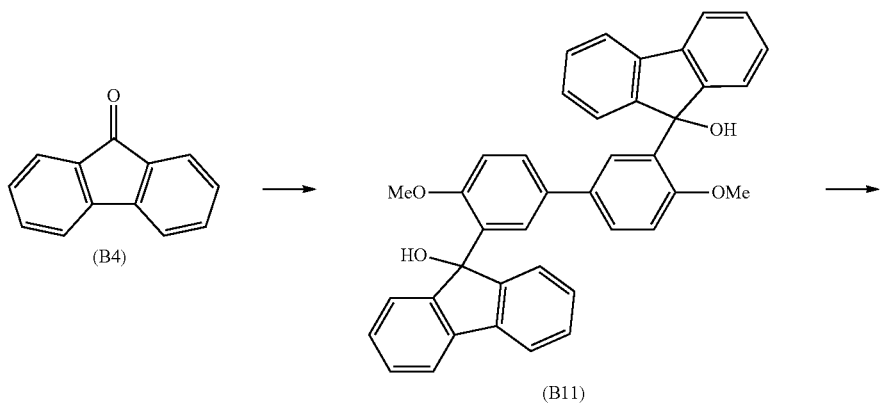

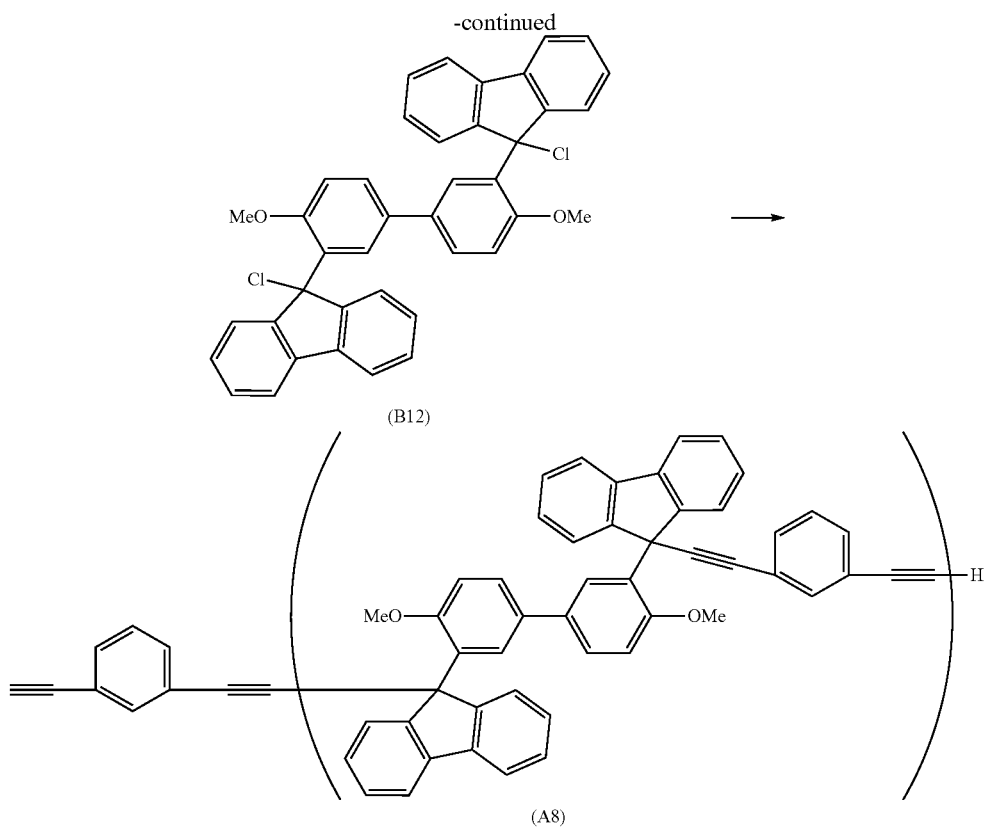

The following are analytical results of IR for the synthesized Compound (A8).

IR (D-ATR): ν=3289, 3060, 2933, 2833, 1594, 1487, 1475, 1448, 1251, 1023, 811, 794, 750, and 733 cm$^{-1}$.

[Synthesis Example 9] Synthesis of Compound (A9)

Under an $N_2$ atmosphere, to a mixture of 42.9 g of 5,5'-dibromo-2,2'-bithiophene and 200 mL of t-butyl methyl ether cooled to −20° C., 100 mL of 2.65 M n-butyl lithium hexane solution was added, and this was stirred at −20° C. for 20 minutes. To this, 45.4 g of fluoren-9-one (B4) was added. This was allowed to gradually warm to room temperature, and stirred for 5 hours. The reaction was stopped by adding water. This was washed with water and concentrated in vacuum, and subsequently, hexane was added thereto. The yielded solid was filtered off, washed with hexane, and dried in vacuum to give 50.2 g of Diol (B13).

A mixture of 21.1 g of Diol (B13), 100 g of 1,2-dichloroethene, and 12.6 g of acetyl chloride was heated to 60° C. and stirred for 4 hours. After cooling to room temperature, 150 mL of hexane was added. The yielded solid was filtered off and dried in vacuum to give 18.6 g of Dichloride (B14).

Into an ice-cooled mixture of 5.0 g of 1,3-diethynylbenzene and 30 g of toluene, 25 mL of 1 N tetrahydrofuran solution of ethylmagnesium bromide was added, and this was allowed to gradually warm to room temperature. After addition of 5.6 g of Dichloride (B14), this was stirred at room temperature for 7 hours. The reaction was stopped by adding dilute hydrochloric acid. This was washed with water and concentrated in vacuum, and then methanol was added thereto. The yielded solid was filtered off, washed with methanol, and dried in vacuum to give 5.5 g of the object (A9). The weight average molecular weight (Mw) and dispersity (Mw/Mn) were determined by GPC, and found that Mw=5800 and Mw/Mn=3.21.

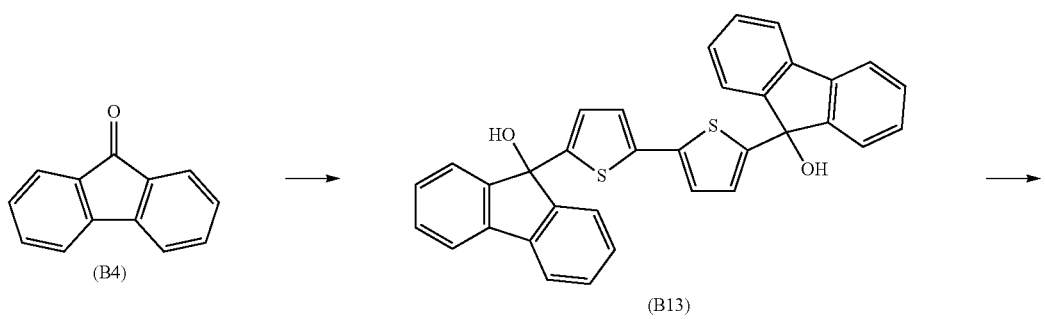

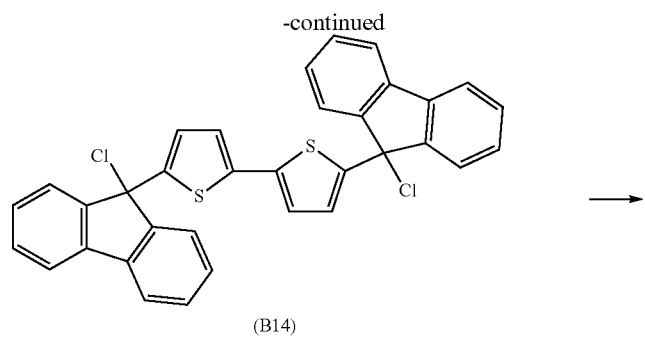

(B14)

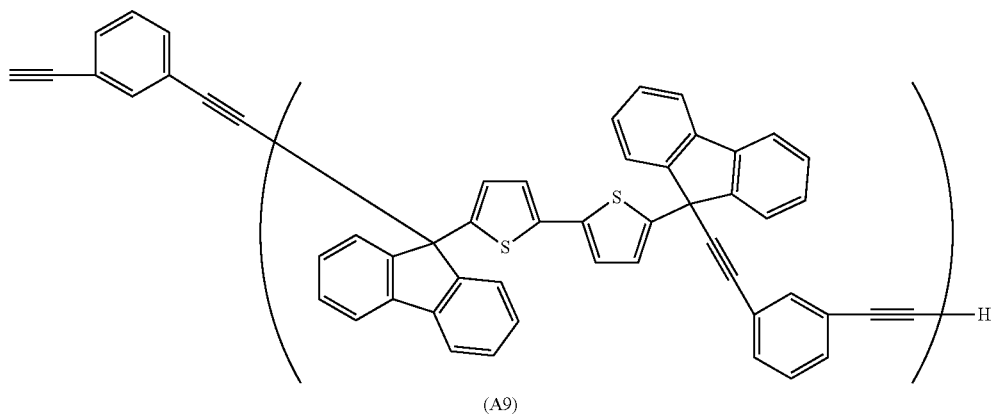

(A9)

The following are analytical results of IR for the synthesized Compound (A9).

IR (D-ATR): v=3294, 3060, 1593, 1475, 1446, 1349, 895, 794, 740, and 732 cm$^{-1}$.

[Synthesis Example 10] Synthesis of Compound (A10)

Under an $N_2$ atmosphere, to a mixture of 24.2 g of 4,4'-dibromobiphenyl, 100 mL of t-butyl methyl ether, and 100 mL of cyclopentyl methyl ether cooled to −20° C., 100 mL of 2.67 M n-butyl lithium hexane solution was added, and this was stirred at −20° C. for 20 minutes. To this, 35.67 g of 4,4'-dimethoxybenzophenone (B15) was added. This was allowed to gradually warm to room temperature, and stirred for 4 hours. The reaction was stopped by adding water. This was washed with water and concentrated in vacuum, and subsequently, heptane was added thereto. The yielded solid was filtered off, washed with heptane, and dried in vacuum to give 42.2 g of Diol (B16).

A mixture of 19.2 g of Diol (B16), 80 g of 1,2-dichloroethene, and 9.42 g of acetyl chloride was warmed to 40° C. and stirred for 23 hours. After cooling to room temperature, 80 mL of diisopropyl ether was added. The yielded solid was filtered off and dried in vacuum to give 18.4 g of Dichloride (B17).

Into an ice-cooled mixture of 4.21 g of 1,3-diethynylbenzene and 80 g of toluene, 40 mL of 1 N tetrahydrofuran solution of ethylmagnesium bromide was added, and this was allowed to gradually raise the temperature to room temperature. After addition of 11.3 g of Dichloride (B17), this was stirred at room temperature for 22 hours. The reaction was stopped by adding dilute hydrochloric acid. This was washed with water and concentrated in vacuum, and then methanol was added thereto. The yielded solid was filtered off, washed with methanol, and dried in vacuum to give 11.3 g of the compound (A10). The weight average molecular weight (Mw) and dispersity (Mw/Mn) were determined by GPC, and found that Mw=2100 and Mw/Mn=1.40.

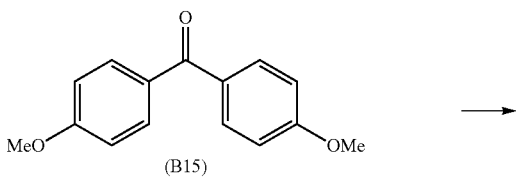

(B15)

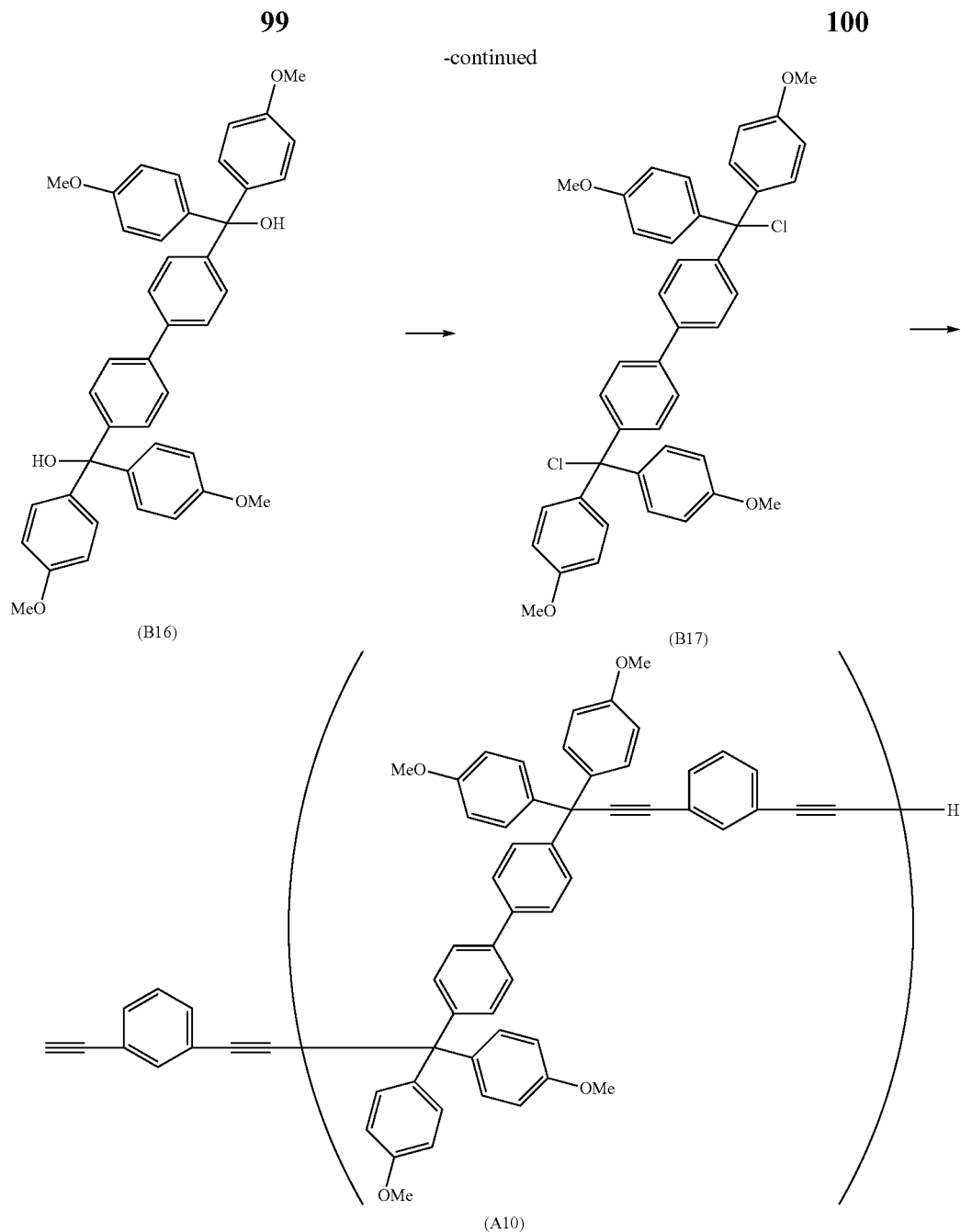
(B16) (B17) (A10)

The following are analytical results of IR for the synthesized Compound (A10).

IR (D-ATR): ν=3290, 3032, 2997, 2951, 2930, 2904, 2833, 1606, 1506, 1440, 1298, 1250, 1177, 1034, 824, 795, and 731 cm$^{-1}$.

[Synthesis Example 11] Synthesis of Compound (A11)

Under an N$_2$ atmosphere, to a mixture of 43.5 g of bis(4-bromophenyl) ether and 200 mL of t-butyl methyl ether cooled to −20° C., 100 mL of 2.65 M n-butyl lithium hexane solution was added, and this was stirred at −20° C. for 30 minutes. To this, 49.4 g of xanthone (B18) was added. This was allowed to gradually warm to room temperature, and stirred for 4 hours. The reaction was stopped by adding water. This was washed with water and concentrated in vacuum, and subsequently, heptane was added thereto. The yielded solid was filtered off, washed with heptane, and dried in vacuum to give 63.4 g of Diol (B19).

A mixture of 33.8 g of Diol (B19), 150 g of 1,2-dichloroethene, and 18.8 g of acetyl chloride was warmed to 40° C. and stirred for 24 hours. After cooling to room temperature, 300 mL of heptane was added. The yielded solid was filtered off and dried in vacuum to give 18.5 g of Dichloride (B20).

Into an ice-cooled mixture of 5.26 g of 1,3-diethynylbenzene and 80 g of toluene, 50 mL of 1 N tetrahydrofuran solution of ethylmagnesium bromide was added, and this was allowed to gradually warm to room temperature. After addition of 12.5 g of Dichloride (B20), this was stirred at room temperature for 24 hours. The reaction was stopped by adding dilute hydrochloric acid. This was washed with water and concentrated in vacuum, and then heptane was added thereto. The yielded solid was filtered off, washed with heptane, and dried in vacuum to give 10.4 g of the object (A11). The weight average molecular weight (Mw) and dispersity (Mw/Mn) were determined by GPC, and found that Mw=1700 and Mw/Mn=1.67.

100 mL of hexane was added thereto. The yielded solid was filtered off, and dried in vacuum to give 7.2 g of Dichloride (B22).

Into an ice-cooled mixture of 1.6 g of 1,3-diethynylbenzene and 20 g of toluene, 15 mL of 1 N tetrahydrofuran solution of ethylmagnesium bromide was added, and this

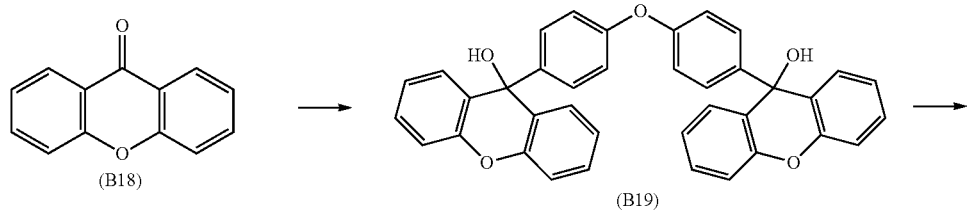

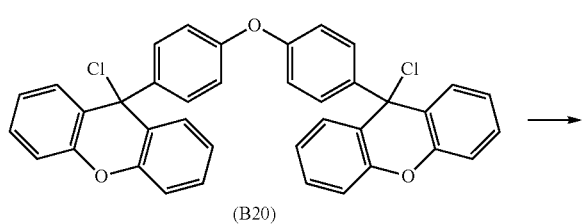

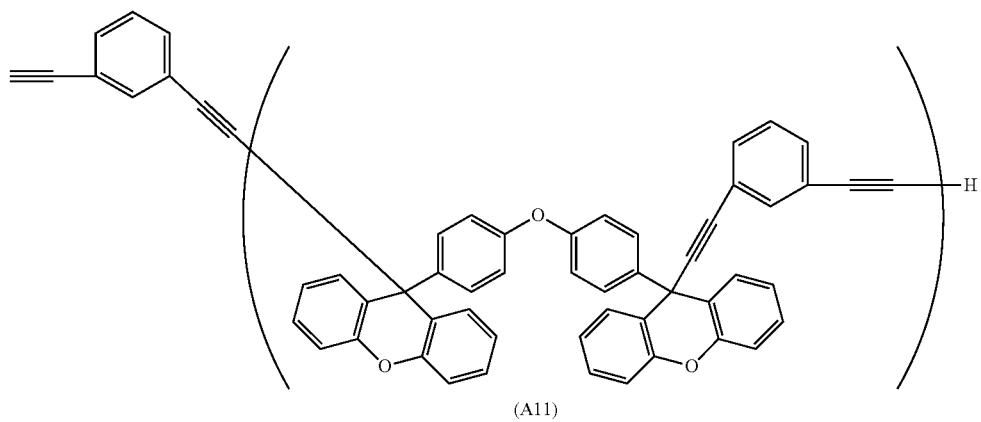

The following are analytical results of IR for the synthesized Compound (A11). IR (D-ATR): ν=3291, 3036, 1598, 1495, 1445, 1242, 825, and 752 cm⁻¹.

[Synthesis Example 12] Synthesis of Compound (A12)

A mixture of 9.3 g of Diol (B21), 60 g of 1,2-dichloroethene, and 5.0 g of acetyl chloride was heated to 60° C. and stirred for 20 hours. After cooling to room temperature, was allowed to gradually warm to room temperature. After addition of 3.4 g of Dichloride (B22), this was stirred at room temperature for 5 hours. The reaction was stopped by adding dilute hydrochloric acid. This was washed with water and concentrated in vacuum, and then methanol was added thereto. The yielded solid was filtered off, washed with methanol, and dried in vacuum to give 3.7 g of the compound (A12). The weight average molecular weight (Mw) and dispersity (Mw/Mn) were determined by GPC, and found that Mw=2500 and Mw/Mn=2.38.

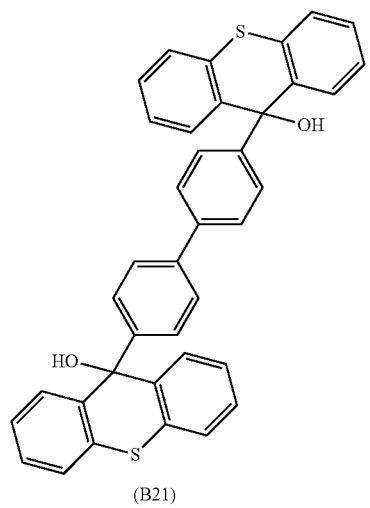

(B21)

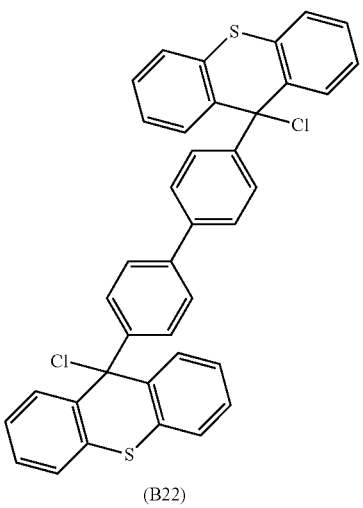

(B22)

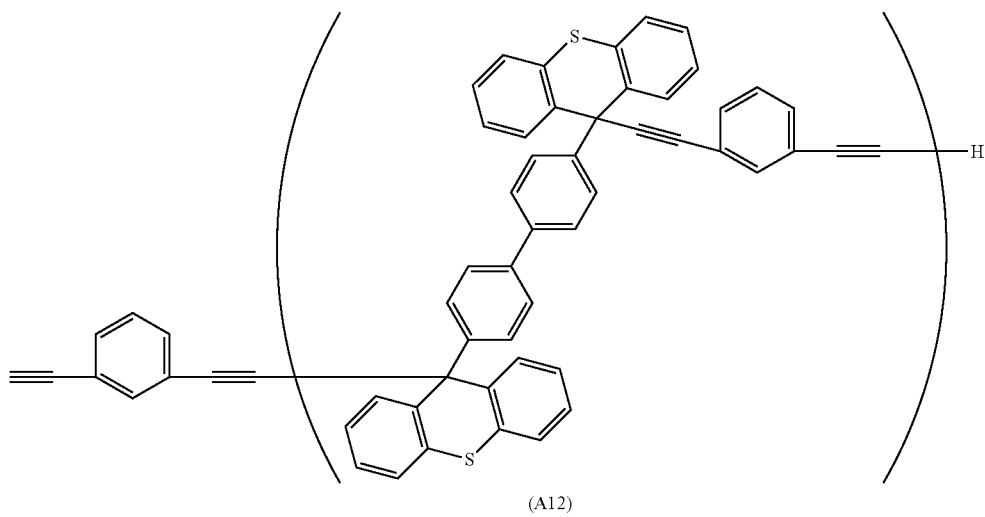

(A12)

The following are analytical results of IR for the synthesized Compound (A12).

IR (D-ATR): ν=3291, 3058, 3027, 1591, 1491, 1474, 1457, 1440, 1393, 1189, 816, 794, and 752 cm$^{-1}$.

[Synthesis Example 13] Synthesis of Compound (A13)

Under an $N_2$ atmosphere, to a mixture of 42.6 g of tris(4-bromophenyl)amine and 300 mL of t-butyl methyl ether cooled to −20° C., 100 mL of 2.65 M n-butyl lithium hexane solution was added. After stirring at −20° C. for 30 minutes, 45.4 g of fluoren-9-one (B4) was added. This was allowed to gradually warm to room temperature, and was stirred at for 5 hours. The reaction was stopped by adding water. This was washed with water and concentrated in vacuum, and subsequently, heptane was added thereto. The yielded solid was filtered off, washed with heptane, and dried in vacuum to give 33.3 g of Triol (B23).

A mixture of 23.6 g of Triol (B23), 200 g of 1,2-dichloroethene, and 14.1 g of acetyl chloride was stirred at room temperature for 19 hours. To this, 150 mL of hexane was added. The yielded solid was filtered off and dried in vacuum to give 22.0 g of Trichloride (B24).

Into an ice-cooled mixture of 9.7 g of 1,3-diethynylbenzene and 40 g of toluene, 46 mL of 1 N tetrahydrofuran solution of ethylmagnesium bromide was added, and this was allowed to gradually warm to room temperature. After addition of 10.0 g of Trichloride (B24), this was stirred at room temperature for 4 hours. The reaction was stopped by adding dilute hydrochloric acid. This was washed with water and concentrated in vacuum, and then methanol was added thereto. The yielded solid was filtered off, washed with methanol, and dried in vacuum to give 13.4 g of the object (A13). The weight average molecular weight (Mw) and dispersity (Mw/Mn) were determined by GPC, and found that Mw=2100 and Mw/Mn 1.37.

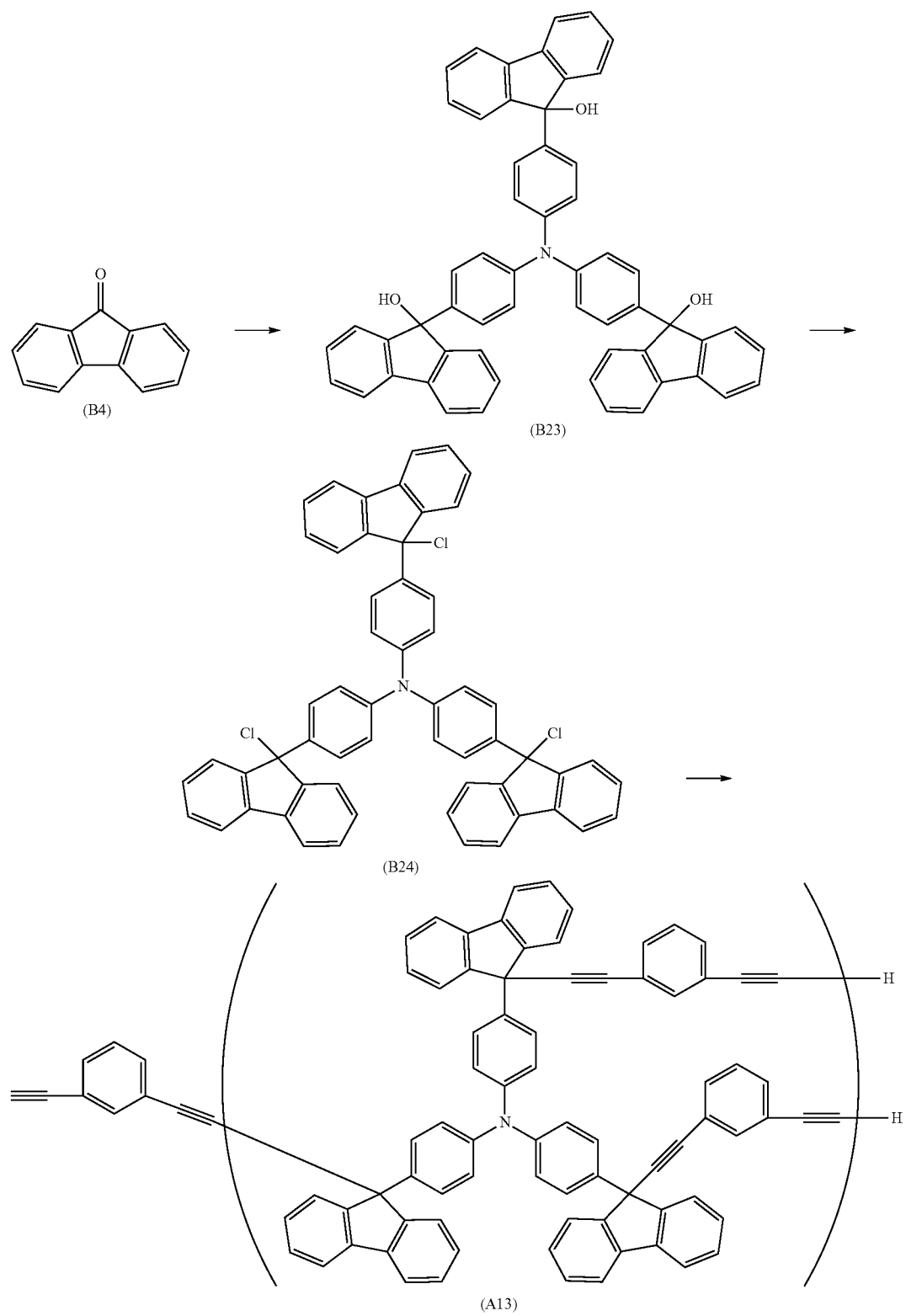
The following are analytical results of IR for the synthesized Compound (A13).
IR (D-ATR): ν=3289, 3060, 3034, 1595, 1502, 1447, 1280, 823, 752, 732, and 685 cm$^{-1}$.
[Synthesis Example 14] Synthesis of Compound (A14)
Into an ice-cooled mixture of 2.0 g of ethynylbenzene and 20 g of toluene, 20 mL of 1 N tetrahydrofuran solution of ethylmagnesium bromide was added, and this was allowed to gradually warm to room temperature. After addition of 4.4 g of Trichloride (B24), this was stirred at room temperature for 6 hours. The reaction was stopped by adding dilute hydrochloric acid. This was washed with water and concentrated in vacuum, and then hexane was added thereto. The yielded solid was filtered off, washed with hexane, and dried in vacuum to give 4:9 g of the object (A14).

(A14)

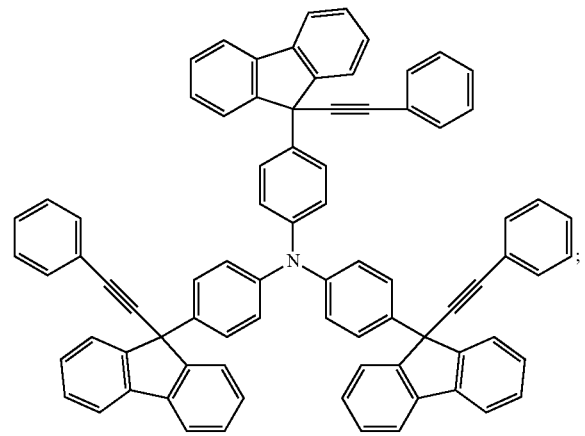

The following are analytical results of IR and LC-MS for the synthesized Compound (A14).

IR (D-ATR): ν=3058, 1599, 1503, 1447, 1280, 824, 754, 743, and 690 cm$^{-1}$

LC-MS (MM-ES Positive/aq.AcONH$_4$-MeCN): m/z=1038 ($C_{81}H_{51}N+H^+$).

[Synthesis Example 15] Synthesis of Compound (A15)

A mixture of 7.0 g of Diol (B25), 50 g of 1,2-dichloroethene, and 3.0 g of acetyl chloride was stirred at room temperature for 22 hours. To this, 45 mL of hexane was added. The yielded solid was filtered off, and dried in vacuum to give 3.9 g of Dichloride (B26).

Into an ice-cooled mixture of 1.3 g of 1,3-diethynylbenzene and 20 g of toluene, 12 mL of 1 N tetrahydrofuran solution of ethylmagnesium bromide was added, and this was allowed to gradually warm to room temperature. After addition of 3.8 g of Dichloride (B26), this was warmed to 40° C. and stirred for 22 hours. The reaction was stopped by adding dilute hydrochloric acid. This was washed with water and concentrated in vacuum, and then methanol was added thereto. The yielded solid was filtered off, washed with methanol, and dried in vacuum to give 3.4 g of the object (A15). The weight average molecular weight (Mw) and dispersity (Mw/Mn) were determined by GPC, and found that Mw=2400 and Mw/Mn=1.57.

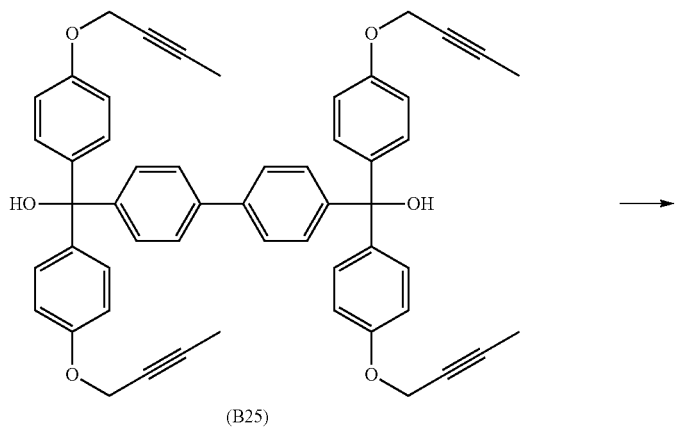

(B25)

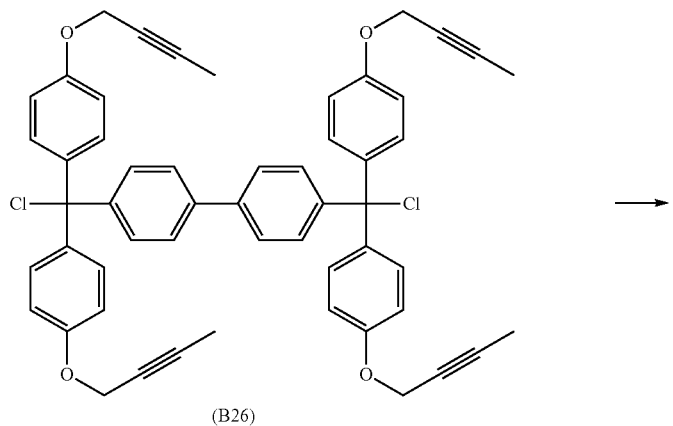

(B26)

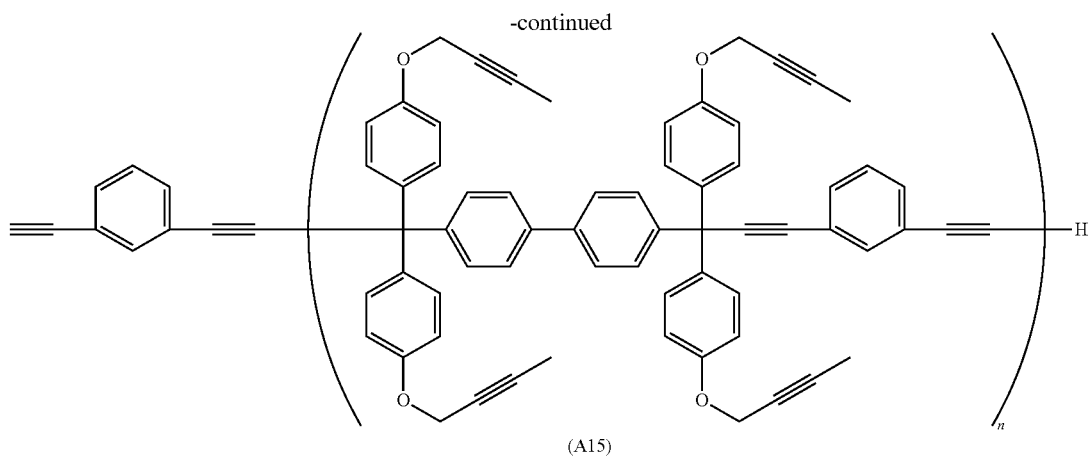

(A15)

The following are analytical results of IR for the synthesized Compound (A15).

IR (D-ATR): ν=3284, 3035, 2917, 2858, 2301, 2228, 1606, 1505, 1448, 1221, 1005, and 821 cm$^{-1}$.

[Synthesis Example 16] Synthesis of Compound (A16)

A mixture of 47.9 g of 3,5-dibromoanisole (B27), 36.3 g of 2-methyl-3-butyn-2-ol, 1.71 g cupper iodide, 150 g of triethylamine, 75 g of tetrahydrofuran, and 6.32 g dichlorobis(triphenylphosphine)palladium (II) was heated to 60° C. and stirred for 7 hours. This was cooled to room temperature and filtered. The filtrate was concentrated in vacuum, and then hexane was added thereto. The yielded solid was filtered off, washed with hexane, and dried in vacuum to give 41.4 g of Diol (B28).

A mixture of 35.0 g of Diol (B28), 2.06 g of sodium hydroxide, and 150 g of toluene was heated to 110° C. and stirred for 2 hours. This was cooled to room temperature, and then washed with water and concentrated in vacuum. The obtained solid was purified by column chromatography [silica gel N60 (350 g), hexane:ethyl acetate=15:1] to give 4.71 g of Diethynyl compound (B29).

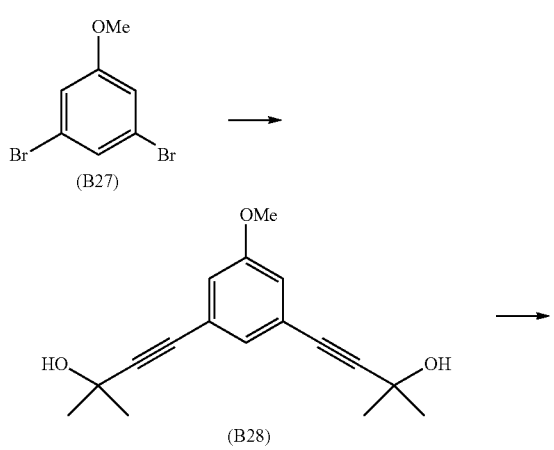

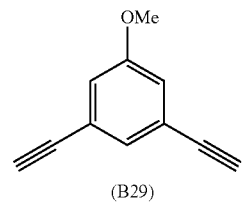

(B29)

The following are analytical results of IR and $^1$H NMR for the synthesized Compound (B29).

IR (D-ATR): ν=3276, 3075, 3000, 2960, 2940, 2838, 1580, 1448, 1323, 1294, 1157, 1060, 881, and 858 cm$^{-1}$ 1H NMR (600 MHz, DMSO-d6) δ (ppm): 7.11 (dd, J=1.7, 1.7 Hz, 1H), 7.06 (d, J=1.7 Hz, 2H), 4.26 (s, 2H), 3.77 s, 3H).

Into an ice-cooled mixture of 2.6 g of Diethynyl compound (B29) and 30 g of toluene, 20 mL of 1 N tetrahydrofuran solution of ethylmagnesium bromide was added, and this was allowed to gradually warm to room temperature. After addition of 4.7 g of Dichloride (B6), this was warmed to 40° C. and stirred for 5 hours. After cooling to room temperature, dilute hydrochloric acid was added to stop the reaction. This was washed with water and concentrated in vacuum, and then diisopropyl ether was added thereto. The yielded solid was filtered off, washed with methanol, and dried in vacuum to give 4.5 g of the object (A16). The weight average molecular weight (Mw) and dispersity (Mw/Mn) were determined by GPC, and found that Mw=2000 and Mw/Mn=1.37.

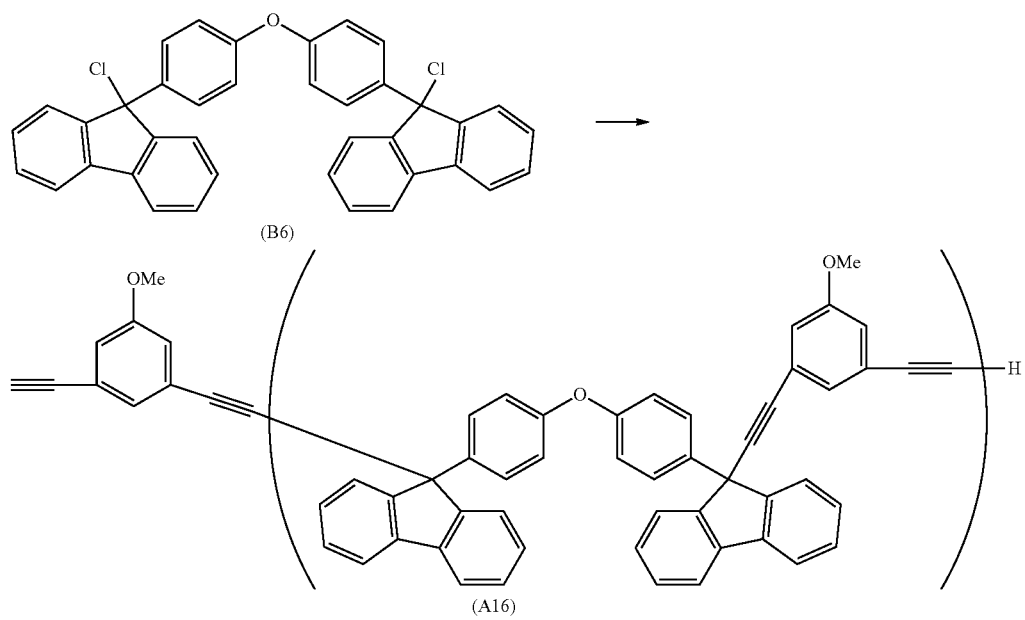

The following are analytical results of IR for the synthesized Compound (A16).

IR (D-ATR): ν=3289, 3063, 2967, 2934, 2838, 1580, 1496, 1448, 1240, 1014, 849, 749, and 728 cm$^{-1}$.

[Synthesis Example 17] Synthesis of Compound (A17)

A mixture of 53.2 g of 2,4-dibromoanisole (B30), 40.4 g of 2-methyl-3-butyn-2-ol, 3.81 g of cupper iodide, 150 g of triethylamine, 75 g of tetrahydrofuran, and 14.0 g of dichloro-bis(triphenylphosphine)palladium (II) was heated to 60° C. and stirred for 7 hours. This was cooled to room temperature and filtered, and the filtrate was concentrated in vacuum. Then, the obtained oily material was purified by column chromatography [silica gel (600 g), hexane:ethyl acetate=2:1] to give 50.9 g of Diol (B31).

A mixture of 50.2 g of Diol (B31), 29.4 g of sodium hydroxide, and 200 g of toluene was heated to 110° C. and stirred for 5 hours. This was cooled to room temperature, and then washed with water and concentrated in vacuum. The obtained solid was purified by column chromatography [silica gel N60 (500 g), hexane:ethyl acetate=20:1] to give 10.1 g of Diethynyl compound (B32).

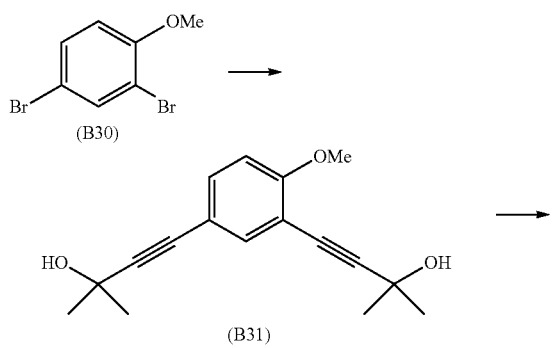

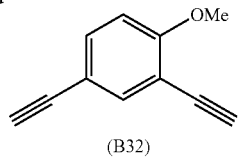

The following are analytical results of IR, $^1$H NMR, and LC-MS for the synthesized Compound (B32).

IR (D-ATR): ν=3304, 3271, 3009, 2974, 2948, 2896, 2843, 1598, 1496, 1290, 1259, 1118, 1020, 897, 821, and 812 cm$^{-1}$ $^1$H NMR (600 MHz, DMSO-d6) δ (ppm): 7.48-7.46 (m, 2H), 7.06 (d, J=8.7 Hz, 1H), 4.29 (s, 1H), 4.07 (s, 1H), 3.83 (s, 3H)

LC-MS (MM-ES Positive/aq.AcONH$_4$-MeCN): m/z=157 (C$_{11}$H$_8$O+H$^+$).

Into an ice-cooled mixture of 2.6 g of Diethynyl compound (B32) and 30 g of toluene, 20 mL of 1 N tetrahydrofuran solution of ethylmagnesium bromide was added, and this was allowed to gradually warm to room temperature. After addition of 4.7 g of Dichloride (B6), this was warmed to 40° C. and stirred for 4 hours. After cooling to room temperature, dilute hydrochloric acid was added to stop the reaction. This was washed with water and concentrated in vacuum, and then methanol was added thereto. The yielded solid was filtered off, washed with methanol, and dried in vacuum to give 6.0 g of the object (A17). The weight average molecular weight (Mw) and dispersity (Mw/Mn) were determined by GPC, and found that Mw=1800 and Mw/Mn=1.55.

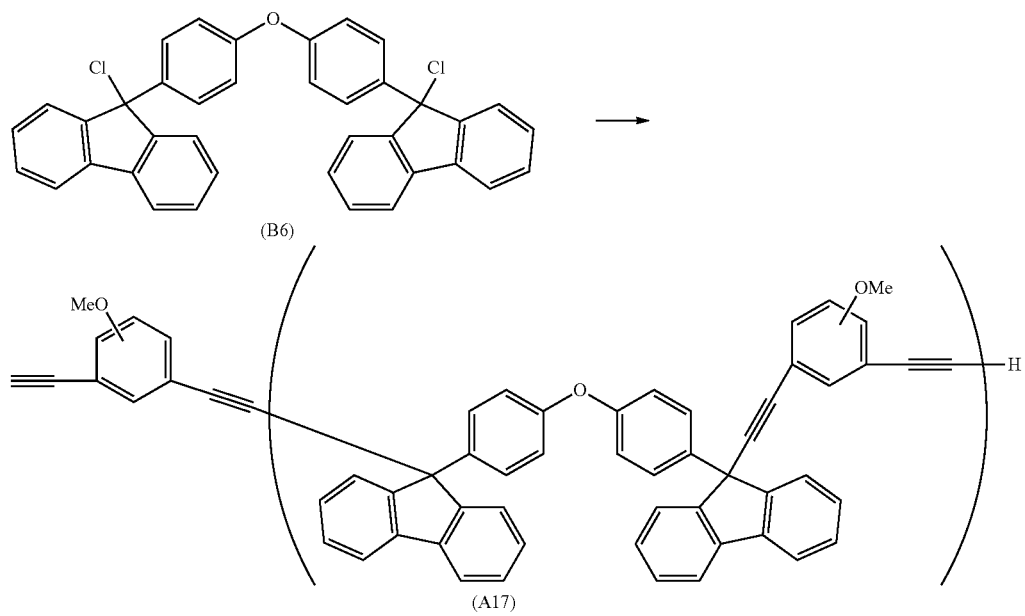

The following are analytical results of IR for the synthesized Compound (A17).

IR (D-ATR): ν=3288, 3062, 2940, 2840, 1597, 1495, 1448, 1243, 1016, 818, 744, and 734 cm$^{-1}$.

[Synthesis Example 18] Synthesis of Compound (A18)

In nitrogen atmosphere, 58.7 g of Compound (B33), 41.3 g of fluoren-9-one, 5 ml of 3-mercaptopropionic acid, and 300 ml of 1,2-dichloroethane were mixed at the bulk temperature of 70° C. to a homogeneous solution. Then, 10 ml of methanesulfonic acid was slowly added thereto, and the reaction was performed at the bulk temperature of 70° C. for 24 hours. After cooling to room temperature, 500 g of methyl isobutyl ketone was added thereto. The organic layer was washed with 100 g of pure water for five times, and dried in vacuum. To the residue, 200 g of THF was added to form a homogeneous solution, and then, the polymer was reprecipitated from 1500 g of methanol. The precipitated polymer was recovered by filtration, followed by washing with 800 g of methanol twice. The recovered polymer was dried at 70° C. in vacuum to give Compound (A18).

The weight average molecular weight (Mw) and dispersity (Mw/Mn) were determined by GPC, and the following results were obtained.

(A18): Mw=3500, Mw/Mn=2.94.

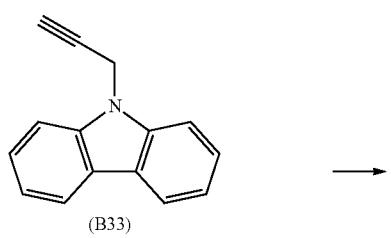

(B33)

-continued

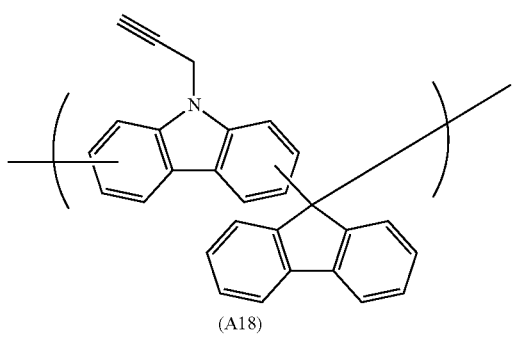

(A18)

[Synthesis Example 19] Synthesis of Compound (A19)

In nitrogen atmosphere, 70.7 g of Compound (B33), 29.3 g of benzaldehyde, 5 ml of 3-mercaptopropionic acid, and 300 ml of 1,2-dichloroethane were mixed at the bulk temperature of 70° C. to a homogeneous solution. Then, 10 ml of methanesulfonic acid was slowly added thereto, and the reaction was performed at the bulk temperature of 70° C. for 24 hours. After cooling to room temperature, 500 g of methyl isobutyl ketone was added thereto. The organic layer was washed with 100 g of pure water five times, and dried in vacuum. To the residue, 200 g of THF was added to form a homogeneous solution, and then, the polymer was reprecipitated from 1500 g of methanol. The precipitated polymer was recovered by filtration, followed by washing with 800 g of methanol twice. The recovered polymer was dried at 70° C. in vacuum to give Compound (A19).

The weight average molecular weight (Mw) and dispersity (Mw/Mn) were determined by GPC, and the following results were obtained.

(A19): Mw=3700, Mw/Mn=2.87.

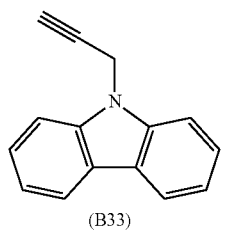

(B33)

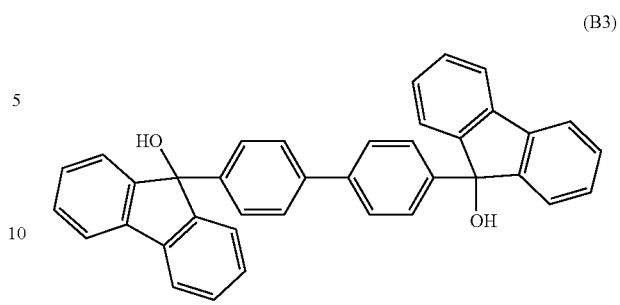

(B3)

Biphenyl Derivative (B3):
IR (D-ATR): ν=3539, 3064, 3039, 1605, 1495, 1447, 1164, 1030, 909, 820, 771, 754, and 736 cm$^{-1}$.
$^1$H-NMR (600 MHz in DMSO-d$_6$): δ=6.34 (2H, —OH, s), 7.24 (4H, t), 7.27 (8H, d), 7.36 (4H, t-t), 7.45 (4H, d), and 7.81 (4H, d) ppm.
$^{13}$C-NMR (150 MHz in DMSO-d$_6$): δ=82.44, 120.10, 124.66, 125.66, 126.28, 128.07, 128.51, 138.41, 139.14, 144.19, and 151.23 ppm.

Subsequently, 40.3 g (78.4 mmol) of Biphenyl derivative (B3), 23.73 g (164.6 mmol) of 2-naphthol, and 240 ml of 1,2-dichloroethane were placed into a 1 L three-necked flask. While this was stirred in an oil bath at 30° C., 7.3 ml of methanesulfonic acid was slowly added dropwise. After the dropwise addition, the temperature of the oil bath was raised to 50° C. to allow the mixture to react for 6 hours. After cooling to room temperature, this was diluted with 500 ml of MIBK. This was transferred to a separating funnel after filtering the insoluble components, and subjected to separation and washing with 300 ml of ultrapure water nine times. The organic layer was concentrated in vacuum, and the residue was dissolved in 800 ml of added THF, and crystallized from 2,500 ml of hexane. The resulting crystals were filtered off and dried to give 51.6 g of biphenyl derivative Compound (A20) in a yield of 85.8%.

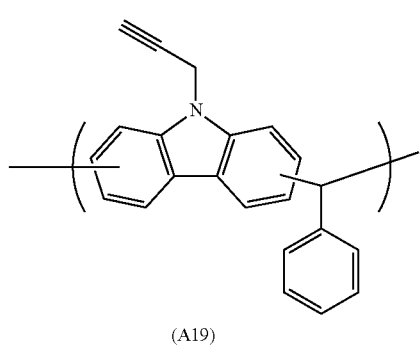

(A19)

Comparative Synthesis Examples: Synthesis of Organic Compounds

[Comparative Synthesis Example 1] Synthesis of Compound (A20)

In nitrogen atmosphere, into a 5 L four-necked flask in which 26.4 g (1.09 mol) of magnesium had been weighed, the solution of 168 g (0.54 mol) of 4,4'-dibromobiphenyl and 23.0 g (0.54 mol) of lithium chloride that had been previously dissolved into 1,000 ml of dehydrated THF (tetrahydrofuran) was added in such an amount so as to immerse the magnesium. A small amount of dibromoethene was added to start the reaction. Subsequently, the rest of the THF solution was added dropwise over 3 hours while maintaining a stable temperature. After finishing the dropwise addition, 500 ml of THF was added, and the reaction mixture was refluxed for 8 hours to prepare the Grignard reagent. After cooling to the bulk temperature of 55° C., 150 g of fluoren-9-one (0.83 mol) that had been dissolved into 400 ml of dehydrated THF was added dropwise for 2 hours. After the dropwise addition was finished, the reaction mixture was refluxed for 5.5 hours. The flask was cooled with ice-water, and the reaction was quenched with 1,000 ml of saturated aqueous ammonium chloride solution and 1,000 ml of pure water. At this stage, a white precipitate formed. To the reaction solution, 150 ml of methyl isobutyl ketone (MIBK) was added, and the suspension was transferred to a separating funnel. The water layer was removed, and the organic layer was separated and washed with 500 ml of pure water, followed by concentration in vacuum. After recrystallization from diisopropyl ether, the resulting white crystals were filtered off and dried to give 109 g of Biphenyl derivative (B3) in a yield of 51.0%.

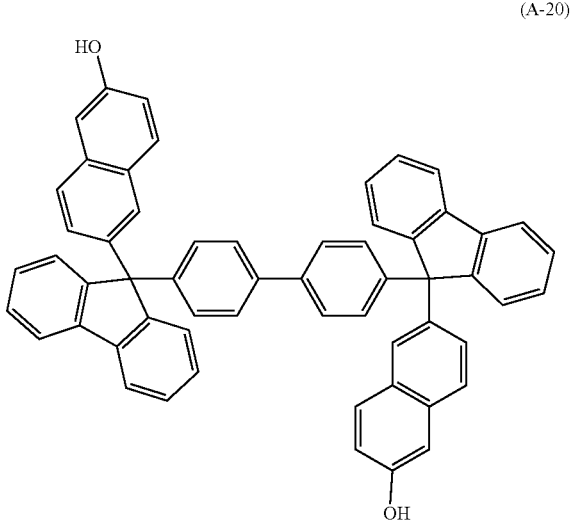 [SMILES: Oc1ccc2cc(C3(c4ccc(-c5ccc(C6(c7ccc8cc(O)ccc8c7)c7ccccc7-c7ccccc76)cc5)cc4)c4ccccc4-c4ccccc43)ccc2c1]

(A-20)

Compound (A20)
IR (KBr): ν=3528, 3389, 3059, 3030, 1633, 1604, 1506, 1493, 1446, 1219, 1181, 750, and 740 cm$^{-1}$.
$^1$H-NMR (600 MHz in DMSO-d$_6$): δ=6.98 (2H, d-d), 7.05 (2H, s-d), 7.17 (4H, d), 7.24 (2H, d-d), 7.29 (4H, t), 7.38

(4H, t), 7.40 (2H, s), 7.45 (4H, d), 7.50 (6H, d), 7.58 (2H, d), 7.93 (4H, d), and 9.72 (2H, —OH, s) ppm.

$^{13}$C-NMR (150 MHz in DMSO-$d_6$): δ=64.59, 108.35, 118.77, 120.58, 125.19, 126.11, 126.36, 126.62, 126.94, 127.16, 127.71, 127.88, 128.20, 129.35, 133.39, 138.14, 139.26, 139.59, 144.82, 150.56, and 155.39 ppm.

[Comparative Synthesis Example 2] Synthesis of Compound (A21)

A mixture of 7.7 g of Diol (A20), 3.0 g of potassium carbonate, and 40 g of N,N-dimethylformamide was heated to 55° C. To the mixture, 3.3 g of 80% propargyl bromide toluene solution was slowly added dropwise, and this was stirred with heating at 55° C. for 14 hours. After cooling to room temperature, 150 g of toluene was added thereto. This was washed with water and concentrated in vacuum to give 8.4 g of Propargyl derivative (A21).

The weight average molecular weight (Mw) and dispersity (Mw/Mn) were determined by GPC, and the following results were obtained.
(A21): Mw=1000, Mw/Mn=1.09.

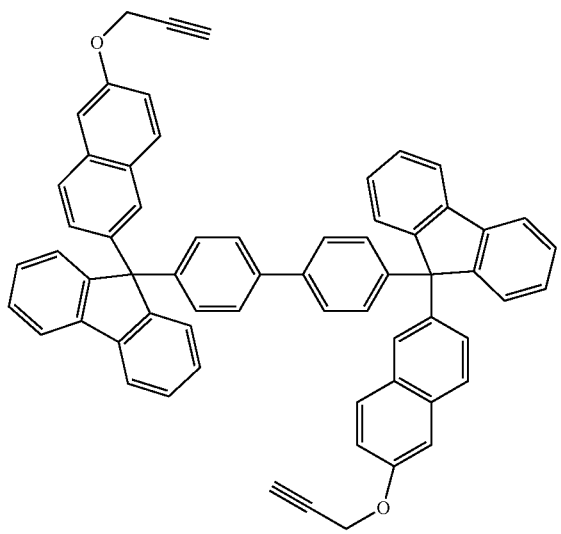

[Comparative Synthesis Example 3] Synthesis of Compound (A22)

In nitrogen atmosphere, 32.0 g of 2,7-dihydroxynaphthalene, 10.5 g of 37% aqueous formalin solution, and 270 g of 2-methoxy-1-propanol were mixed at the bulk temperature of 80° C. to a homogeneous solution. Then, 18 g of 20% 2-methoxy-1-propanol solution of para-toluenesulfonic acid was slowly added thereto, and this was stirred at the bulk temperature of 110° C. for 8 hours. After cooling to room temperature, 600 g of methyl isobutyl ketone was added thereto. The organic layer was washed with 200 g of pure water five times, and dried in vacuum. To the residue, 400 ml of THF was added, and the polymer was reprecipitated from 2,000 ml of hexane. The precipitated polymer was separated by filtration and dried in vacuum.

Subsequently, the obtained compound, 55.3 g of potassium carbonate, and 250 g of N,N-dimethylformamide were mixed and heated to 55° C. To the mixture, 59.5 g of 80% propargyl bromide toluene solution was slowly added dropwise, and this was stirred with heating at 55° C. for 22 hours. After cooling to room temperature, 150 g of toluene was added thereto. This was washed with water and concentrated in vacuum to give Propargyl derivative (A22).

The weight average molecular weight (Mw) and dispersity (Mw/Mn) were determined by GPC, and the following results were obtained.
(A22): Mw=3500, Mw/Mn=2.75.

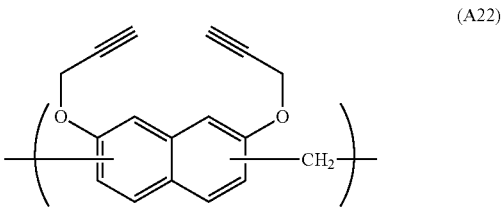

[Comparative Synthesis Example 4] Synthesis of Compound (A23)

In nitrogen atmosphere, 90.1 g of 9,9-fluorenylidene-bisnaphthol, 10.5 g of 37% aqueous formalin solution, and 270 g of 2-methoxy-1-propanol were mixed to a homogeneous solution at a bulk temperature of 80° C. Then, 18 g of 20% 2-methoxy-1-propanol solution of para-toluenesulfonic acid was slowly added thereto, and this was stirred at a bulk temperature of 110° C. for 8 hours. After cooling to room temperature, 600 g of methyl isobutyl ketone was added. The organic layer was washed with 200 g of pure water five times, and dried in vacuum. To this residue, 400 ml of THF was added, and the polymer was reprecipitated from 2,000 ml of hexane. The precipitated polymer was separated by filtration, and dried in vacuum to give Compound (A23).

The weight average molecular weight (Mw) and dispersity (Mw/Mn) were determined by GPC, and the following results were obtained.
(A23): Mw=3700, Mw/Mn=2.82

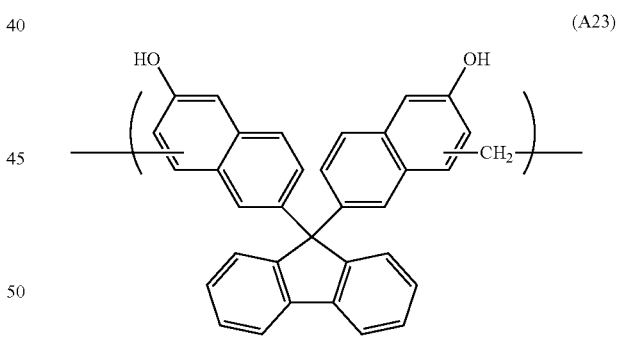

Preparation of Organic Film Material (UDL-1 to 19, Comparative UDL-1 to 8)

Into a solvent of propylene glycol monomethyl ether acetate (PGMEA) containing 0.1% by mass of FC-4430 (manufactured by 3M Japan Limited), Compounds (A3) to (A13), (A15) to (A16), (A18) to (A23), and (B5) described above, a crosslinking agent (CR1) and an acid generator (AG1) as additives, together with 1,6-diacetoxyhexane (b.p.: 260° C.) (S1) or tripropylene glycol monomethyl ether (b.p.: 242° C.) (S2) as a high boiling point solvent were dissolved in each ratio shown in Table 1. This was filtrated through 0.1 μm filter made from fluororesin to prepare each Composition for forming an organic film
(Organic Film Material: UDL-1 to 19, Comparative UDL-1 to 8).

TABLE 1

| Composition for forming organic film | Compound (1) (parts by mass) | Compound (2) (parts by mass) | Compound (3) (parts by mass) | Compound (4) (parts by mass) | PGMEA (parts by mass) |
|---|---|---|---|---|---|
| UDL-1 | A3 (5) | — | — | — | 100 |
| UDL-2 | A4 (5) | — | — | — | 100 |
| UDL-3 | A5 (5) | — | — | — | 100 |
| UDL-4 | A6 (5) | — | — | — | 100 |
| UDL-5 | A7 (5) | — | — | — | 100 |
| UDL-6 | A8 (5) | — | — | — | 100 |
| UDL-7 | A9 (5) | — | — | — | 100 |
| UDL-8 | A10 (5) | — | — | — | 100 |
| UDL-9 | A11 (5) | — | — | — | 100 |
| UDL-10 | A12 (5) | — | — | — | 100 |
| UDL-11 | A13 (5) | — | — | — | 100 |
| UDL-12 | A15 (5) | — | — | — | 100 |
| UDL-13 | A16 (5) | — | — | — | 100 |
| UDL-14 | A3 (5) | — | — | S1 (10) | 90 |
| UDL-15 | A3 (5) | — | — | S1 (10) | 90 |
| UDL-16 | A10 (5) | — | — | S1 (10) | 90 |
| UDL-17 | A10 (5) | — | — | S2 (10) | 90 |
| UDL-18 | A4 (3) | A18 (2) | — | — | 100 |
| UDL-19 | A4 (3) | A19 (2) | — | — | 100 |
| Comparative UDL-1 | A21 (5) | — | — | — | 100 |
| Comparative UDL-2 | A22 (5) | — | — | — | 100 |
| Comparative UDL-3 | A23 (5) | — | — | — | 100 |
| Comparative UDL-4 | A20 (5) | — | — | — | 100 |
| Comparative UDL-5 | B5 (5) | — | — | — | 100 |
| Comparative UDL-6 | A23 (5) | — | CR1 (1) | AG1 (0.05) | 100 |
| Comparative UDL-7 | A20 (5) | — | CR1 (1) | AG1 (0.05) | 100 |
| Comparative UDL-8 | B5 (5) | — | CR1 (1) | AG1 (0.05) | 100 |

The following are Crosslinking agent (CR1) and the Acid generator (AG1) used herein.

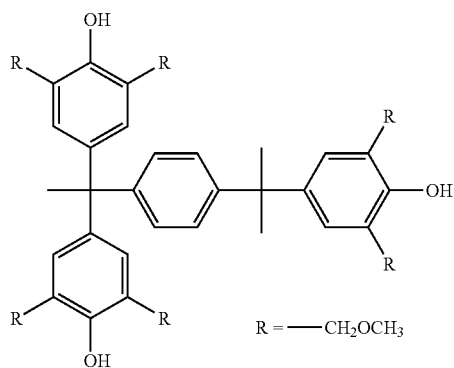

(CR1)

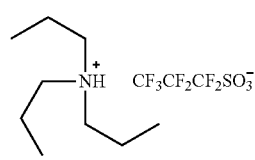

(AG1)

Example 1 Measurement of Solvent Resistance after Baking in Nitrogen Atmosphere (Examples 1-1 to 1-19, Comparative Examples 1-1 to 1-8)

Each Composition for forming an organic film (UDL-1 to 19, Comparative UDL-1 to 8) prepared in the above was applied onto a silicon substrate, and was baked at 450° C. for 60 seconds in a flow of nitrogen in which the oxygen concentration had been controlled to 0.2% or less. Then, the film thickness was measured. PGMEA solvent was dispensed thereonto and allowed to stand for 30 seconds, followed by spin drying and baking at 100° C. for 60 seconds to evaporate the PGMEA. The film thickness was measured, and the difference of film thickness before and after the PGMEA treatment was determined. The results are shown in Table 2.

TABLE 2

| | Composition for forming organic film | Film thickness after forming film: a (Å) | Film thickness after PGMEA treatment: b (Å) | b/a × 100 (%) |
|---|---|---|---|---|
| Example 1-1 | UDL-1 | 1153 | 1149 | 99.7 |
| Example 1-2 | UDL-2 | 1158 | 1158 | 100.0 |
| Example 1-3 | UDL-3 | 1152 | 1152 | 100.0 |
| Example 1-4 | UDL-4 | 1149 | 1149 | 100.0 |
| Example 1-5 | UDL-5 | 1153 | 1153 | 100.0 |
| Example 1-6 | UDL-6 | 1152 | 1151 | 99.9 |
| Example 1-7 | UDL-7 | 1146 | 1145 | 99.9 |
| Example 1-8 | UDL-8 | 1153 | 1152 | 99.9 |
| Example 1-9 | UDL-9 | 1155 | 1155 | 100.0 |
| Example 1-10 | UDL-10 | 1147 | 1146 | 99.9 |

TABLE 2-continued

| | Composition for forming organic film | Film thickness after forming film: a (Å) | Film thickness after PGMEA treatment: b (Å) | b/a × 100 (%) |
|---|---|---|---|---|
| Example 1-11 | UDL-11 | 1150 | 1150 | 100.0 |
| Example 1-12 | UDL-12 | 1157 | 1156 | 99.9 |
| Example 1-13 | UDL-13 | 1150 | 1150 | 100.0 |
| Example 1-14 | UDL-14 | 1156 | 1146 | 99.1 |
| Example 1-15 | UDL-15 | 1154 | 1151 | 99.7 |
| Example 1-16 | UDL-16 | 1158 | 1150 | 99.3 |
| Example 1-17 | UDL-17 | 1159 | 1144 | 98.7 |
| Example 1-18 | UDL-18 | 1154 | 1153 | 99.9 |
| Example 1-19 | UDL-19 | 1152 | 1151 | 99.9 |
| Comparative Example 1-1 | Comparative UDL-1 | 1148 | 1137 | 99.0 |
| Comparative Example 1-2 | Comparative UDL-2 | 1148 | 1140 | 99.3 |
| Comparative Example 1-3 | Comparative UDL-3 | 1154 | 444 | 38.5 |
| Comparative Example 1-4 | Comparative UDL-4 | 1155 | 252 | 21.8 |
| Comparative Example 1-5 | Comparative UDL-5 | 1141 | 240 | 21.0 |
| Comparative Example 1-6 | Comparative UDL-6 | 1153 | 1152 | 99.9 |
| Comparative Example 1-7 | Comparative UDL-7 | 1145 | 1140 | 99.6 |
| Comparative Example 1-8 | Comparative UDL-8 | 1150 | 1144 | 99.5 |

As shown in Table 2, each of the inventive organic film materials (Examples 1-1 to 1-19) had a film remaining rate of 99% or more after the PGMEA treatment, which revealed that the crosslinking reaction occurred even in nitrogen atmosphere to bring sufficient solvent resistance. On the other hand, in Comparative Examples 1-3 to 1-5, without adding a crosslinking agent and a thermal acid generator, sufficient solvent resistance was not attained such that all of the film remaining rate were less than 50% after the PGMEA treatment to reveal that addition of a crosslinking agent and a thermal acid generator is necessary to bring sufficient solvent resistance. These results have shown that the inventive compound having a structure which contains a triple bond(s) generates heat curing reaction to form a cured film with solvent resistance.

Example 2 Measurement of Solvent Resistance after Baking in the Atmosphere (Examples 2-1 to 2-19, Comparative Examples 2-1 to 2-8)

Each Composition for forming an organic film (UDL-1 to 19, Comparative UDL-1 to 8) prepared in the above was applied onto a silicon substrate, and was baked at 350° C. for 60 seconds in the atmosphere. Then, the film thickness was measured. PGMEA solvent was dispensed thereonto and allowed to stand for 30 seconds, followed by spin drying and baking at 100° C. for 60 seconds to evaporate the PGMEA. The film thickness was measured, and the difference of film thickness before and after the PGMEA treatment was determined. The results are shown in Table 3.

TABLE 3

| | Composition for forming organic film | Film thickness after forming film: a (Å) | Film thickness after PGMEA treatment: b (Å) | b/a × 100 (%) |
|---|---|---|---|---|
| Example 2-1 | UDL-1 | 1152 | 1149 | 99.7 |
| Example 2-2 | UDL-2 | 1151 | 1149 | 99.8 |
| Example 2-3 | UDL-3 | 1148 | 1145 | 99.7 |
| Example 2-4 | UDL-4 | 1155 | 1154 | 99.9 |
| Example 2-5 | UDL-5 | 1155 | 1155 | 100.0 |
| Example 2-6 | UDL-6 | 1143 | 1142 | 99.9 |
| Example 2-7 | UDL-7 | 1157 | 1152 | 99.6 |
| Example 2-8 | UDL-8 | 1152 | 1150 | 99.8 |
| Example 2-9 | UDL-9 | 1146 | 1143 | 99.7 |
| Example 2-10 | UDL-10 | 1147 | 1143 | 99.7 |
| Example 2-11 | UDL-11 | 1157 | 1152 | 99.6 |
| Example 2-12 | UDL-12 | 1148 | 1144 | 99.7 |
| Example 2-13 | UDL-13 | 1146 | 1146 | 100.0 |
| Example 2-14 | UDL-14 | 1153 | 1152 | 99.9 |
| Example 2-15 | UDL-15 | 1152 | 1138 | 98.8 |
| Example 2-16 | UDL-16 | 1158 | 1152 | 99.5 |
| Example 2-17 | UDL-17 | 1155 | 1152 | 99.7 |
| Example 2-18 | UDL-18 | 1152 | 1146 | 99.5 |
| Example 2-19 | UDL-19 | 1150 | 1150 | 100.0 |
| Comparative Example 2-1 | Comparative UDL-1 | 1157 | 1147 | 99.1 |
| Comparative Example 2-2 | Comparative UDL-2 | 1153 | 1143 | 99.1 |
| Comparative Example 2-3 | Comparative UDL-3 | 1146 | 1139 | 99.4 |
| Comparative Example 2-4 | Comparative UDL-4 | 1154 | 444 | 38.5 |
| Comparative Example 2-5 | Comparative UDL-5 | 1150 | 451 | 39.2 |
| Comparative Example 2-6 | Comparative UDL-6 | 1148 | 1138 | 99.1 |
| Comparative Example 2-7 | Comparative UDL-7 | 1156 | 1148 | 99.3 |
| Comparative Example 2-8 | Comparative UDL-8 | 1144 | 1138 | 99.5 |

As shown in Table 3, with the inventive composition for forming an organic film (Examples 2-1 to 2-19), each film remaining rate was 99% or more after the PGMEA treatment, showing that the crosslinking reaction also occurred in the atmosphere to attain sufficient solvent resistance. On the other hand, in Comparative Examples 2-4 and 2-5, without adding a crosslinking agent and a thermal acid generator, sufficient solvent resistance was not attained such that the film remaining rates were less than 50% after the PGMEA treatment to reveal that addition of a crosslinking agent and a thermal acid generator is necessary to attain sufficient solvent resistance. These results have shown that the inventive compound having a structure which contains a triple bond(s) generates heat curing reaction even in the atmosphere to attain solvent resistance.

Example 3 Evaluation of Heat Resistance (Examples 3-1 to 3-19, Comparative Examples 3-1 to 3-8)

Each Composition for forming an organic film (UDL-1 to 19, Comparative UDL-1 to 8) described above was applied onto a silicon substrate, and was baked at 180° C. in the atmosphere to form a coated film with a target thickness of 115 nm. The film thickness was measured. The substrate was additionally baked at 450° C. in a flow of nitrogen in which the oxygen concentration had been controlled to 0.2% or less, and the film thickness was measured (Examples 3-1 to 3-19, Comparative Examples 3-1 to 3-8). These results are shown in Table 4.

TABLE 4

| | Composition for forming organic film | Film thickness baked at 180° C.: A (Å) | Film thickness baked at 450° C.: B (Å) | (B/A) × 100 (%) |
|---|---|---|---|---|
| Example 3-1 | UDL-1 | 1153 | 1142 | 99.0 |
| Example 3-2 | UDL-2 | 1156 | 1156 | 100.0 |
| Example 3-3 | UDL-3 | 1152 | 1152 | 100.0 |
| Example 3-4 | UDL-4 | 1154 | 1154 | 100.0 |
| Example 3-5 | UDL-5 | 1155 | 1155 | 100.0 |
| Example 3-6 | UDL-6 | 1153 | 1145 | 99.3 |
| Example 3-7 | UDL-7 | 1146 | 1146 | 100.0 |
| Example 3-8 | UDL-8 | 1151 | 1145 | 99.5 |
| Example 3-9 | UDL-9 | 1147 | 1137 | 99.1 |
| Example 3-10 | UDL-10 | 1142 | 1135 | 99.4 |
| Example 3-11 | UDL-11 | 1155 | 1155 | 100.0 |
| Example 3-12 | UDL-12 | 1153 | 1143 | 99.2 |
| Example 3-13 | UDL-13 | 1152 | 1150 | 99.8 |
| Example 3-14 | UDL-14 | 1150 | 1147 | 99.7 |
| Example 3-15 | UDL-15 | 1153 | 1149 | 99.7 |
| Example 3-16 | UDL-16 | 1157 | 1146 | 99.0 |
| Example 3-17 | UDL-17 | 1157 | 1146 | 99.1 |
| Example 3-18 | UDL-18 | 1151 | 1150 | 99.9 |
| Example 3-19 | UDL-19 | 1151 | 1151 | 100.0 |
| Comparative Example 3-1 | Comparative UDL-1 | 1154 | 1011 | 87.6 |
| Comparative Example 3-2 | Comparative UDL-2 | 1154 | 1017 | 88.1 |
| Comparative Example 3-3 | Comparative UDL-3 | 1155 | 274 | 23.7 |
| Comparative Example 3-4 | Comparative UDL-4 | 1150 | 246 | 21.4 |
| Comparative Example 3-5 | Comparative UDL-5 | 1153 | 264 | 22.9 |
| Comparative Example 3-6 | Comparative UDL-6 | 1157 | 1038 | 89.7 |
| Comparative Example 3-7 | Comparative UDL-7 | 1157 | 1026 | 88.7 |
| Comparative Example 3-8 | Comparative UDL-8 | 1154 | 1023 | 88.6 |

As shown in Table 4, it was found that each organic film formed from the inventive composition for forming an organic film had high heat resistance such that the decrease of the film thickness was less than 1% even after baking at 450° C. in the inventive composition for forming an organic film (Examples 3-1 to 3-19). On the other hand, in Comparative Examples 3-1 to 3-8, the film thicknesses were decreased largely compared to the inventive organic film materials. Even in Comparative Example 3-6 to 3-8, cured with an added crosslinking agent, the film thickness was decreased by more than 10%.

Example 4 Evaluation of Gap Filling Characteristics (Examples 4-1 to 4-19, Comparative Examples 4-1 to 4-8)

Figure 3:
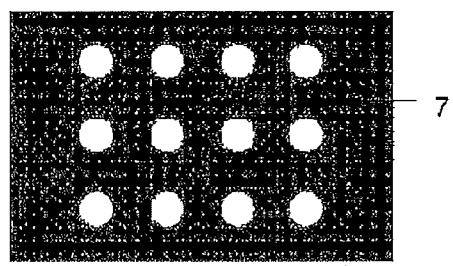
FIG. 3 is an explanatory diagram of a method for evaluating the filing characteristics in Examples.
Figure 3:
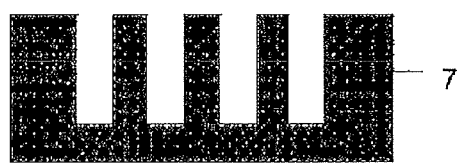
Figure 3:
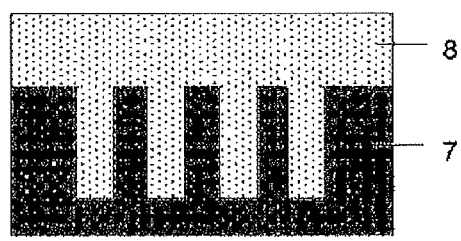

Each Composition for forming an organic film (UDL-1 to 19, Comparative UDL-1 to 8) prepared in the above was applied onto an SiO$_2$ wafer substrate having a dense hole pattern as shown in FIG. 3 (hole diameter: 0.16 µm, hole depth: 0.50 µm, the distance between the centers of two adjacent holes: 0.32 µm). This was baked at 450° C. for 60 seconds by using a hot plate in a flow of nitrogen in which the oxygen concentration had been controlled to 0.2% or less to form an organic film 8. The substrate used in this Example was a basis substrate 7 (SiO$_2$ wafer substrate) having a dense hole pattern shown in FIGS. 3(G) (bird's-eye view) and (H) (cross sectional view). Each cross sectional profile of the obtained wafer substrates were observed through scanning electron microscope (SEM) to determine whether the holes were filled with the organic film without having void therein.

The results are shown in Table 5. In case of using a composition for forming an organic film with inferior gap filling characteristics, voids are supposed to form in the holes in this evaluation. In case of using a composition for forming an organic film with good gap filling characteristics, the holes will be filled with the organic film without forming a void in this evaluation as shown in FIG. 3(I). The results are shown in Table 5.

TABLE 5

| | Composition for forming organic film | Void |
|---|---|---|
| Example 4-1 | UDL-1 | Non |
| Example 4-2 | UDL-2 | Non |
| Example 4-3 | UDL-3 | Non |
| Example 4-4 | UDL-4 | Non |
| Example 4-5 | UDL-5 | Non |
| Example 4-6 | UDL-6 | Non |
| Example 4-7 | UDL-7 | Non |
| Example 4-8 | UDL-8 | Non |
| Example 4-9 | UDL-9 | Non |
| Example 4-10 | UDL-10 | Non |
| Example 4-11 | UDL-11 | Non |
| Example 4-12 | UDL-12 | Non |
| Example 4-13 | UDL-13 | Non |
| Example 4-14 | UDL-14 | Non |
| Example 4-15 | UDL-15 | Non |
| Example 4-16 | UDL-16 | Non |
| Example 4-17 | UDL-17 | Non |
| Example 4-18 | UDL-18 | Non |
| Example 4-19 | UDL-19 | Non |
| Comparative Example 4-1 | Comparative UDL-1 | Exist |
| Comparative Example 4-2 | Comparative UDL-2 | Exist |
| Comparative Example 4-3 | Comparative UDL-3 | Exist |
| Comparative Example 4-4 | Comparative UDL-4 | Exist |
| Comparative Example 4-5 | Comparative UDL-5 | Exist |
| Comparative Example 4-6 | Comparative UDL-6 | Exist |
| Comparative Example 4-7 | Comparative UDL-7 | Exist |
| Comparative Example 4-8 | Comparative UDL-8 | Exist |

As shown in Table 5, it was found that the inventive composition for forming an organic film (Examples 4-1 to 4-19) brought excellent gap filling characteristics such that the hole pattern was successfully filled without forming a void. On the other hand, it was confirmed that Comparative Examples 4-1 to 4-8 caused voids, thereby failing to attain good gap filling characteristics. These results have shown that the inventive composition for forming an organic film ensures heat resistance to improve the gap filling characteristics due to the inventive compound having a structure that contains a triple bond(s). On the other hand, Comparative Examples 4-1 to 4-8 failed to obtain good gap filling characteristics in nitrogen atmosphere, causing voids due to insufficient heat resistance.

Example 5 Evaluation of Planarizing Characteristics (Examples 5-1 to 5-15, Comparative Examples 5-1 to 5-8)

Figure 4:
FIG. 4 is an explanatory diagram of a method for evaluating the planarizing characteristics in Examples.
Figure 4:
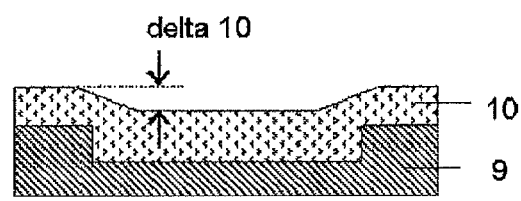

Each Composition for forming an organic film (UDL-2 to 3, 5 to 13, and 16 to 19; Comparative UDL-1 to 8) was applied onto a basis substrate 9 (SiO$_2$ wafer substrate) having a large isolated trench pattern shown in FIG. 4 (FIG. 4(J), trench width: 10 µm, trench depth: 0.10 µm). This was baked at 450° C. for 60 seconds in a flow of nitrogen in which the oxygen concentration had been controlled to 0.2% or less. The step of the organic film 10 between the trench portion and non-trench portion (delta 10 in FIG. 4(K)) was observed by using NX10 Atomic Force Microscope (AFM) manufactured by Park Systems. The results are shown in Table 6. In this evaluation, smaller step means better planarizing characteristics. Incidentally, this evaluation adopted severe conditions to evaluate planarizing characteristics such that a trench pattern with the depth of 0.10 μm was planarized by using the composition for forming an organic film with the ordinal film thickness of 0.2 μm. The results are shown in Table 6.

TABLE 6

|  | Composition for forming organic film | Step (nm) |
|---|---|---|
| Example 5-1 | UDL-2 | 50 |
| Example 5-2 | UDL-3 | 40 |
| Example 5-3 | UDL-5 | 50 |
| Example 5-4 | UDL-6 | 50 |
| Example 5-5 | UDL-7 | 50 |
| Example 5-6 | UDL-8 | 40 |
| Example 5-7 | UDL-9 | 40 |
| Example 5-8 | UDL-10 | 45 |
| Example 5-9 | UDL-11 | 45 |
| Example 5-10 | UDL-12 | 40 |
| Example 5-11 | UDL-13 | 40 |
| Example 5-12 | UDL-16 | 25 |
| Example 5-13 | UDL-17 | 25 |
| Example 5-14 | UDL-18 | 45 |
| Example 5-15 | UDL-19 | 45 |
| Comparative Example 5-1 | Comparative UDL-1 | 90 |
| Comparative Example 5-2 | Comparative UDL-2 | 90 |
| Comparative Example 5-3 | Comparative UDL-3 | 90 |
| Comparative Example 5-4 | Comparative UDL-4 | 90 |
| Comparative Example 5-5 | Comparative UDL-5 | 85 |
| Comparative Example 5-6 | Comparative UDL-6 | 95 |
| Comparative Example 5-7 | Comparative UDL-7 | 95 |
| Comparative Example 5-8 | Comparative UDL-8 | 90 |

As shown in Table 6, it was confirmed that the inventive composition for forming an organic film (Examples 5-1 to 5-15) excelled in planarizing characteristics such that each organic film had a smaller step between the trench portion and non-trench portion compared to those of Comparative Examples 5-1 to 5-8. Among the compositions for forming an organic film of Comparative Examples, the one containing a crosslinking agent showed particularly ill result of planarizing characteristics. It has shown that the inventive structure having a triple bond(s) is superior in planarizing characteristics too. In comparison between Examples 5-12 to 5-13, which contained high boiling point solvent, and Example 5-6 without containing the same, it was found that the planarizing characteristics was more improved by the addition of high boiling point solvent.

Example 6 Patterning Test (Examples 6-1 to 6-15, Comparative Examples 6-1 to 6-8)

Each Composition for forming an organic film (UDL-2 to 3, 5 to 13, and 16 to 19; Comparative UDL-1 to 8) described above was applied onto a silicon wafer substrate having an SiO$_2$ film with the thickness of 300 nm formed thereon. This was baked at 450° C. for 60 seconds in a flow of nitrogen in which the oxygen concentration had been controlled to 0.2% or less to form an organic film (resist under layer film). A CVD-SiON hard mask was formed thereon. Additionally, an organic bottom antireflective coating material (ARC-29A, manufactured by NISSAN CHEMICAL INDUSTRIES, LTD.) was applied and baked at 210° C. for 60 seconds to form an organic bottom antireflective coating with the film thickness of 80 nm. A single layer resist for ArF of a resist upper layer film material was applied thereonto, and baked at 105° C. for 60 seconds to form a photoresist film with the film thickness of 100 nm. A liquid immersion top coat composition (TC-1) was applied on the photoresist film, and baked at 90° C. for 60 seconds to form a top coat with the film thickness of 50 nm.

The resist upper layer film material (single layer resist for ArF) was prepared by dissolving Polymer (RP1), an acid generator (PAG1), and a basic compound (Amine1) in each ratio shown in Table 7 into a solvent containing 0.1% by mass of FC-4430 (manufactured by 3M Japan Limited), followed by filtration through 0.1 μm filter made from fluororesin.

TABLE 7

| | Polymer (parts by mass) | Acid generator (parts by mass) | Basic compound (parts by mass) | Solvent (parts by mass) |
|---|---|---|---|---|
| Single layer resist for ArF | PR1 (100) | PAG1 (6.6) | Amine1 (0.8) | PEGMEA (2500) |

The following shows the polymer (RP1), the acid generator (PAG1), and the basic compound (Amine1) used herein.

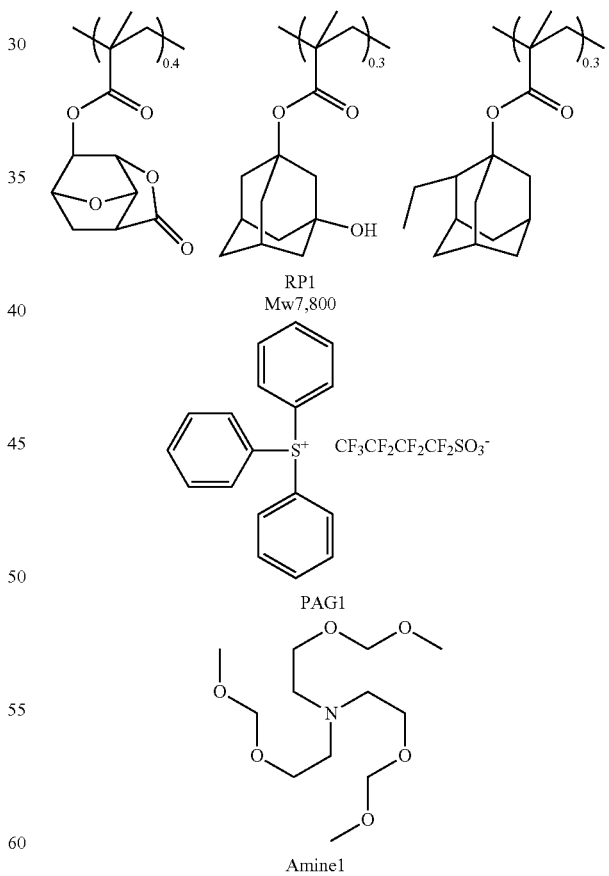

The liquid immersion top coat material (TC-1) was prepared by dissolving the top coat polymer (PP1) into an organic solvent in a ratio described in Table 8, followed by filtration through 0.1 μm filter made from fluororesin.

TABLE 8

| | Polymer (parts by mass) | Organic solvent (parts by mass) |
|---|---|---|
| TC-1 | PP1 (100) | diisoamyl ether (2700)<br>2-methyl-1-butanol (270) |

The following is the polymer (PP1) used herein.

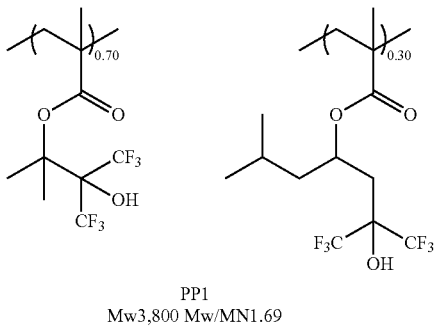

PP1
Mw3,800 Mw/MN1.69

Then, the composition was exposed by using ArF liquid immersion exposure apparatus (NSR-S610C manufactured by Nikon Corporation, NA: 1.30, σ: 0.98/0.65, 35° dipole s polarizing illumination, 6% half-tone phase shift mask), baked at 100° C. for 60 seconds (PEB), and developed with 2.38% by mass aqueous tetramethylammonium hydroxide (TMAH) solution for 30 seconds to obtain 55 nm 1:1 positive-type line-and-space pattern.

Subsequently, etching processing was performed by using an etching apparatus Telius manufactured by Tokyo Electron Limited such that the organic bottom antireflective coating and the CVD-SiON hard mask were subjected to dry etching using the resist pattern as a mask to form a hard mask pattern, the organic film was subjected to etching using the hard mask pattern as a mask to form an organic film pattern, and the $SiO_2$ film was subjected to etching processing by using the obtained organic film pattern as a mask. The etching conditions are as shown below.

Transcription conditions of the resist pattern to the SiON hard mask.
Chamber pressure 10.0 Pa
RF power 1,500 W
$CF_4$ gas flow rate 75 sccm
$O_2$ gas flow rate 15 sccm
Time 15 sec
Transcription conditions of the hard mask pattern to the organic film.
Chamber pressure 2.0 Pa
RF power 500 W
Ar gas flow rate 75 sccm
$O_2$ gas flow rate 45 sccm
Time 120 sec
Transcription conditions of the organic film pattern to the $SiO_2$ film.
Chamber pressure 2.0 Pa
RF power 2,200 W
$C_5F_{12}$ gas flow rate 20 sccm
$C_2F_6$ gas flow rate 10 sccm
Ar gas flow rate 300 sccm
$O_2$ gas flow rate 60 sccm
Time 90 sec Each pattern cross-section was observed by an electron microscope (S-4700) manufactured by Hitachi, Ltd., and the results are shown in Table 9.

TABLE 9

| | Composition for forming organic film | Pattern profile after substrate transcription etching |
|---|---|---|
| Example 6-1 | UDL-2 | Perpendicular |
| Example 6-2 | UDL-3 | Perpendicular |
| Example 6-3 | UDL-5 | Perpendicular |
| Example 6-4 | UDL-6 | Perpendicular |
| Example 6-5 | UDL-7 | Perpendicular |
| Example 6-6 | UDL-8 | Perpendicular |
| Example 6-7 | UDL-9 | Perpendicular |
| Example 6-8 | UDL-10 | Perpendicular |
| Example 6-9 | UDL-11 | Perpendicular |
| Example 6-10 | UDL-12 | Perpendicular |
| Example 6-11 | UDL-13 | Perpendicular |
| Example 6-12 | UDL-16 | Perpendicular |
| Example 6-13 | UDL-17 | Perpendicular |
| Example 6-14 | UDL-18 | Perpendicular |
| Example 6-15 | UDL-19 | Perpendicular |
| Comparative Example 6-1 | Comparative UDL-1 | Perpendicular |
| Comparative Example 6-2 | Comparative UDL-2 | Perpendicular |
| Comparative Example 6-3 | Comparative UDL-3 | Pattern collapse |
| Comparative Example 6-4 | Comparative UDL-4 | Pattern collapse |
| Comparative Example 6-5 | Comparative UDL-5 | Pattern collapse |
| Comparative Example 6-6 | Comparative UDL-6 | Perpendicular |
| Comparative Example 6-7 | Comparative UDL-7 | Perpendicular |
| Comparative Example 6-8 | Comparative UDL-8 | Perpendicular |

As shown in Table 9, it was confirmed that the inventive composition for forming an organic film was favorably used for fine processing by a multilayer resist process such that each of the resist upper layer film patterns was finally transferred to the substrate favorably in the results of the inventive composition for forming an organic film (Examples 6-1 to 6-15). On the other hand, Comparative Examples 6-3 to 6-5 failed to obtain a good pattern such that pattern collapse was caused in the patterning process since the heat resistance was insufficient and the curing was insufficient in nitrogen atmosphere as shown in Comparative Examples 1-3 to 1-5. In Comparative Examples 6-1 to 6-2 and 6-6 to 6-8, a pattern could be formed, but the heat resistance was insufficient.

Example 7 Patterning Test (Examples 7-1 to 7-15, Comparative Examples 7-1 to 7-8)

By the same method as in Example 6, forming of a laminate, patterning, and dry etching were performed except that each Composition for forming an organic film (UDL-2 to 3, 5 to 13, and 16 to 19; Comparative UDL-1 to 8) was applied onto an $SiO_2$ wafer substrate having a trench pattern (trench width: 10 μm, trench depth: 0.10 μm), and was baked at 450° C. for 60 seconds in a flow of nitrogen in which the oxygen concentration had been controlled to 0.2% or less. Each obtained pattern was observed. The results are shown in Table 10.

TABLE 10

| | Composition for forming organic film | Pattern profile after substrate transcription etching |
|---|---|---|
| Example 7-1 | UDL-2 | Perpendicular |
| Example 7-2 | UDL-3 | Perpendicular |
| Example 7-3 | UDL-5 | Perpendicular |
| Example 7-4 | UDL-6 | Perpendicular |
| Example 7-5 | UDL-7 | Perpendicular |
| Example 7-6 | UDL-8 | Perpendicular |
| Example 7-7 | UDL-9 | Perpendicular |
| Example 7-8 | UDL-10 | Perpendicular |
| Example 7-9 | UDL-11 | Perpendicular |

TABLE 10-continued

| | Composition for forming organic film | Pattern profile after substrate transcription etching |
|---|---|---|
| Example 7-10 | UDL-12 | Perpendicular |
| Example 7-11 | UDL-13 | Perpendicular |
| Example 7-12 | UDL-16 | Perpendicular |
| Example 7-13 | UDL-17 | Perpendicular |
| Example 7-14 | UDL-18 | Perpendicular |
| Example 7-15 | UDL-19 | Perpendicular |
| Comparative Example 7-1 | Comparative UDL-1 | Pattern collapse |
| Comparative Example 7-2 | Comparative UDL-2 | Pattern collapse |
| Comparative Example 7-3 | Comparative UDL-3 | Pattern collapse |
| Comparative Example 7-4 | Comparative UDL-4 | Pattern collapse |
| Comparative Example 7-5 | Comparative UDL-5 | Pattern collapse |
| Comparative Example 7-6 | Comparative UDL-6 | Pattern collapse |
| Comparative Example 7-7 | Comparative UDL-7 | Pattern collapse |
| Comparative Example 7-8 | Comparative UDL-8 | Pattern collapse |

As shown in Table 10, it was confirmed that the inventive composition for forming an organic film was favorably used for fine processing by a multilayer resist process such that each of the resist upper layer film patterns was finally transferred to the substrate favorably in the results of the inventive composition for forming an organic film (Examples 7-1 to 7-15). On the other hand, Comparative Examples 7-3 to 7-5 failed to obtain a good pattern such that pattern collapse was caused in the patterning process since the heat resistance was insufficient, the curing was insufficient in nitrogen atmosphere as shown in Comparative Examples 1-3 to 1-5, and the pattern gap was not filled sufficiently. In Comparative Examples 7-1 to 7-2 and 7-6 to 7-8, a cured film was formed to give solvent resistance, but pattern collapse occurred due to the ill gap filling of pattern, and accordingly, a favorable pattern could not be obtained finally.

As described above, it has become obvious that the inventive composition for forming an organic film containing the inventive compound brings excellent dry etching durability as well as heat resistance at a temperature of 450° C. or more and improved gap filling/planarizing characteristics even in an inert gas that does not contain oxygen, and accordingly, is a very useful composition for forming an organic film used for a multilayer resist process, and the patterning process using the same is capable of forming a fine pattern with highly accuracy even when the substrate to be processed is a patterned substrate.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A compound comprising two or more structures shown by the following general formula (1-1) in the molecule,

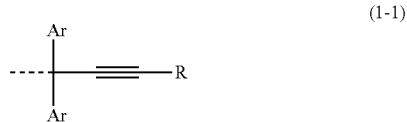

(1-1)

wherein each "Ar" independently represents an aromatic ring optionally having a substituent or an aromatic ring that contains at least one nitrogen atom and/or sulfur atom optionally having a substituent, and two Ars are optionally bonded with each other to form a ring structure; a broken line represents a bond with Y; Y represents a divalent or trivalent organic group having 6 to 30 carbon atoms that contains an aromatic ring optionally having a substituent or a heteroaromatic ring optionally having a substituent, the bonds of which are located in a structure of the aromatic ring or the heteroaromatic ring; R represents a hydrogen atom or a monovalent group having 1 to 68 carbon atoms.

2. The compound according to claim 1, wherein the compound has units shown by the following general formulae (2-1) and (2-2),

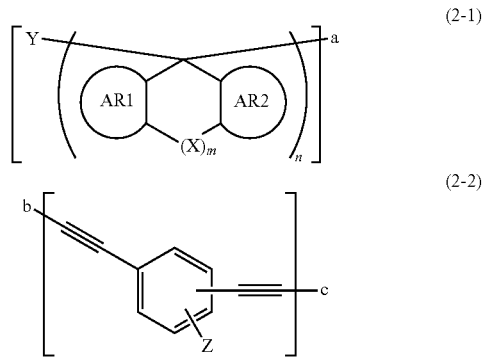

wherein AR1 and AR2 each represent a benzene ring, a pyridine ring, or a naphthalene ring optionally having an alkoxy group, an alkenyloxy group, an alkynyloxy group, or an aryloxy group having 1 to 30 carbon atoms; "m" is 0 or 1; when m=0, aromatic rings of AR1 and AR2 do not form a bridged structure with each other, when m=1, AR1 and AR2 form a bridged structure in which aromatic rings of AR1 and AR2 are bonded with each other through X; X represents a single bond or any of groups shown by the following formulae (3);

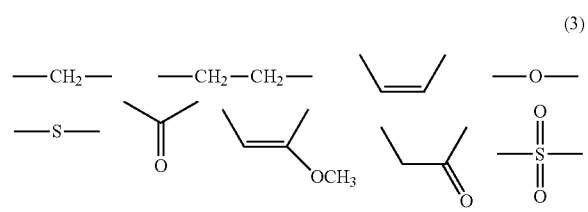

"n" is 2 or 3; Z represents a hydrogen atom or a monovalent organic group having 1 to 30 carbon atoms; "a" bonds with "b", and "c" represents a hydrogen atom or a monovalent organic group having 1 to 30 carbon atoms or bonds with "a".

3. A method for manufacturing the compound according to claim 2, comprising the steps of:
manufacturing a diol and/or triol by a reaction shown by the following formula (5-1),

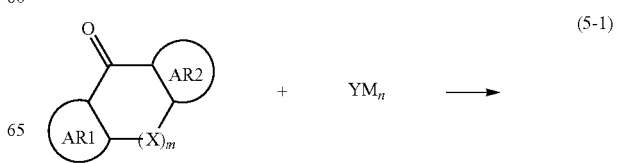

-continued

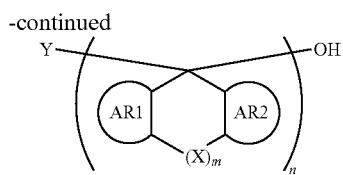

wherein M represents Li or Mg-Hal, and Hal represents Cl, Br, or I;

manufacturing a dihalogenated compound and/or a trihalogenated compound by a reaction shown by the following formula (5-2), (5-2)

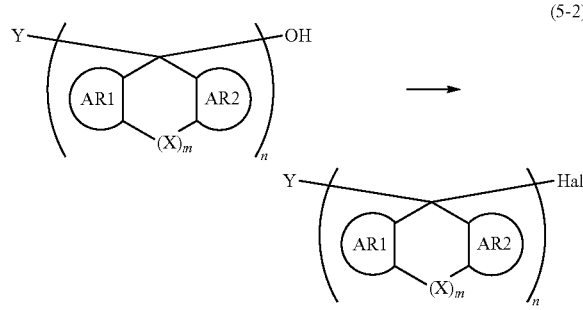

and manufacturing a polymer by a reaction shown by the following formula (5-3), (5-3)

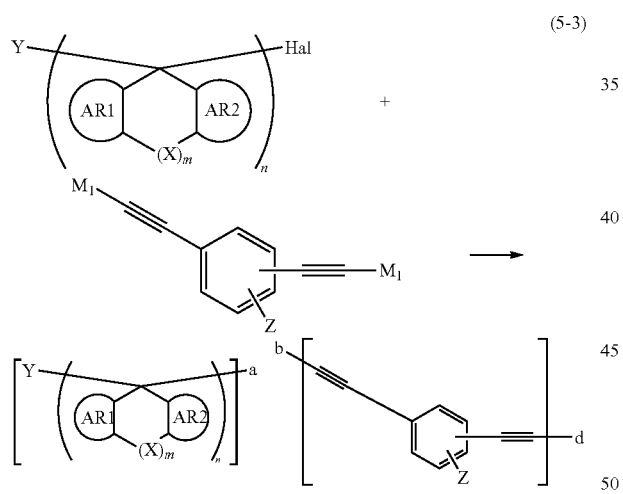

wherein M1 represents Li or Mg-Hal; "a" bonds with "b", and "d" represents a hydrogen atom or bonds with "a".

4. A method for manufacturing the compound according to claim 2, comprising the steps of:

manufacturing a diol and/or triol by a reaction shown by the following formula (5-1), (5-1)

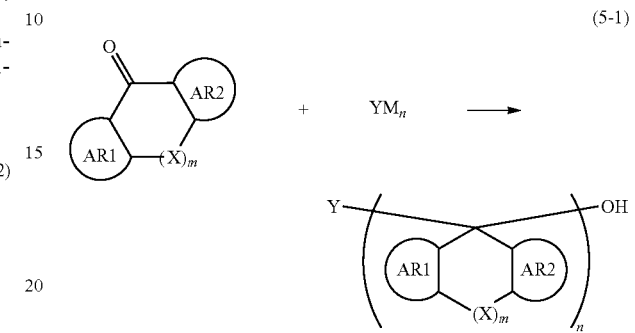

wherein M represents Li or Mg-Hal, and Hal represents Cl, Br, or I;

manufacturing a dihalogenated compound and/or a trihalogenated compound by a reaction shown by the following formula (5-2), (5-2)

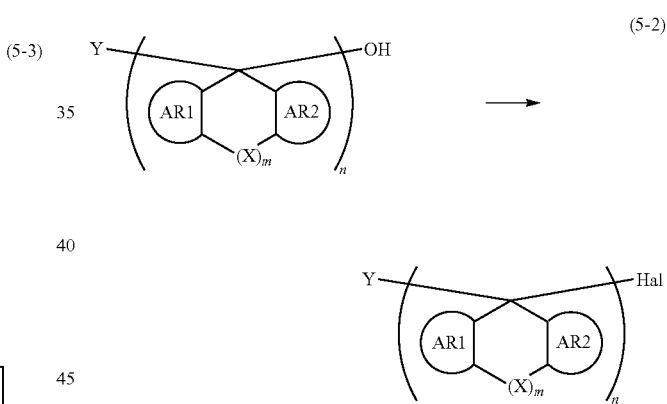

manufacturing a polymer by a reaction shown by the following formula (5-4), followed by introducing a substituent to a terminal of the polymer by a reaction shown by the following formula (5-5), (5-4)

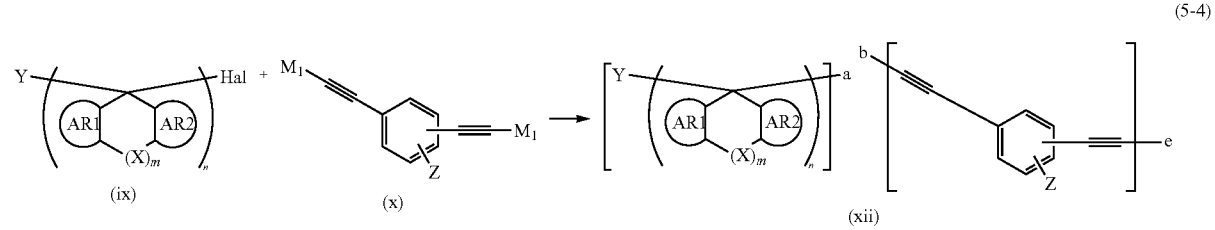

-continued

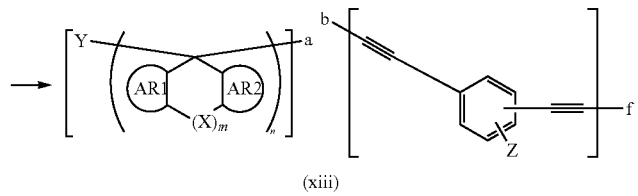

(5-5)

wherein M1 represents Li or Mg-Hal; "a" bonds with "b"; "e" represents M1 or bonds with "a"; and "f" represents a monovalent organic group having 1 to 30 carbon atoms or bonds with "a".

5. A method for manufacturing the compound according to claim 1, comprising the steps of:

manufacturing a diol and/or triol by a reaction shown by the following formula (4-1),

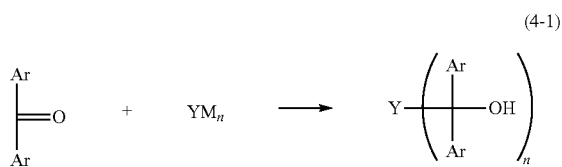

(4-1)

wherein "n" is 2 or 3; M represents Li or Mg-Hal, and Hal represents Cl, Br, or I;

manufacturing a dihalogenated compound and/or a trihalogenated compound by a reaction shown by the following formula (4-2),

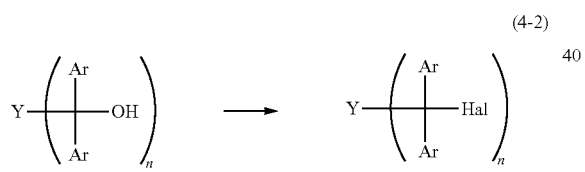

(4-2)

and manufacturing a compound by a reaction shown by the following formula (4-3),

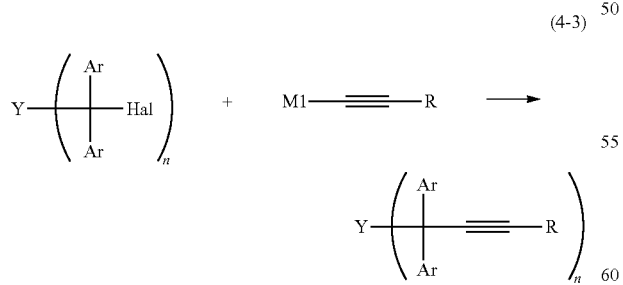

(4-3)

wherein M1 represents Li or Mg-Hal.

6. A composition for forming an organic film, comprising (A) a compound having two or more structures shown by the following general formula (1-1) in the molecule and (B) an organic solvent,

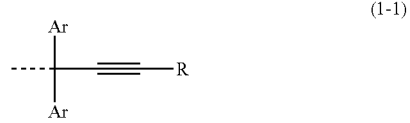

(1-1)

wherein each "Ar" independently represents an aromatic ring optionally having a substituent or an aromatic ring that contains at least one nitrogen atom and/or sulfur atom optionally having a substituent, and two Ars are optionally bonded with each other to form a ring structure; a broken line represents a bond with Y; Y represents a divalent or trivalent organic group having 6 to 30 carbon atoms that contains an aromatic ring optionally having a substituent or a heteroaromatic ring optionally having a substituent, the bonds of which are located in a structure of the aromatic ring or the heteroaromatic ring; R represents a hydrogen atom or a monovalent group having 1 to 68 carbon atoms.

7. The composition for forming an organic film according to claim 6, wherein the compound of (A) has units shown by the following general formulae (2-1) and (2-2),

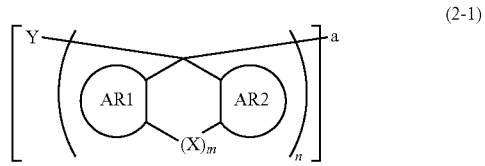

(2-1)

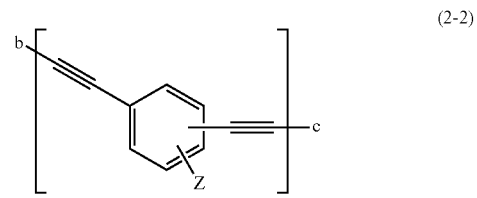

(2-2)

wherein AR1 and AR2 each represent a benzene ring, a pyridine ring, or a naphthalene ring optionally having an alkoxy group, an alkenyloxy group, an alkynyloxy group, or an aryloxy group having 1 to 30 carbon atoms; "m" is 0 or 1; when m=0, aromatic rings of AR1 and AR2 do not form a bridged structure with each other, when m=1, AR1 and AR2 form a bridged structure in which aromatic rings of AR1 and AR2 are bonded with each other through X; X represents a single bond or any of groups shown by the following formulae (3);

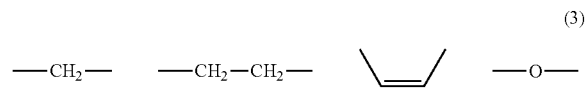

(3)

-continued

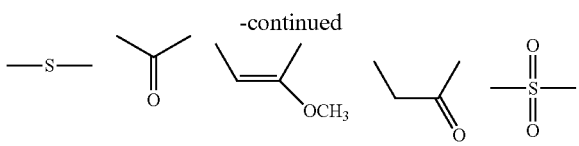

"n" is 2 or 3; Z represents a hydrogen atom or a monovalent organic group having 1 to 30 carbon atoms; "a" bonds with "b", and "c" represents a hydrogen atom or a monovalent organic group having 1 to 30 carbon atoms or bonds with "a".

8. The composition for forming an organic film according to claim 7, wherein the component (A) has a weight-average molecular weight between 500 and 20,000 Da.

9. The composition for forming an organic film according to claim 8, further comprising at least one of (C) an acid generator, (D) a surfactant, (E) a cross-linking agent, and (F) a plasticizer.

10. The composition for forming an organic film according to claim 7, further comprising at least one of (C) an acid generator, (D) a surfactant, (E) a cross-linking agent, and (F) a plasticizer.

11. The composition for forming an organic film according to claim 6, wherein the component (A) has a weight-average molecular weight between 500 and 20,000 Da.

12. The composition for forming an organic film according to claim 11, further comprising at least one of (C) an acid generator, (D) a surfactant, (E) a cross-linking agent, and (F) a plasticizer.

13. The composition for forming an organic film according to claim 6, further comprising at least one of (C) an acid generator, (D) a surfactant, (E) a cross-linking agent, and (F) a plasticizer.

* * * * *